United States Patent
Hawe et al.

(10) Patent No.: US 11,058,748 B2
(45) Date of Patent: Jul. 13, 2021

(54) STABLE LIQUID FORMULATIONS OF GLUCAGON-LIKE PEPTIDE 1 OR ANALOGUES THEREOF

(71) Applicant: Rose Pharma LLC, Hamilton (BM)

(72) Inventors: Andrea Hawe, Munich (DE); Eva Keilhauer, Munich (DE); Olimpia Popko, Munich (DE); Enda Kenny, Dublin (IE); Richard Warburg, St. Thomas, VI (US)

(73) Assignee: Rose Pharma LLC, Hamilton (BM)

( * ) Notice: Subject to any disclaimer, the term of this patent is extended or adjusted under 35 U.S.C. 154(b) by 0 days.

(21) Appl. No.: 17/109,828

(22) Filed: Dec. 2, 2020

(65) Prior Publication Data

US 2021/0169987 A1  Jun. 10, 2021

(30) Foreign Application Priority Data

Dec. 4, 2019 (GB) ..................................... 1917723

(51) Int. Cl.
*A61K 38/26* (2006.01)
*A61K 47/26* (2006.01)
*A61K 47/18* (2017.01)

(52) U.S. Cl.
CPC ............ *A61K 38/26* (2013.01); *A61K 47/183* (2013.01); *A61K 47/26* (2013.01)

(58) Field of Classification Search
CPC ...................................................... A61K 38/26
See application file for complete search history.

(56) References Cited

U.S. PATENT DOCUMENTS

| | | | | |
|---|---|---|---|---|
| 6,358,924 B1 | * | 3/2002 | Hoffmann | ............ A61K 9/0053 |
| | | | | 514/6.9 |
| 2008/0071063 A1 | * | 3/2008 | Allan | ................. C07K 16/2866 |
| | | | | 530/387.1 |
| 2019/0175701 A1 | * | 6/2019 | Chang | ...................... A61K 9/08 |

FOREIGN PATENT DOCUMENTS

| | | |
|---|---|---|
| CN | 107661288 A | 2/2018 |
| WO | WO-03/002136 A2 | 1/2003 |

* cited by examiner

*Primary Examiner* — Gyan Chandra
(74) *Attorney, Agent, or Firm* — Foley & Lardner LLP

(57) ABSTRACT

Stable liquid formulations of GLP-1 and GLP-1 analogues and method of using such formulations in the treatment of disorders or conditions are provided.

15 Claims, No Drawings

Specification includes a Sequence Listing.

```
SEQUENCE LISTING

<160> NUMBER OF SEQ ID NOS: 5

<210> SEQ ID NO 1
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: L-histidine, D-histidine, desaminohistidine,
      2-amino-histidine, beta-hydroxy-histidine, homohistidine, alpha-
      fluoromethylhistidine or alpha-methyl-histidine
<220> FEATURE:
<221> NAME/KEY: MOD_RES
<222> LOCATION: (2)..(2)
<223> OTHER INFORMATION: Val, Ala, Gly, Thr, Ile or Alpha-methyl-Ala
<220> FEATURE:
<221> NAME/KEY: MOD_RES
<222> LOCATION: (15)..(15)
<223> OTHER INFORMATION: Glu, Gln, Ala, Thr, Ser or Gly
<220> FEATURE:
<221> NAME/KEY: MOD_RES
<222> LOCATION: (21)..(21)
<223> OTHER INFORMATION: Glu, Gln, Ala, Thr, Ser or Gly
<220> FEATURE:
<221> NAME/KEY: MOD_RES
<222> LOCATION: (31)..(31)
<223> OTHER INFORMATION: Gly-NH2, Gly-OH or absent

<400> SEQUENCE: 1

His Xaa Glu Gly Thr Phe Thr Ser Asp Val Ser Ser Tyr Leu Xaa Gly
1               5                   10                  15

Gln Ala Ala Lys Xaa Phe Ile Ala Trp Leu Val Lys Gly Arg Gly
            20                  25                  30
```

```
<210> SEQ ID NO 2
<211> LENGTH: 31
<212> TYPE: PRT
<213> ORGANISM: Unknown
<220> FEATURE:
<223> OTHER INFORMATION: Description of Unknown:
      GLP-1 sequence

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

STABLE LIQUID FORMULATIONS OF GLUCAGON-LIKE PEPTIDE 1 OR ANALOGUES THEREOF

CROSS-REFERENCE TO RELATED APPLICATIONS

This application claims priority to GB 1917723.7, filed Dec. 4, 2019.

SEQUENCE LISTING

The instant application contains a Sequence Listing which has been submitted electronically in ASCII format and is hereby incorporated by reference in its entirety. Said ASCII copy, created on Jan. 4, 2021, is named 126672-0102_SL.txt and is 2,878 bytes in size.

TECHNICAL FIELD

The present disclosure relates to formulations of GLP-1 and GLP-1 analogues thereof and method of using such formulations.

BACKGROUND

The native glucagon-like peptide 1 (native GLP-1) is a 37 amino acid peptide that is secreted by the L-cells of the intestine in response to food ingestion. It has been found to stimulate insulin secretion, thereby causing glucose uptake by cells and a decrease in serum glucose levels (Mojsov, S., 1992). Native GLP-1 is susceptible to proteolytic cleavage which gives rise to two biologically active peptides; GLP-1(7-37) and GLP-1(7-36)NH$_2$.

However, these biologically active peptides have a very short half-life (<2 minutes), due to their rapid metabolic degradation by the ubiquitous dipeptidyl dipeptidase-4 (DPP-4).

ROSE-010 (Val8-GLP-1) is a GLP-1 analogue that has been made resistant to DPP-4-mediated cleavage by replacement of the alanine residue at position 8 with valine. ROSE-010 has a very high level of sequence identity with the native GLP-1(7-37) peptide and is a potent receptor agonist.

In clinical trials, ROSE-010 has been shown to reduce acute exacerbations of irritable bowel syndrome (IBS) (Hellström P M, et al., 2009). In constipation predominant IBS (IBS-C), ROSE-010 delayed gastric emptying of solids; the accelerated colonic transit at 48 h with 30 and 100 µg of ROSE-010 suggests potential for relief of constipation in IBS-C (Camilleri, M et al., 2012).

However, ROSE-010 forms noncovalent aggregates in solution (Doyle, B. D. et al, 2005) that renders the development of liquid formulations challenging.

Stable liquid formulations of GLP-1 and GLP-1 analogues such as ROSE-010 are described herein.

SUMMARY

Described herein are liquid formulations of glucagon-like peptide-1 or of GLP-1 analogues.

In certain aspects and embodiments described herein, the liquid pharmaceutical formulations of the present disclosure may include GLP-1 or GLP-1 analogues that are agonists of the GLP-1 receptor. Pharmaceutical formulations of glucagon-like peptide-1 (GLP-1 (7-37)) or of GLP-1 analogue such as ROSE-010 thereof are provided.

In other aspects and embodiments as described herein, the pharmaceutical formulations may be aqueous and may include ROSE-010 in solution. The pharmaceutical formulations of the present disclosure may advantageously withstand long-term storage. For example, the pharmaceutical formulations of the present disclosure may advantageously have a minimum stable shelf life of at least three months or more.

The pharmaceutical formulations of the present disclosure may advantageously withstand physical stress such as freeze-thaw, mechanical stress and/or elevated temperature. The pharmaceutical formulation of the present disclosure may be suitable for injection. In certain aspects and embodiments described herein the pharmaceutical formulations may be provided in pre-filled syringes. In other aspects and embodiments described herein, the pharmaceutical formulations may be provided in single-dose or multiple-dose containers.

In aspects and embodiments described herein, the pharmaceutical formulations may be aqueous and may comprise a GLP-1 or GLP-1 analogue in solution such as to obtain a liquid pharmaceutical formulation of the GLP-1 or GLP-1 analogue.

The GLP-1 or GLP-1 analogues of the present disclosure have, for example and without limitation, the amino acid sequence set forth in SEQ ID NO:1.

An exemplary embodiment of GLP-1 or GLP-1 analogues includes the biologically active peptide GLP-1(7-37) which comprises the amino acid sequence set forth in

SEQ ID NO: 2
(H-HAEGTFTSDVSSYLEGQAAKEFIAWLVKGRG-OH).

The GLP-1 analogues of the present disclosure may have one or more amino acid substitutions in comparison with the wild type GLP-1 peptide. The amino acid substitutions may include conservative amino acid substitutions. The amino acid substitutions may include for example, modification of the amino acid residue 1, modification of amino acid residue 2, modification of amino acid residue 15, modification of amino acid residue 21, modification of amino acid residue 31 and combination thereof.

Exemplary embodiments of GLP-1 analogues of the present disclosure may include, for example and without limitation, a GLP-1 analogue where the C-terminal glycine residue is absent (GLP-1(7-36)NH$_2$, SEQ ID NO: 4)
(H-HAEGTFTSDVSSYLEGQAAKEFIAWLVKGR-NH$_2$).

Additional exemplary embodiments of analogues described herein may include, for example, those where the first amino acid residue is a modified histidine residue such as for example and without limitation, L-histidine, D-histidine, desaminohistidine, 2-amino-histidine, beta-hydroxy-histidine, homohistidine, alpha-fluoromethylhistidine or alpha-methyl-histidine.

Other exemplary embodiments of analogues described herein may include those where the second amino acid is alanine, valine, glycine, threonine, isoleucine, or alpha-methyl-Ala. The ROSE-010 peptide which includes a valine residue instead of alanine at the second position (SEQ ID NO: 3)
(H-HVEGTFTSDVSSYLEGQAAKEFIAWLVKGRG-OH)

is encompassed by the present disclosure. The C-terminal glycine residue may be absent from SEQ ID NO:3 so as to form a shorter peptide (SEQ ID NO: 5)
(H-HVEGTFTSDVSSYLEGQAAKEFIAWLVKGR-NH$_2$).

Additional GLP-1 analogues of the present disclosure may include, for example, those where the amino acid residue at position 15 (with reference to SEQ ID NO:2) is glutamic acid, glutamine, alanine, threonine, serine or glycine.

Additional GLP-1 analogues of the present disclosure may include, for example, those where the amino acid residue at position 21 (with reference to SEQ ID NO:2) is glutamic acid, glutamine, alanine, threonine, serine or glycine.

Further GLP-1 analogues of the present disclosure may include, for example, those where the amino acid residue at position 31 (with reference to SEQ ID NO:2) may be absent or is Gly-NH$_2$ or Gly-OH.

GLP-1 analogues of the present disclosure may also include, for example, those that have one or more of the amino acid substitutions exemplified herein or in the various substituents of SEQ ID NO:3.

The GLP-1 and GLP-1 analogues of the present disclosure may be formulated as stable liquid formulations or stable liquid pharmaceutical formulations. The liquid pharmaceutical formulations may be water-based (i.e., aqueous formulations).

In an embodiment, the pharmaceutical formulations of the present disclosure may include, for example, the GLP-1(7-37) peptide (SEQ ID NO:2) or the GLP-1(7-36)NH$_2$ peptide (SEQ ID NO:4).

In another embodiment, the liquid pharmaceutical formulations of the present disclosure may include, for example, a GLP-1 analogue that includes or consists in the amino acid sequence set forth in SEQ ID NO:3.

In another exemplary embodiment, the GLP-1 analogues comprise an amino acid sequence at least 90%, at least 91%, at least 92%, at least 93%, at least 94%, at least 95%, at least 96%, at least 97%, at least 98%, at least 99% identical to SEQ ID NO:3 wherein the amino acid at position 2 is valine.

Other GLP-1 analogues have been described in U.S. Pat. Nos. 6,583,111 in 8,642,548, WO2007/028394 and in WO91/11457, the entire content of which is enclosed herein by reference.

The liquid pharmaceutical formulations of the present disclosure may include, for example, and without limitation, a GLP-1 or a GLP-1 analogue at a concentration ranging from about 10 μg/ml to about 1 mg/ml, at a concentration ranging from about 50 μg/ml to about 750 μg/ml, at a concentration ranging from about 100 μg/ml to about 500 μg/ml, at a concentration ranging from about 200 μg/ml to about 500 μg/ml, at a concentration of at least 300 μg/ml±20%, at a concentration of 300 μg/ml±20%, at a concentration of 300 μg/ml±10% etc.

Exemplary embodiments of pharmaceutical formulations provided are those including ROSE-010 peptide (SEQ ID NO:3) at a concentration of, for example, from about 10 μg/ml to about 1 mg/ml, from about 50 μg/ml to about 750 μg/ml, from about 100 μg/ml to about 500 μg/ml, from about 200 μg/ml to about 500 μg/ml, at a concentration of at least 300 μg/ml±10%, at a concentration of 300 μg/ml±10%, at a concentration of at least 300 μg/ml±20%, at a concentration of 300 μg/ml±20% etc.

It is to be understood herein that in a given formulation, the peptide concentration may vary over time depending on stress conditions to which it is submitted. For an initial peptide concentration of 0.300 mg/ml, a variation of ±0.05 mg/ml (i.e., approximately ±17%) may be considered within target range for quality control purposes. Higher variations may be acceptable as certain conditions require. A peptide concentration of 0.300±0.05 mg/ml, represents, for example, a range of 0.250 mg/ml to 0.350 mg/ml.

It is to be understood herein that the expression "from about 10 μg/ml to about 1 mg/ml" includes any individual values (including fractions) comprised within and including 10 μg/ml and 1 mg/ml, such as for example, 10 μg/ml, 15 μg/ml, 20 μg/ml, 30 μg/ml, 40 μg/ml, 50 μg/ml, 60 μg/ml, 70 μg/ml, 80 μg/ml, 90 μg/ml, 100 μg/ml, 125 μg/ml, 150 μg/ml, 175 μg/ml, 200 μg/ml, 225 μg/ml, 250 μg/ml, 275 μg/ml, 300 μg/ml, 325 μg/ml, 350 μg/ml, 375 μg/ml, 400 μg/ml, 425 μg/ml, 450 μg/ml, 475 μg/ml, 500 μg/ml, 525 μg/ml, 550 μg/ml, 575 μg/ml, 600 μg/ml, 625 μg/ml, 650 μg/ml, 675 μg/ml, 700 μg/ml, 725 μg/ml, 750 μg/ml, 775 μg/ml, 800 μg/ml, 825 μg/ml, 850 μg/ml, 875 μg/ml, 900 μg/ml, 925 μg/ml, 950 μg/ml, 975 μg/ml and 1 mg/ml etc.

It is to be understood herein that the expression "from about 10 μg/ml to about 1 mg/ml" also includes any individual sub-ranges (including fractions) comprised within and including from about 10 μg/ml to about 1 mg/ml, such as for example, "from about 110 μg/ml to about 490 μg/ml", "from about 205 μg/ml to about 999 μg/ml", "from about 225 μg/ml to about 875 μg/ml", "from about 200 μg/ml to about 750 μg/ml" and the like.

The same applies for similar expressions such as and not limited to "from about 200 μg/ml to about 500 μg/ml", "from about 100 μg/ml to about 500 μg/ml" and "from about 50 μg/ml to about 750 μg/ml" and the like which comprise any individual values (and fractions) comprised within and including such value and any individual sub-ranges (and fractions) comprised within and including such range.

In accordance with an aspect of the disclosure, stock solutions and formulations contain water. The type of water used in the preparation of stock solutions and formulations may meet the guidance of the European Pharmacopoeia (8th edition 2014) and may include for example, highly purified water, ultrapure water and the like. In accordance with an embodiment of the disclosure the formulations may be prepared using water for injection.

In a first aspect provided is a liquid pharmaceutical formulation that includes a GLP-1 or GLP-1 analogue and a buffering agent.

The buffering agent described herein may be a single buffer. The buffering agent described herein may be suitable for injection in a mammal (e.g., subcutaneous, intravenous, intradermal, intramuscular). The buffering agent of the present disclosure may be aqueous-based and may be selected, for example, for its lack of adverse interaction with the active ingredient. The buffering agent of the present disclosure may allow the formulation to remain at a stable pH, especially at a pH range of 6.0 to 8.0 such as for example at a pH range of 6.0 to 7.5±0.15 and more specifically within a range of 6.5 to 7.0±0.15. In an exemplary embodiment the pH range is between 6.5±0.5 to 7.0±0.5.

It is to be understood herein that for a given formulation, the pH may vary over time while remaining within an acceptable range. For example, the pH of a batch formulation may be set at an initial pH of 7.0 and the pH measured after 1 month, 3 months, 6 months storage may vary from 6.0 to 8.0.

Moreover, although the target pH of a batch formulation may be set at 7.0±0.5, a pH range of between 6.5±0.5 to 7.5±0.5 is understood herein as being within specification.

Unless indicated otherwise, pH measurements are generally performed at room temperature (e.g., generally between 20 and 25° C. and more particularly between 22-24° C.). The buffering agent described herein may include, for example and without limitation, acetate, carbonate, citrate, histidine, maleate, phosphate, succinate, tartrate, tromethamine and the like and combination thereof. Other buffering agents may be suitable.

In some embodiments of the present disclosure, the pharmaceutical formulations may include, for example, acetate (e.g., sodium acetate) as buffering agent.

In other embodiments of the present disclosure, the pharmaceutical formulations may include, for example, citrate (e.g., sodium citrate) as buffering agent.

In additional embodiments of the present disclosure, the pharmaceutical formulations may include, for example, histidine (e.g., histidine-HCl) as buffering agent.

In additional embodiments of the present disclosure, the pharmaceutical formulations may include, for example, maleate (e.g., sodium maleate) as buffering agent.

In further embodiments described herein, the pharmaceutical formulations may include, for example, phosphate as buffering agent. Exemplary embodiments of phosphate buffer include without limitation sodium phosphate, potassium phosphate, phosphate-buffered saline (PBS).

In other embodiments of the present disclosure, the pharmaceutical formulations may include, for example, succinate as buffering agent.

In other embodiments of the present disclosure, the pharmaceutical formulations may include, for example, tartrate (e.g., potassium sodium tartrate) as buffering agent.

In other embodiments of the present disclosure, the pharmaceutical formulations may include, for example, tromethamine as buffering agent.

In some embodiments of the present disclosure, the buffering agent may be at a concentration ranging from about 1 mM to about 50 mM; from about 2 mM to about 20 mM; from about 5 mM to about 20 mM; from about 5 mM to about 15 mM; from about 7.5 mM to about 12.5 mM. The concentration of the buffering agent may be, for example, 5 mM, 6 mM, 7 mM, 8 mM, 9 mM, 10 mM, 11 mM, 12 mM, 13 mM, 14 mM, 15 mM. However, it is to be understood that the concentration of the buffering agent can be either higher or lower as specific conditions require.

It is to be understood herein that the expression "from about 1 mM to about 50 mM" includes any individual values (including fractions) comprised within and including 1 mM and 50 mM, for example "from about 1 mM to about 50 mM" includes 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 34 mM, 35 mM, 36 mM, 37 mM, 38 mM, 39 mM, 40 mM, 41 mM, 42 mM, 43 mM, 44 mM, 45 mM, 46 mM, 47 mM, 48 mM, 49 mM and 50 mM.

It is to be understood herein that the expression "from about 1 mM to about 50 mM" also includes any individual sub-ranges (including fractions) comprised within and including "from about 1 mM to about 50 mM", such as for example, "from about 2 mM to about 50 mM", "from about 2 mM to about 49 mM", "from about 5 mM to about 50 mM", "from about 15 mM to about 40 mM", "from about 15 mM to about 20 mM", "from about 15 mM to about 30 mM", "from about 26 mM to about 30 mM", "from about 32 mM to about 49 mM" and the like.

The same applies for all similar expressions such as and not limited to "from about 0.5 mM to about 250 mM", "from about 5 mM to about 15 mM", "from about 7.5 mM to about 12.5 mM", "from about 25 mM to about 75 mM", "from about 50 mM to about 150 mM", from about 165 mM to about 275 mM", "from about 150 mM to about 300 mM" etc. which comprise any individual values (including fractions) comprised within and including such value and any individual sub-ranges (including fractions) comprised within and including such range.

Exemplary embodiments of the pharmaceutical formulations described herein, may include, for example and without limitation, buffering agents at a concentration of about 10 mM±10%.

In some embodiments described herein, the pharmaceutical formulations may include an acetate buffer (e.g., sodium acetate) at a concentration of 10 mM±10%.

In other embodiments described herein, the pharmaceutical formulations may include a citrate buffer (e.g., sodium citrate) at a concentration of 10 mM±10%.

In some embodiments of the present disclosure, the pharmaceutical formulations may include histidine buffer (e.g., histidine-HCl) at a concentration of 10 mM±10%.

In further embodiments described herein, the pharmaceutical formulations may include, a maleate buffer (e.g., sodium maleate) at a concentration of 10 mM±10%.

In other embodiments described herein, the pharmaceutical formulations may include a phosphate buffer (e.g., sodium phosphate) at a concentration of 10 mM±10%.

In further embodiments described herein, the pharmaceutical formulations may include, a succinate buffer at a concentration of 10 mM±10%.

In additional embodiments described herein, the pharmaceutical formulations may include, a tartrate buffer (e.g., potassium sodium tartrate) at a concentration of 10 mM±10%.

In other embodiments described herein, the pharmaceutical formulations may include a tromethamine buffer at a concentration of 10 mM±10%.

In other aspects provided is a liquid pharmaceutical formulation that includes a GLP-1 or GLP-1 analogue, a buffering agent and a tonicity agent.

The tonicity agent may contribute to the osmolality of the solution. The osmolality of the pharmaceutical formulations described herein may be adjusted to maximize the active ingredient's stability and/or to minimize discomfort to the patient upon administration. Tonicity agents described herein may render the formulation isotonic with blood and/or serum.

The osmolality of the pharmaceutical formulations of the present disclosure may vary, for example and without limitation, from 250-400 mOsmol/kg; from about 275-375 mOsmol/kg; from about between 276-369 mOsmol/kg; from about 290-370 mOsmol/kg. The osmolality of the liquid pharmaceutical formulations described herein may range from about between 275-299 mOsmol/kg (blood osmolality). However, it is to be understood that the osmolality can be either higher or lower as specific conditions require.

In some embodiments, the tonicity agent can include sugar-based tonicity agents such as sugars and polyols. Exemplary embodiments of based tonicity agents include for example and without limitation, mannitol, sucrose, glucose, dextrose, trehalose and the like.

Exemplary embodiments of tonicity agents of the present disclosure may include, for example and without limitation, dextrose, glucose, glycerin glycerol, mannitol, potassium chloride, sodium chloride, sodium sulfate, sorbitol, sucrose, trehalose and the like and combination thereof. Other tonicity agents may be suitable.

In some embodiments, the formulation may include glycerol. The concentration of glycerol may vary, for example and without limitation, from about 0.5% (v/v) to about 5% (v/v); from about 1% (v/v) to about 5% (v/v); from about 1.5% (v/v) to about 4.5% (v/v); from about 1% (v/v) to about 5% (v/v); from about 2% (v/v) to about 4% (v/v); from about 1.5% (v/v) to about 4.5% (v/v); from about 1% (v/v) to about 5% (v/v) etc. In some embodiments, the concentration of glycerol may vary, for example and without limitation, from about 2.5% (v/v) to about 3.5% (v/v). In other embodiments, the concentration of glycerol may be, for example, 2.5%±10% (or 275 mM±10%). However, it is to be understood that the concentration of glycerol can be either higher or lower as specific conditions require.

In further embodiments of the present disclosure, the pharmaceutical formulations may include, for example and without limitation, glycerol at a concentration of about 165 mM±10%.

In other embodiments of the present disclosure, the pharmaceutical formulations may include, for example and without limitation, glycerol at a concentration of about 275 mM±10%.

In other embodiments of the present disclosure, the pharmaceutical formulations may include mannitol. The concentration of mannitol in the formulation may range, for example and without limitation, from about 10 mM to about 500 mM, from about 50 mM to about 400 mM, from about 100 mM to about 400 mM; from about 150 mM to about 350 mM, from about 150 mM to about 300 mM etc. In some embodiments, the concentration of mannitol may range from about 165 mM±10% to about 275 mM±10%. However, it is to be understood that the concentration of mannitol can be either higher or lower as specific conditions require. The concentration of mannitol may also be expressed herein in weight by volume (w/v) percentages.

In further embodiments of the present disclosure, the pharmaceutical formulations may include, for example and without limitation, mannitol at a concentration of about 165 mM±10%. A concentration of 165 mM of mannitol also corresponds to approximately 3%.

In additional embodiments of the present disclosure, the pharmaceutical formulations may include, for example and without limitation, mannitol at a concentration of about 275 mM±10%. A concentration of 275 mM of mannitol also corresponds to approximately 5%.

In other embodiments of the present disclosure, the pharmaceutical formulations may include sodium chloride (NaCl). The concentration of sodium chloride used in the formulation may be determined, for example, based on the desired method of administration. In some embodiments, the concentration of sodium chloride may be for example at 0.9% (w/v)±10% so as to be isotonic to blood. In other embodiments, the concentration of sodium chloride may vary, for example and without limitation, from about 1 mM to about 250 mM; from about 10 mM to about 200 mM; from about 25 mM to about 200 mM; from about 40 mM to about 175 mM; from about 50 mM±10% to about 150 mM±10% etc. The concentration of sodium chloride may be for example and without limitation, 50 mM±10%, 130 mM±10%, 150 mM±10% etc. However, it is to be understood that the concentration of sodium chloride can be either higher or lower as specific conditions require. The concentration of sodium chloride may also be expressed herein in weight by volume (w/v) percentages.

In some embodiments of the present disclosure, the pharmaceutical formulations may include, for example and without limitation, sodium chloride at a concentration of about 50 mM±10%. A concentration of 50 mM of NaCl also corresponds to approximately 0.3%.

In other embodiments of the present disclosure, the pharmaceutical formulations may include, for example and without limitation, sodium chloride at a concentration of about 130 mM±10%. A concentration of 130 mM of NaCl also corresponds to approximately 0.7%.

In other embodiments of the present disclosure, the pharmaceutical formulations may include, for example and without limitation, sodium chloride at a concentration of about 150 mM±10%. A concentration of 150 mM of NaCl also corresponds to approximately 0.9%.

In further embodiments of the present disclosure, the pharmaceutical formulations may include, for example, sucrose. The concentration of sucrose in the formulation is expressed in % of weight/volume (w/v) and may range from about 1% (w/v) to 20% (w/v); from about 2% to 18%; from about 3% to 15%; from about 5% to 15%, etc. The concentration of sucrose in the formulation may be, for example and without limitation, 5%, 6%, 7%, 8%, 9%, 10%, 11%, 12%, 13%, 14%, 15% etc. In some embodiments, the concentration of sucrose may range, for example, from about 8%±10% to about 10%±10%. However, it is to be understood that the concentration of sucrose can be either higher or lower as specific conditions require.

In some embodiments of the present disclosure, the pharmaceutical formulations may include, for example and without limitation, sucrose at a concentration of about 5%±10%.

In some embodiments of the present disclosure, the pharmaceutical formulations may include, for example and without limitation, sucrose at a concentration of about 8%±10%.

In other embodiments of the present disclosure, the pharmaceutical formulations may include, for example and without limitation, sucrose at a concentration of about 10%±10%.

In other embodiments, the formulation may include trehalose. The concentration of trehalose may vary, for example and without limitation, from about 5% (w/v) to about 25% (w/v); from about 7.5% (w/v) to about 15% (w/v); from about 7.5% (w/v) to about 10% (w/v). In some embodiments, the concentration of trehalose may be about 10% (w/v)±10%. However, it is to be understood that the concentration of trehalose can be either higher or lower as specific conditions require.

In some embodiments of the present disclosure, the pharmaceutical formulations may include, for example and without limitation, trehalose at a concentration of about 5%±10%.

In some embodiments of the present disclosure, the pharmaceutical formulations may include, for example and without limitation, trehalose at a concentration of about 8%±10%.

In other embodiments of the present disclosure, the pharmaceutical formulations may include, for example and without limitation, trehalose at a concentration of about 10%±10%.

It is to be understood herein that the expression "from about 5% to about 15%" includes any individual values (including fractions) comprised within and including 5.0% and 15.0% such as for example 5%, 5.25%, 5.5%, 6.0%, 6.25%, 6.5%, 6.75%, 7.0%, 7.25%, 7.5%, 7.75%, 8%, 8.25%, 8.5%, 8.75%, 9.0%, 9.25%, 9.5%, 9.75%, 9.8%, 9.9%, 10%, 10.25%, 10.5%, 10.75%, 11.0%, 11.25%, 11.5%, 11.75%, 12.0%, 12.25%, 12.5%, 12.75%, 13.0%, 13.25%, 13.5%, 13.75%, 14.0%, 4.25%, 14.5%, 14.75%, 14.8%, 15.0%.

It is to be understood herein that the expression "from about 5% to about 15%" also includes any individual sub-ranges (including fractions) comprised within and including "from about 5.0% to about 15.0%", "from about 5.0% to about 10.0%", "from about 5.0% to about 8.0%", "from about 8.0% to about 10.0%", "from about 6.0% to about 7.5%" and the like.

The same applies for all similar expressions such as and not limited to "from about 8% to about 10%" or "from about 0.01 to about 0.03%" etc. which comprise any individual values (and fractions) comprised within and including such value and any individual sub-ranges (and fractions) comprised within and including such range. The expression "±10%" with respect to a given value, is to be understood herein to encompass all individual values such as +0%, +1%, +2%, +3%, +4%, +5%, +6%, +7%, +8%, +9%, +10%, −1%, −2%, −3%, −4%, −5%, −6%, −7%, −8%, −9%, −10%. For example, the expression "0.3 mg/ml±10%" includes any individual values (including fractions and ranges) comprised within 0.27 mg/ml and 0.33 mg/ml.

The same applies for all similar expressions such as and not limited to "10% (v/v)±10%" etc. which comprises values such as 9%, 10% and 11% and any fractions or ranges in between such as 9.2%, 9.5%, 10.5% and the like.

In other aspect provided, the pharmaceutical formulation may further include an excipient.

Excipients described herein include, for example, stabilizers, surfactants and combination thereof. However, it is to be understood that other excipients may be used.

Exemplary embodiments of stabilizers include, for example and without limitations, amino acids (e.g., L-amino acids or D-amino acids). Amino acid stabilizers include, for example and without limitations, alanine, arginine, glutamate, glycine, isoleucine, leucine, methionine, proline, and the like and combination thereof. Exemplary embodiments of amino acid stabilizers include for example, L-alanine, L-arginine, L-glutamate, L-glycine, L-isoleucine, L-leucine, L-methionine, L-proline, etc.

The concentration of amino acids in the pharmaceutical formulations disclosed herein may vary from about 0.5 mM to about 300 mM; from about 1 mM to about 200 mM; from about 5 mM to about 150 mM; from about 5 mM to about 100 mM; from about 7.5 mM to about 100 mM; from about 7.5 mM to about 75 mM; from about 7.5 mM to about 50 mM; from about 10 mM to about 50 mM etc. The concentration of amino acids in the pharmaceutical formulations disclosed herein may be for example and without limitations, 0.5 mM±10%, 1 mM±10%, 2 mM±10%, 3 mM±10%, 4 mM±10%, 5 mM±10%, 10 mM±10%, 15 mM±10%, 20 mM±10%, 25 mM±10%, 30 mM±10%, 35 mM±10%, 40 mM±10%, 45 mM±10% or 50 mM±10%. However, it is to be understood that the concentration of amino acids can be either higher or lower as specific conditions require.

In certain embodiments of the present disclosure, the liquid pharmaceutical formulations may include alanine (e.g., L-alanine) at a concentration of about 1 mM to about 250 mM±10%. In some embodiments of the present disclosure, the pharmaceutical formulations may include alanine at a concentration of 5 mM to about 15 mM±10%. In other embodiments of the present disclosure, the pharmaceutical formulations may include alanine at a concentration of about 10 mM±10%.

In other embodiments of the present disclosure, the liquid pharmaceutical formulations may include arginine (e.g., L-arginine) at a concentration of from about 1 mM to about 250 mM±10%. In some embodiments of the present disclosure, the liquid pharmaceutical formulations may include arginine at a concentration of about 100 mM±10% or at a concentration of 150 mM±10%.

In other embodiments of the present disclosure, the liquid pharmaceutical formulations may include glycine (e.g., L-glycine) at a concentration of from about 1 mM to about 250 mM±10%. In some embodiments of the present disclosure, the liquid pharmaceutical formulations may include glycine at a concentration of about 50 mM±10% or at a concentration of 150 mM±10%.

In other embodiments of the present disclosure, the liquid pharmaceutical formulations may include isoleucine (e.g., L-isoleucine) at a concentration of from about 1 mM to about 250 mM±10%. In some embodiments of the present disclosure, the liquid pharmaceutical formulations may include isoleucine at a concentration of about 100 mM±10% or at a concentration of 150 mM±10%.

In other embodiments of the present disclosure, the liquid pharmaceutical formulations may include leucine (e.g., L-leucine) at a concentration of from about 1 mM to about 250 mM±10%. In some embodiments of the present disclosure, the liquid pharmaceutical formulations may include leucine at a concentration of about 100 mM±10% or at a concentration of 150 mM±10%.

In certain embodiments of the present disclosure, the liquid pharmaceutical formulations may include methionine (e.g., L-methionine) at a concentration of about 1 mM to about 100 mM±10%. In some embodiments of the present disclosure, the liquid pharmaceutical formulations may include methionine at a concentration of about 5 mM to about 15 mM±10%. In other embodiments of the present disclosure, the liquid pharmaceutical formulations may include methionine at a concentration of about 10 mM±10%.

In certain embodiments of the present disclosure, the liquid pharmaceutical formulations may include proline (e.g., L-proline) at a concentration of from about 5 mM to about 300 mM±10%. In other embodiments of the present disclosure, the liquid pharmaceutical formulations may include proline at a concentration of from about 25 to about 75 mM±10%. In other embodiments of the present disclosure, the liquid pharmaceutical formulations may include proline at a concentration of about 50 mM±10%.

In a further aspect provided the pharmaceutical formulation may further include a surfactant.

Exemplary embodiments of surfactants include, for example and without limitations, non-ionic surfactants. Surfactant described herein include, for example, polysorbate 20 (PS-20), polysorbate 40 (PS-40), polysorbate 60 (PS-60), polysorbate 65 (PS-65), polysorbate 80 (PS-80), Triton X-100, poloxamer, Pluronic F-68 and the like including combinations thereof.

The concentration of the surfactant may be from about 0.001 to about 0.1%; from about 0.005 to about 0.05%; from about 0.01 to about 0.05%; from about 0.01 to about 0.04%; from about 0.01 to about 0.03%; from about 0.015 to about 0.025% etc. The concentration of the surfactant may be for example, about 0.02%±10%. However, it is to be understood that the concentration of the surfactant can be either higher or lower as specific conditions require. The concentration of surfactant is generally expressed as weight/volume (w/v). However, in some instances, the concentration of surfactant may be expressed as volume/volume (v/v).

In some embodiments described herein, the pharmaceutical formulations may include, for example, polysorbate 20 at a concentration in the range of from about 0.001 to about 0.1% (w/v), from about 0.005 to about 0.05%, from (w/v) about 0.01 to about 0.05%, from about 0.01 to about 0.03% (w/v) etc. In an exemplary embodiment, polysorbate 20 may be at a concentration about 0.02 (w/v)±10%.

In some embodiments described herein, the pharmaceutical formulations may include, for example, polysorbate 40 at a concentration in the range of from about 0.001 to about 0.1% (w/v), from about 0.005 to about 0.05% (w/v), from about 0.01 to about 0.05% (w/v), from about 0.01 to about 0.03% (w/v) etc. In an exemplary embodiment, polysorbate 40 may be at a concentration about 0.02 (w/v)±10%.

In some embodiments described herein, the pharmaceutical formulations may include, for example, polysorbate 60 at a concentration in the range of from about 0.001 to about 0.1% (w/v), from about 0.005 to about 0.05% (w/v), from about 0.01 to about 0.05% (w/v), from about 0.01 to about 0.03% (w/v) etc. In an exemplary embodiment, polysorbate 60 may be at a concentration about 0.02 (w/v)±10%.

In some embodiments described herein, the pharmaceutical formulations may include, for example, polysorbate 80 at a concentration in the range of from about 0.001 to about 0.1% (w/v), from about 0.005 to about 0.05% (w/v), from about 0.01 to about 0.05% (w/v), from about 0.01 to about 0.03% (w/v) etc. In an exemplary embodiment, polysorbate 80 may be at a concentration about 0.02 (w/v)±10%.

In some embodiments described herein, the pharmaceutical formulations may include, for example, Triton X-100 at a concentration in the range of from about 0.001 to about 0.1%, from about 0.005 to about 0.05%, from about 0.01 to about 0.05%, from about 0.01 to about 0.03% etc. In an exemplary embodiment, Triton X-100 may be at a concentration about 0.02 (v/v)±10%.

In some embodiments described herein, the pharmaceutical formulations may include, for example, Pluronic F-68 at a concentration in the range of from about 0.001 to about 0.1%, from about 0.005 to about 0.05%, from about 0.01 to about 0.05%, from about 0.01 to about 0.03% etc. In an exemplary embodiment, Pluronic F-68 may be at a concentration about 0.02 (v/v)±10%.

In certain aspects and embodiments of the present disclosure, the pharmaceutical formulations described herein may have a pH in the range of from about 5.0 to about 8.0, from about 5.0 to about 7.5; from about 5.5 to about 7.5; from about 6.0 to about 8.0; from about 6.0 to about 7.5; from about 6.0 to about 7.0; from about 6.5 to about 7.5; from about 7.0 to about 7.5 etc. The pH of the pharmaceutical formulations may be for example about, 6.0±0.15, 6.1±0.15, 6.2±0.15, 6.3±0.15, 6.4±0.15, 6.5±0.15, 6.6±0.15, 6.7±0.15, 6.8±0.15, 6.9±0.15, 7.0±0.15, 7.1±0.15, 7.2±0.15, 7.3±0.15, 7.4±0.15 or 7.5±0.15.

In an exemplary embodiment, the pH of the pharmaceutical formulations may be for example about 6.5±0.5.

In an exemplary embodiment, the pH of the pharmaceutical formulations may be for example about 7.0±0.5.

In an exemplary embodiment, the pH of the pharmaceutical formulations may be for example about 7.5±0.5.

The pharmaceutical formulation of the present disclosure may have a pH of between 6.0±0.15 to 7.5±0.15. Alternatively, the pharmaceutical formulation of the present disclosure may have a pH of between 6.5±0.15 to 7.0±0.15. Exemplary embodiments disclosed herein include, pharmaceutical formulation having a pH of 6.0±0.15. Other exemplary embodiments disclosed herein include, pharmaceutical formulation having a pH of 6.5±0.15. Further exemplary embodiments disclosed herein include, pharmaceutical formulation having a pH of 7.0±0.15. Further exemplary embodiments disclosed herein include, pharmaceutical formulation having a pH of 7.5±0.15.

In exemplary embodiments, the pharmaceutical formulations described herein may have a pH of approximately 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0 at room temperature (e.g., approximately 23° C.).

In other exemplary embodiments, the pharmaceutical formulations described herein may have a pH of approximately 6.3, 6.4, 6.5, 6.6, 6.7, 6.8, 6.9, 7.0, 7.1, 7.2, 7.3, 7.4, 7.5, 7.6, 7.7 at room temperature (e.g., approximately 23° C.).

In yet other exemplary embodiments, the pharmaceutical formulations described herein may have a pH of approximately 6.5, 6.6, 6.7, 6.8, 6.9, 7.0, 7.1, 7.2, 7.3, 7.4, 7.5 at room temperature (e.g., approximately 23° C.).

The liquid pharmaceutical formulations of the present disclosure may be stable under stress conditions. For example, the liquid formulation may be stable under mechanical stress and/or under freeze-thawing conditions.

Exemplary embodiments and aspects of the present disclosure relate to pharmaceutical formulations that may be stable for at least 1 month under refrigerated conditions (e.g., 2-8° C. including 3° C., 4° C., 5° C., 6° C., 7° C.). Exemplary and aspects of the present disclosure relate to pharmaceutical formulations that may be stable for at least 2 months; for at least 3 months or for at least 6 months under refrigerated conditions. Exemplary and aspects of the present disclosure also relate to pharmaceutical formulations that may be stable for at least 12 months under refrigerated conditions. Exemplary and aspects of the present disclosure also relate to pharmaceutical formulations that may be stable for at least 18 months under refrigerated conditions.

Further exemplary embodiments and aspects of the present disclosure relate to pharmaceutical formulations that may be stable for at least 1 month, for at least 2 months, for at least 3 months at room temperature (e.g., 15° C.-30° C. including at 25° C.). Additional exemplary embodiments and aspects of the present disclosure relate to pharmaceutical formulations that may be stable for at least 6 months at room temperature. Other exemplary embodiments and aspects of the present disclosure relate to pharmaceutical formulations that may be stable for at least 12 months at room temperature.

Moreover, additional exemplary embodiments and aspects of the present disclosure relate to pharmaceutical formulations that may be stable for at least 1 months, for at least 2 months, or for at least 3 months at elevated temperature (at least 40° C.).

In a further aspect provided is a liquid pharmaceutical formulation that includes a glucagon-like peptide 1 (GLP-1) or a GLP-1 analogue, a buffering agent, a tonicity agent, and optionally an excipient and/or a surfactant.

In yet a further aspect provided is a liquid pharmaceutical formulation that includes a glucagon-like peptide 1 (GLP-1) or a GLP-1 analogue, a buffering agent, a tonicity agent, an excipient and optionally a surfactant.

In yet a further aspect provided is a liquid pharmaceutical formulation that includes a glucagon-like peptide 1 (GLP-1) or a GLP-1 analogue, a buffering agent, a tonicity agent, a surfactant and optionally an excipient.

In yet additional aspects provided a liquid pharmaceutical formulation that includes a glucagon-like peptide 1 (GLP-1) or a GLP-1 analogue, a buffering agent, a tonicity agent, an excipient and a surfactant.

Numerous and non-limiting embodiments of pharmaceutical formulations of the present disclosure are provided below.

In some embodiments, the pharmaceutical formulation is at a pH of about 6.0±0.5 to 7.5±0.5 and includes a GLP-1 or a GLP-1 analogue, a buffering agent, and a tonicity agent at a concentration sufficient to allow isotonicity with blood and/or serum.

In some embodiments, the pharmaceutical formulation is at a pH of about 6.0±0.15 to 7.5±0.15 and includes a GLP-1 or a GLP-1 analogue, a buffering agent, and a tonicity agent at a concentration sufficient to allow isotonicity with blood and/or serum.

In additional embodiments, the pharmaceutical formulation is at a pH of about 6.0±0.5 to 7.5±0.5 and includes a GLP-1 analogue comprising or consisting of the amino acid sequence set forth in SEQ ID NO:3; a buffering agent, and a tonicity agent at a concentration sufficient to allow isotonicity with blood and/or serum.

In additional embodiments, the pharmaceutical formulation is at a pH of about 6.0±0.15 to 7.5±0.15 and includes a GLP-1 analogue comprising or consisting of the amino acid sequence set forth in SEQ ID NO:3; a buffering agent, and a tonicity agent at a concentration sufficient to allow isotonicity with blood and/or serum.

In additional embodiments, the pharmaceutical formulation is at a pH of about 6.0±0.15 to 7.5±0.5 and includes a GLP-1 analogue comprising or consisting of the amino acid sequence set forth in SEQ ID NO:3; a buffering agent, and a tonicity agent at a concentration sufficient to allow isotonicity with blood and/or serum.

In further embodiments, the pharmaceutical formulation is at a pH of about 6.5±0.15 to 7.0±0.15 and includes a GLP-1 analogue comprising or consisting of the amino acid sequence set forth in SEQ ID NO:3, a buffering agent, and a tonicity agent at a concentration sufficient to allow isotonicity with blood and/or serum.

In further embodiments, the pharmaceutical formulation is at a pH of about 6.5±0.5 to 7.0±0.5 and includes a GLP-1 analogue comprising or consisting of the amino acid sequence set forth in SEQ ID NO:3, a buffering agent, and a tonicity agent at a concentration sufficient to allow isotonicity with blood and/or serum.

The pharmaceutical formulation may further comprise an excipient and/or surfactant. The surfactant may be non-ionic and may include for example, polysorbate (e.g., PS-20, PS-40, PS-60, PS-80 and the like). The excipient may be an amino acid excipient.

In aspects and embodiments described herein, the pharmaceutical formulation comprises a GLP-1 analogue having the amino acid sequence set forth in SEQ ID NO:3, wherein the liquid pharmaceutical formulation is at a pH of between 6.5±0.15 and 7.0±0.15 and comprises histidine-HCl as buffering agent, sucrose or mannitol as tonicity agent, methionine or proline as an excipient and a surfactant.

In some embodiments, the liquid pharmaceutical formulation comprises a GLP-1 analogue at a concentration of from about 50 µg/ml to about 2 mg/ml.

In some embodiments, the liquid pharmaceutical formulation comprises a GLP-1 analogue at a concentration of from about 50 µg/ml to about 1 mg/ml.

In some embodiments, the liquid pharmaceutical formulation comprises a GLP-1 analogue at a concentration of from about 100 µg/ml to about 1 mg/ml.

In some embodiments, the liquid pharmaceutical formulation comprises a GLP-1 analogue at a concentration of from about 100 µg/ml to about 500 µg/ml.

In some embodiments, the surfactant is polysorbate-20.

In some embodiments, the liquid pharmaceutical formulation comprises a GLP-1 analogue at a concentration of from about 300 µg/ml±20%.

In some embodiments, the liquid pharmaceutical formulation is at a pH of 6.5±0.5.

In some embodiments, the liquid pharmaceutical formulation is at a pH of 7.0±0.5.

In some embodiments, the liquid pharmaceutical formulation is at a pH of 7.0±0.15.

In some embodiments, the liquid pharmaceutical formulation is at a pH of 7.5±0.5.

In aspects and embodiments described herein, the pharmaceutical formulation is at a pH of about 6.5±0.5 to 7.5±0.5, or 6.0±0.15 to 7.5±0.15 and includes a) a GLP-1 analogue comprising or consisting of the amino acid sequence set forth in SEQ ID NO:3 at a concentration of from about 10 µg/ml to about 1 mg/ml, b) a citrate buffer at a concentration of from about 1 mM to about 50 mM, c) glycerol at a concentration of from about 10 mM to about 500 mM, mannitol at a concentration of from about 10 mM to about 500 mM, sucrose at a concentration of from about 1% to about 20%, trehalose at a concentration of from about 1% to about 20% or NaCl at a concentration of from about 50 mM to about 150 mM, d) optionally polysorbate at a concentration of from about 0.001 to about 0.1% (w/v), and e) optionally an amino acid excipient at a concentration of about 0.5 mM to about 300 mM.

In aspects and embodiments described herein, the pharmaceutical formulation is at a pH of about 6.5±0.5 to 7.5±0.5, or 6.0±0.15 to 7.5±0.15 and includes a) a GLP-1 analogue comprising or consisting of the amino acid sequence set forth in SEQ ID NO:3 at a concentration of from about 10 µg/ml to about 1 mg/ml, b) a histidine buffer at a concentration of from about 1 mM to about 50 mM, c) glycerol at a concentration of from about 10 mM to about 500 mM, mannitol at a concentration of from about 10 mM to about 500 mM, sucrose at a concentration of from about 1% to about 20%, trehalose at a concentration of from about 1% to about 20% or NaCl at a concentration of from about 50 mM to about 150 mM, d) optionally polysorbate at a concentration of from about 0.001 to about 0.1% (w/v), and e) optionally an amino acid excipient at a concentration of about 0.5 mM to about 300 mM.

In further aspect and embodiments described herein, the pharmaceutical formulation is at a pH of about 6.5±0.5 to 7.5±0.5, or 6.0±0.15 to 7.5±0.15 and includes a) a GLP-1 analogue comprising or consisting of the amino acid sequence set forth in SEQ ID NO:3 at a concentration of from about 10 µg/ml to about 1 mg/ml, b) a phosphate buffer at a concentration of from about 1 mM to about 50 mM, c) glycerol at a concentration of from about 10 mM to about 500 mM, mannitol at a concentration of from about 10 mM to about 500 mM, sucrose at a concentration of from about 1% to about 20%, trehalose at a concentration of from about 1% to about 20% or NaCl at a concentration of from about 50 mM to about 150 mM, d) optionally polysorbate at a concentration of from about 0.001 to about 0.1% (w/v), and e) optionally an amino acid excipient at a concentration of about 0.5 mM to about 300 mM.

In further aspect and embodiments described herein, the pharmaceutical formulation is at a pH of about 6.5±0.5 to 7.5±0.5, or 6.0±0.15 to 7.5±0.15 and includes a) a GLP-1 analogue comprising or consisting of the amino acid sequence set forth in SEQ ID NO:3 at a concentration of from about 10 µg/ml to about 1 mg/ml, b) a maleate buffer at a concentration of from about 1 mM to about 50 mM, c)

glycerol at a concentration of from about 10 mM to about 500 mM, mannitol at a concentration of from about 10 mM to about 500 mM, sucrose at a concentration of from about 1% to about 20%, trehalose at a concentration of from about 1% to about 20% or NaCl at a concentration of from about 50 mM to about 150 mM, d) optionally polysorbate at a concentration of from about 0.001 to about 0.1% (w/v), and e) optionally an amino acid excipient at a concentration of about 0.5 mM to about 300 mM.

In additional aspects and embodiments, the pharmaceutical formulation is at a pH of about 6.5±0.5 to 7.5±0.5, or 6.0±0.15 to 7.5±0.15 and includes a GLP-1 or a GLP-1 analogue comprising or consisting of the amino acid sequence set forth in SEQ ID NO:3 at a concentration of from about 100 μg/ml to about 500 μg/ml, citrate at a concentration of from about 7.5 mM to about 12.5 mM±10% and glycerol at a concentration of from about 150 mM to about 300 mM±10%, mannitol at a concentration of from about 150 mM to about 300 mM±10%, sucrose at a concentration of from about 5% to about 15%±10% or trehalose at a concentration of from about 5% to about 15%±10%.

In additional aspects and embodiments, the pharmaceutical formulation is at a pH of about 6.5±0.5 to 7.5±0.5, or 6.0±0.15 to 7.5±0.15 and includes a GLP-1 or a GLP-1 analogue comprising or consisting of the amino acid sequence set forth in SEQ ID NO:3 at a concentration of from about 100 μg/ml to about 500 μg/ml, histidine-HCl at a concentration of from about 7.5 mM to about 12.5 mM±10% and glycerol at a concentration of from about 150 mM to about 300 mM±10%. mannitol at a concentration of from about 150 mM to about 300 mM±10%, sucrose at a concentration of from about 5% to about 15%±10% or trehalose at a concentration of from about 5% to about 15%±10%.

In other aspects and embodiments, the pharmaceutical formulation is at a pH of about 6.5±0.5 to 7.5±0.5, or 6.0±0.15 to 7.5±0.15 and includes a GLP-1 or a GLP-1 analogue comprising or consisting of the amino acid sequence set forth in SEQ ID NO:3 at a concentration of from about 100 μg/ml to about 500 μg/ml, sodium phosphate at a concentration of from about 7.5 mM to about 12.5 mM±10% and glycerol at a concentration of from about 150 mM to about 300 mM±10%, mannitol at a concentration of from about 150 mM to about 300 mM±10%, sucrose at a concentration of from about 5% to about 15%±10% or trehalose at a concentration of from about 5% to about 15%±10%.

In other aspects and embodiments, the pharmaceutical formulation is at a pH of about 6.5±0.5 to 7.5±0.5, or 6.0±0.15 to 7.5±0.15 and includes a GLP-1 or a GLP-1 analogue comprising or consisting of the amino acid sequence set forth in SEQ ID NO:3 at a concentration of from about 100 μg/ml to about 500 μg/ml, potassium phosphate at a concentration of from about 7.5 mM to about 12.5 mM±10% and glycerol at a concentration of from about 150 mM to about 300 mM±10%, mannitol at a concentration of from about 150 mM to about 300 mM±10%, sucrose at a concentration of from about 5% to about 15%±10% or trehalose at a concentration of from about 5% to about 15%±10%.

In additional aspects and embodiments, the pharmaceutical formulation is at a pH of about 6.5±0.5 to 7.5±0.5, or 6.0±0.15 to 7.5±0.15 and includes a GLP-1 or a GLP-1 analogue comprising or consisting of the amino acid sequence set forth in SEQ ID NO:3 at a concentration of from about 100 μg/ml to about 500 μg/ml, maleate at a concentration of from about 7.5 mM to about 12.5 mM±10% and glycerol at a concentration of from about 150 mM to about 300 mM±10%, mannitol at a concentration of from about 150 mM to about 300 mM±10%, sucrose at a concentration of from about 5% to about 15%±10% or trehalose at a concentration of from about 150 mM to about 300 mM±10%.

In additional embodiments, the pharmaceutical formulation further comprises a surfactant and/or an amino acid excipient. For example, the pharmaceutical formulations may comprise polysorbate at a concentration of from about 0.005 to about 0.05% (w/v)±10% and/or an amino acid excipient.

In further embodiment, the pharmaceutical formulation comprises an amino acid excipient such as methionine at a concentration of from about 5 mM to about 25 mM±10%, proline at a concentration of from about 25 mM to about 75 mM±10%, glycine at a concentration of from about 50 mM to about 150 mM±10% and/or arginine at a concentration of from about 50 mM to about 150 mM±10%.

In some embodiments, pharmaceutical formulation comprising histidine buffer may be at pH of about 6.5±0.5 to 7.5±0.5. In other embodiments, pharmaceutical formulation comprising phosphate buffer may be at pH of about 6.5±0.5 to 7.5±0.5. In other embodiments, the pharmaceutical formulation is at pH of about 6.5±0.15 to 7.0±0.15. In additional embodiments, pharmaceutical formulations that comprise citrate buffer are at a pH of about 6.5±0.15. In other embodiments, pharmaceutical formulations that comprise histidine buffer are at a pH of about 7.0±0.15. In additional embodiments, pharmaceutical formulations that comprise maleate buffer are at a pH of about 7.0±0.15. In further embodiments, pharmaceutical formulations that comprise phosphate buffer are at a pH of about 6.5±0.15.

In additional embodiments, the concentration of the GLP-1 analogue set forth in SEQ ID NO:3 in the pharmaceutical formulation is from about 10 μg/ml to about 1 mg/ml. In further embodiments, the GLP-1 analogue set forth in SEQ ID NO:3 is at a concentration of from about 100 μg/ml to about 500 μg/ml. In yet further embodiments the GLP-1 analogue set forth in SEQ ID NO:3 is at a concentration of about 0.3 mg/ml±20%. In other embodiments the GLP-1 analogue set forth in SEQ ID NO:3 is at a concentration of about 0.3 mg/ml±10%.

In further embodiments, the pharmaceutical formulation is at a pH of 6.5±0.5 to 7.5±0.5 (e.g., 6.5±0.15 to 7.0±0.15, etc.) and includes a GLP-1 analogue comprising or consisting of the amino acid sequence set forth in SEQ ID NO:3 at a concentration of from about 100 μg/ml to about 500 μg/ml, sodium citrate at a concentration of about 10 mM±10%, a tonicity agent such as glycerol at a concentration of from about 165 mM to about 275 mM±10%, sucrose at a concentration of from about 5% to about 15%, trehalose at a concentration of from about 5% to about 15% or NaCl at a concentration of from about 50 mM to about 150 mM, a surfactant such as polysorbate at a concentration of about 0.005 to 0.05% (w/v)±10% and an amino acid excipient such as methionine at a concentration of about 5 mM to about 25 mM±10%, proline at a concentration of from about 25 mM to about 75 mM±10% or arginine at a concentration of from about 50 mM to about 150 mM±10%.

In further embodiments, the pharmaceutical formulation is at a pH of 6.5±0.5 to 7.5±0.5 (e.g., 6.5±0.15 to 7.0±0.15, etc.) and includes a GLP-1 analogue comprising or consisting of the amino acid sequence set forth in SEQ ID NO:3 at a concentration of from about 100 μg/ml to about 500 μg/ml, histidine HCl at a concentration of about 10 mM±10%, a tonicity agent such as glycerol at a concentration of from about 165 mM to about 275 mM±10%, sucrose at a concentration of from about 5% to about 15%, trehalose at a concentration of from about 5% to about 15% or NaCl at a concentration of from about 50 mM to about 150 mM, a surfactant such as polysorbate at a concentration of about 0.005 to 0.05% (w/v)±10% and an amino acid excipient such as methionine at a concentration of about 5 mM to about 25 mM±10%, proline at a concentration of from about 25 mM to about 75 mM±10% or arginine at a concentration of from about 50 mM to about 150 mM±10%.

In further embodiments, the pharmaceutical formulation is at a pH of 6.5±0.5 to 7.5±0.5 (e.g., 6.5±0.15 to 7.0±0.15, etc.) and includes a GLP-1 analogue comprising or consisting of the amino acid sequence set forth in SEQ ID NO:3 at a concentration of from about 100 μg/ml to about 500 μg/ml, histidine HCl at a concentration of about 10 mM±10%, a tonicity agent such as mannitol at a concentration of from about 165 mM±10% to about 275 mM±10%, or sucrose at a concentration of from about 5%±10% to about 15%±10%, a surfactant such as polysorbate-20 at a concentration of about 0.005±10% to 0.05%±10% (w/v)±10% and an amino acid excipient such as methionine at a concentration of about 5 mM±10% to about 25 mM±10%, or proline at a concentration of from about 25 mM±10% to about 75 mM±10%.

In further embodiments, the pharmaceutical formulation is at a pH of 6.5±0.5 to 7.5±0.5 (e.g., 6.5±0.15 to 7.0±0.15 etc.) and includes a GLP-1 analogue comprising or consisting of the amino acid sequence set forth in SEQ ID NO:3 at a concentration of from about 100 μg/ml to about 500 μg/ml, maelate at a concentration of about 10 mM±10%, a tonicity agent such as glycerol at a concentration of from about 165 mM to about 275 mM±10%, sucrose at a concentration of from about 5% to about 15%, trehalose at a concentration of from about 5% to about 15% or NaCl at a concentration of from about 50 mM to about 150 mM, a surfactant such as polysorbate at a concentration of about 0.005 to 0.05% (w/v)±10% and an amino acid excipient such as methionine at a concentration of about 5 mM to about 25 mM±10%, proline at a concentration of from about 25 mM to about 75 mM±10% or arginine at a concentration of from about 50 mM to about 150 mM±10%.

In further embodiments, the pharmaceutical formulation is at a pH of 6.5±0.5 to 7.5±0.5 (e.g., 6.5±0.15 to 7.0±0.15, etc.) and includes a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, a tonicity agent such as glycerol at a concentration of from about 165 mM to about 275 mM±10%, sucrose at a concentration of from about 5% to about 15%, trehalose at a concentration of from about 5% to about 15% or NaCl at a concentration of from about 50 mM to about 150 mM, a surfactant such as polysorbate at a concentration of about 0.005 to 0.05% (w/v)±10% and an amino acid excipient such as methionine at a concentration of about 5 mM to about 25 mM±10%, proline at a concentration of from about 25 mM to about 75 mM±10% or arginine at a concentration of from about 50 mM to about 150 mM±10%.

In further embodiments, the pharmaceutical formulation is at a pH of 6.5±0.5 to 7.5±0.5 (e.g., 6.5±0.15 to 7.0±0.15, etc.) and includes a GLP-1 analogue comprising or consisting of the amino acid sequence set forth in SEQ ID NO:3 at a concentration of from about 100 μg/ml to about 500 μg/ml, potassium phosphate at a concentration of about 10 mM±10%, a tonicity agent such as glycerol at a concentration of from about 165 mM to about 275 mM±10%, sucrose at a concentration of from about 5% to about 15%, trehalose at a concentration of from about 5% to about 15% or NaCl at a concentration of from about 50 mM to about 150 mM, a surfactant such as polysorbate at a concentration of about 0.005 to 0.05% (w/v)±10% and an amino acid excipient such as methionine at a concentration of about 5 mM to about 25 mM±10%, proline at a concentration of from about 25 mM to about 75 mM±10% or arginine at a concentration of from about 50 mM to about 150 mM±10%.

Exemplary embodiments include pharmaceutical formulations at a pH of 6.5±0.5 to 7.5±0.5 (e.g., 7.0±0.5, 7.0±0.15 etc.) and including a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, and mannitol at a concentration of about 165 mM to about 275 mM±10%, sucrose at a concentration of about 5% to about 15%±10% or trehalose at a concentration of about 5% to about 15%±10%.

In further embodiments, the pharmaceutical formulation is at a pH of 6.5±0.5 to 7.5±0.5 (e.g., 7.0±0.5, 7.0±0.15 etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, mannitol at a concentration of about 165 mM to about 275 mM±10%, and polysorbate-20 at a concentration of about 0.01 to 0.03% (w/v)±10%.

In further embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, mannitol at a concentration of about 275 mM±10% and polysorbate-20 at a concentration of about 0.01 to 0.03% (w/v)±10%.

In other embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, mannitol at a concentration of about 165 mM±10% and polysorbate-20 at a concentration of about 0.01 to 0.03% (w/v)±10%.

In further embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, mannitol at a concentration of about 275 mM±10%, polysorbate-20 at a concentration of about 0.01 to 0.03% (w/v) ±10% and methionine at a concentration of about 5 mM to about 25 mM±10%.

In further embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, mannitol at a concentration of about 165 mM±10%, polysorbate-20 at a concentration of about 0.01 to 0.03% (w/v) ±10% and methionine at a concentration of about 5 mM to about 25 mM±10%.

In further embodiments, the pharmaceutical formulation is at a pH of 6.5±0.5 to 7.5±0.5 (e.g., 7.0±0.5, 7.0±0.15, etc.)

and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, mannitol at a concentration of about 275 mM±10%, polysorbate-20 at a concentration of about 0.01 to 0.03% (w/v) ±10% and proline at a concentration of about 25 mM to about 75 mM±10%.

In further embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, mannitol at a concentration of about 165 mM±10%, polysorbate-20 at a concentration of about 0.01 to 0.03% (w/v) ±10% and proline at a concentration of about 25 mM to about 75 mM±10%.

In further embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, sucrose at a concentration of about 5% to about 15%±10%, and polysorbate-20 at a concentration of about 0.01 to 0.03% (w/v)±10%.

In other embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, sucrose at a concentration of about 8%±10%, and polysorbate-20 at a concentration of about 0.01 to 0.03% (w/v) ±10%.

In other embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, sucrose at a concentration of about 10%±10%, and polysorbate-20 at a concentration of about 0.01 to 0.03% (w/v) ±10%.

In further embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, sucrose at a concentration of about 8%±10%, polysorbate-20 at a concentration of about 0.01 to 0.03% (w/v)±10% and methionine at a concentration of about 5 mM to about 25 mM±10%.

In further embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, sucrose at a concentration of about 10%±10%, polysorbate-20 at a concentration of about 0.01 to 0.03% (w/v)±10% and methionine at a concentration of about 5 mM to about 25 mM±10%.

In further embodiments, the pharmaceutical formulation is at a pH of 6.5±0.5 to 7.5±0.5 (e.g., 7.0±0.5, 7.0±0.15, etc.)

and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, sucrose at a concentration of about 8%±10%, polysorbate-20 at a concentration of about 0.01 to 0.03% (w/v)±10% and proline at a concentration of about 25 mM to about 75 mM±10%.

In further embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, sucrose at a concentration of about 10%±10%, polysorbate-20 at a concentration of about 0.01 to 0.03% (w/v)±10% and proline at a concentration of about 25 mM to about 75 mM±10%.

In further embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, trehalose at a concentration of about 5% to about 15%±10%, and polysorbate-20 at a concentration of about 0.01 to 0.03% (w/v)±10%.

In other embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, trehalose at a concentration of about 8%±10%, and polysorbate-20 at a concentration of about 0.01 to 0.03% (w/v) ±10%.

In other embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, trehalose at a concentration of about 10%±10%, and polysorbate-20 at a concentration of about 0.01 to 0.03% (w/v) ±10%.

In further embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, trehalose at a concentration of about 8%±10%, polysorbate-20 at a concentration of about 0.01 to 0.03% (w/v)±10% and methionine at a concentration of about 5 mM to about 25 mM±10%.

In further embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, trehalose at a concentration of about 10%±10%, polysorbate-20 at a concentration of about 0.01 to 0.03% (w/v) ±10% and methionine at a concentration of about 5 mM to about 25 mM±10%.

In further embodiments, the pharmaceutical formulation is at a pH of 6.5±0.5 to 7.5±0.5 (e.g., 7.0±0.5, 7.0±0.15, etc.)

and includes a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, trehalose at a concentration of about 8%±10%, polysorbate-20 at a concentration of about 0.01 to 0.03% (w/v)±10% and proline at a concentration of about 25 mM to about 75 mM±10%.

In further embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, trehalose at a concentration of about 10%±10%, polysorbate-20 at a concentration of about 0.01 to 0.03% (w/v) ±10% and proline at a concentration of about 25 mM to about 75 mM±10%.

In other embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, and mannitol at a concentration of about 165 mM to about 275 mM±10%, sucrose at a concentration of about 5% to about 15%±10% or trehalose at a concentration of about 5% to about 15%±10.

In further embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, mannitol at a concentration of about 165 mM to about 275 mM±10%, and polysorbate-20 at a concentration of about 0.01 to 0.03% (w/v)±10%.

In other embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, mannitol at a concentration of about 275 mM±10%, and polysorbate-20 at a concentration of about 0.01 to 0.03% (w/v)±10%.

In other embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, mannitol at a concentration of about 165 mM±10%, and polysorbate-20 at a concentration of about 0.01 to 0.03% (w/v)±10%.

In further embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, mannitol at a concentration of about 275 mM±10%, polysorbate-20 at a concentration of about 0.01 to 0.03% (w/v) ±10% and methionine at a concentration of about 5 mM to about 25 mM±10%.

In further embodiments, the pharmaceutical formulation is at a pH of 6.5±0.5 to 7.5±0.5 (e.g., 7.0±0.5, 7.0±0.15, etc.) and includes a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, mannitol at a concentration of about 165 mM±10%, polysorbate-20 at a concentration of about 0.01 to 0.03% (w/v) ±10% and methionine at a concentration of about 5 mM to about 25 mM±10%.

In further embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, mannitol at a concentration of about 275 mM±10%, polysorbate-20 at a concentration of about 0.01 to 0.03% (w/v) ±10% and proline at a concentration of about 25 mM to about 75 mM±10%.

In further embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, mannitol at a concentration of about 165 mM±10%, polysorbate-20 at a concentration of about 0.01 to 0.03% (w/v) ±10% and proline at a concentration of about 25 mM to about 75 mM±10%.

In further embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, sucrose at a concentration of about 5% to about 15%±10%, and polysorbate-20 at a concentration of about 0.01 to 0.03% (w/v)±10%.

In other embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, sucrose at a concentration of about 8%±10%, and polysorbate-20 at a concentration of about 0.01 to 0.03% (w/v) ±10%.

In other embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, sucrose at a concentration of about 10%±10%, and polysorbate-20 at a concentration of about 0.01 to 0.03% (w/v) ±10%.

In further embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, sucrose at a concentration of about 8%±10%, polysorbate-20 at a concentration of about 0.01 to 0.03% (w/v)±10% and methionine at a concentration of about 5 mM to about 25 mM±10%.

In further embodiments, the pharmaceutical formulation is at a pH of 6.5±0.5 to 7.5±0.5 (e.g., 7.0±0.5, 6.5±0.15, etc.)

and includes a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, sucrose at a concentration of about 10%±10%, polysorbate-20 at a concentration of about 0.01 to 0.03% (w/v)±10% and methionine at a concentration of about 5 mM to about 25 mM±10%.

In further embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, sucrose at a concentration of about 8%±10%, polysorbate-20 at a concentration of about 0.01 to 0.03% (w/v)±10% and proline at a concentration of about 25 mM to about 75 mM±10%.

In further embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, sucrose at a concentration of about 10%±10%, polysorbate-20 at a concentration of about 0.01 to 0.03% (w/v)±10% and proline at a concentration of about 25 mM to about 75 mM±10%.

In further embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, trehalose at a concentration of about 5% to about 15%±10%, and polysorbate-20 at a concentration of about 0.01 to 0.03% (w/v)±10%.

In other embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, trehalose at a concentration of about 8%±10%, and polysorbate-20 at a concentration of about 0.01 to 0.03% (w/v) ±10%.

In other embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, trehalose at a concentration of about 10%±10%, and polysorbate-20 at a concentration of about 0.01 to 0.03% (w/v) ±10%.

In further embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, trehalose at a concentration of about 8%±10%, polysorbate-20 at a concentration of about 0.01 to 0.03% (w/v)±10% and methionine at a concentration of about 5 mM to about 25 mM±10%.

In further embodiments, the pharmaceutical formulation is at a pH of 6.5±0.5 to 7.5±0.5 (e.g., 7.0±0.5, 6.5±0.15, etc.)

and includes a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, trehalose at a concentration of about 10%±10%, polysorbate-20 at a concentration of about 0.01 to 0.03% (w/v) ±10% and methionine at a concentration of about 5 mM to about 25 mM±10%.

In further embodiments, the pharmaceutical formulation is at a pH of 6.5±0.5 to 7.5±0.5 (e.g., 7.0±0.5, 6.5±0.15, etc.) and includes a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, trehalose at a concentration of about 8%±10%, polysorbate-20 at a concentration of about 0.01 to 0.03% (w/v)±10% and proline at a concentration of about 25 mM to about 75 mM±10%.

In further embodiments, the pharmaceutical formulation is at a pH of 6.5±0.5 to 7.5± (e.g., 7.0±0.5, 6.5±0.15, etc.) and includes a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, trehalose at a concentration of about 10%±10%, polysorbate-20 at a concentration of about 0.01 to 0.03% (w/v) ±10% and proline at a concentration of about 25 mM to about 75 mM±10%.

The pharmaceutical formulation of the present disclosure may be used for the treatment of irritable bowel syndrome (IBS). In exemplary embodiments, the pharmaceutical formulation may be used for relief of pain in IBS and/or for relief of constipation in IBS-C. The pharmaceutical formulation may be used for the treatment of IBS-C, of diarrhea predominant IBS (IBS-D) or of mixed or alternating type IBS (IBS-M). Prevention of pain in IBS, IBS-C, IBS-D and/or IBS-M is also contemplated.

Alternatively, the formulation of the present disclosure may be used for treatment of other diseases or conditions including without limitation diabetes, ischemia, reperfused tissue injury, dyslipidemia, diabetic cardiomyopathy, myocardial infarction, acute coronary syndrome, obesity, catabolic changes after surgery, hyperglycemia, irritable bowel syndrome, stroke, neurodegenerative disorders, memory and learning disorders, islet cell transplant, functional dyspepsia and/or regenerative therapy in mammals in need of treatment.

The term "treatment" for purposes of this disclosure refers to both therapeutic treatment and prophylactic or preventative measures. Those in need of treatment include those already with the disorder as well as those prone to have the disorder or those in whom the disorder is to be prevented.

In certain aspects and embodiments, the present disclosure therefore provides a stable liquid formulation at a pH of between 6.0±0.15 to 7.5±0.15 and that includes glucagon-like peptide 1 (GLP-1) or a GLP-1 analogue thereof, a buffering agent, and optionally a tonicity agent, excipient and/or surfactant, wherein the formulation is for use in the making of a stable pharmaceutical formulation. For example, a stable pharmaceutical formulation can be obtained by adding a tonicity agent as described herein and/or excipient as described herein to such stable liquid formulation.

In other aspects and embodiments, the present disclosure provides a method of making a stable pharmaceutical formulation that include adding an excipient and/or a surfactant to a stable formulation so as to further stabilize it,

DETAILED DESCRIPTION

The use of the terms "a" and "an" and "the" are to be construed to cover both the singular and the plural, unless otherwise indicated herein or clearly contradicted by context.

Unless specifically stated or obvious from context, as used herein the term "or" is understood to be inclusive and covers both "or" and "and".

The term "and/or" where used herein is to be taken as specific disclosure of each of the specified features or components with or without the other.

The terms "comprising", "having", "including", and "containing" are to be construed as open-ended terms (i.e., meaning "including, but not limited to") unless otherwise noted. The term "consisting of" is to be construed as close-ended.

The term "about" or "approximately" shall generally mean within 20 percent, within 10 percent, within 5, 4, 3, 2 or 1 percent of a given value or range.

As used herein the term "liquid" with respect to formulations means that the peptide is dissolved in a solution without significant precipitation.

As used herein the term "stable" with respect to a formulation refers to a formulation in which no significant aggregation and/or degradation of the GLP-1 or GLP-1 analogue occurs either in absence of stress or under one or more stress conditions.

As used herein the term "no significant aggregation and/or degradation" means aggregation and/or degradation of less than 20 percent, of less than 15 percent, less than 10 percent, less than 5 percent, less than 3 percent or less than 2 percent. For example, a formulation that shows less than 5% degradation after 1-3 months storage at 5° C., less than 10 percent degradation after 3 months storage at 25° C. and/or less than 20 percent degradation after 3 months storage at 40° C. may be considered stable. A formulation that shows less than 10 percent or even less than 5 percent degradation after freeze-thaw and/or mechanical stress may be considered stable.

As used herein the term "one or more stress conditions" refers to prolonged storage (e.g., under refrigerated conditions), accelerated storage conditions (e.g., ambient temperature and/or elevated temperature such as for example 40° C.), mechanical stress, freeze-thawing or combination thereof.

As used herein the term "high concentration of subvisible particles" encompasses for example a cumulative particle count of more than 1,000 for particles of $\geq 2$ µm, more than 500 for particles of $\geq 5$ µm, more than 100 particles of $\geq 10$ µm and/or of more than 10 particles of $\geq 25$ µm as measured by micro-flow imaging at either T0 in unstressed formulations, T–1m_25° C. and/or T–1m_40° C.

As used herein the term "low concentration of subvisible particles" encompasses for example cumulative particle counts of 1000 or below for particles $\geq 2$ µm, 275 or below for particles $\geq 5$ µm, 100 or below for particles $\geq 10$ µm and/or 30 or below for particles $\geq 25$ µm as measured by micro-flow imaging at T–1m_25° C. and/or T–1m_40° C. The term "low concentration of subvisible particles" also encompasses cumulative particle counts of 500 or below for particles $\geq 2$ µm, 200 or below for particles $\geq 5$ µm, 50 or below for particles $\geq 10$ µm and 10 and/or below for particles $\geq 25$ µm as measured by micro-flow imaging at T–3m_5° C. and/or T–3m_25° C.

The term "sugar" refers to monosaccharides, disaccharides, and polysaccharides. Examples of sugars include, but are not limited to, sucrose, glucose, dextrose, and others.

The term "long-term storage" or "prolonged storage" is understood to mean storage of at least one month, at least three months, at least six months and/or at least one year.

The term "mammal" includes, but is not limited to, a human.

The terms "pharmaceutical composition" and "pharmaceutical formulation" are used interchangeably.

Liquid pharmaceutical formulations of GLP-1 or of GLP-1 analogue thereof are provided. The liquid pharmaceutical formulations of the present disclosure support physical stress such as freeze-thaw, mechanical stress, elevated temperature and/or long-term storage.

In some instances, liquid pharmaceutical formulations that include the GLP-1 or of GLP-1 analogue, a buffering agent and a tonicity agent have been found to be stable without excipient or surfactant. Liquid pharmaceutical formulations that include GLP-1 or the GLP-1 analogue thereof a buffering agent, a tonicity agent, and optionally an excipient and/or surfactant are therefore provided.

In other instances, the present disclosure relates to liquid pharmaceutical formulations that include the GLP-1 or of GLP-1 analogue, a buffering agent, a tonicity agent, a surfactant and an excipient.

Embodiments disclosed herein relate to liquid pharmaceutical formulations that include ROSE-010 (Val8-GLP-1). The formulations of the present disclosure can comprise ROSE-010 peptide concentration of from about 10 µg/ml to about 2 mg/ml, from about 50 µg/ml to about 2 mg/ml, from about 100 µg/ml to about 2 mg/ml, from about 10 µg/ml to about 1 mg/ml, from about 100 µg/ml to about 1 mg/ml, from about 50 µg/ml to about 750 µg/ml, from about 100 µg/ml to about 500 µg/ml, from about 200 µg/ml to about 500 µg/ml, at least 1 mg/ml, at least 750 µg/ml, at least 500 µg/ml, at least 300 µg/ml and including 300 µg/ml±20% or 300 µg/ml±10%.

The pharmaceutical formulations appear more stable at a higher pH (e.g., pH 6.5±0.5 to 7.5±0.5, pH 6.0±0.15 to 7.5±0.15). For example, a pH of 6.5±0.5 to 7.5±0.5 (e.g., including 6.5±0.15 to 7.0±0.15) may be beneficial for peptide stability. In exemplary embodiments, a pH of 6.5±0.5, 7.0±0.5 (e.g., 7.0±0.15), or 7.5±0.5 may be provided by histidine buffer. In other exemplary embodiments, a pH of 6.5±0.5, (e.g., 6.5±0.15), 7.0±0.5, or 7.5±0.5 may be provided by a sodium phosphate buffer or potassium phosphate buffer.

Stability of the formulations does not appear to be influenced by the tonicity agents. However, pharmaceutical formulations that contain tonicity agents are encompassed by the present disclosure. The tonicity agent can be sugars or simpler and less reactive tonicity agents.

However, other tonicity agents can be used. The formulations may be rendered more stable by the addition of a surfactant and/or excipient or both a surfactant and an excipient.

Surfactants may thus be beneficial for the stability of the pharmaceutical formulations disclosed herein. Non-ionic surfactants such as polysorbates (e.g., PS-20, PS-40, PS-60, PS-65, PS-80 etc.), Triton X-100, poloxamer, Pluronic F-68 and the like and combination thereof can be added to the pharmaceutical formulations so as to protect GLP-1 or the GLP-1 analogues from degradation and/or aggregation.

Pharmaceutical formulations that contain polysorbates appear to protect GLP-1 or the GLP-1 analogues during mechanical stress. Polysorbates may thus help to stabilize ROSE-010 against mechanical stress, such as during shipment and product handling.

Pharmaceutical formulations that contain small amounts of amino acid excipients appear more stable.

Exemplary embodiments of pharmaceutical formulations that are disclosed herein are stable under common stress conditions, such as freeze-thaw stress and/or mechanical stress. The purity of exemplary pharmaceutical formulations disclosed herein judged by RP-UPLC is about 95% after storage at 25° C. for up to at least 3 months. Exemplary pharmaceutical formulations disclosed herein appear stable under storage temperature of 2-8° C. (e.g., for up to at least three months).

The liquid formulation of the present disclosure may be suitable for injection. In certain aspects and embodiments described herein the liquid formulation may be provided in pre-filled syringes. In other aspects and embodiments described herein, the liquid formulation may be provided in single-dose or multiple-dose containers. In yet other aspects and embodiments described herein the liquid formulation may sustain prolonged storage (long-term storage).

In exemplary embodiments, the single-dose or multiple-dose container include for example, vials (e.g. glass vials), syringes (e.g., pre-filled syringes), cartridges, injectors (e.g., pen system and other types of auto-injectors) and the like.

The formulation may also be suitable for use in non-parenteral delivery. In certain aspects, the formulation may be encapsulated for oral or mucosal (e.g., nasal) delivery.

The formulation of the present disclosure may contain doses of GLP-1 or GLP-1 analogues of at least 20 μg, at least 30 μg, at least 50 μg, at least 75 μg, at least 100 μg, at least 150 μg, at least 200 μg, at least 300 μg, at least 500 μg, at least 1 mg. The dose contained in each vial or syringe will depend on the need of the patient population.

Since liquid formulations that contains the GLP-1 or of GLP-1 analogue, a buffering agent and a tonicity agent have been found to be stable without excipient or surfactant, a liquid formulation (e.g. stock solution) that contains these elements may be prepared and stored for at least one week (i.e. at least two weeks, at least three weeks, at least one month, at least two months, at least three months etc.). A pharmaceutical composition may subsequently be reconstituted by adding other elements to make it suitable for longer storage.

In addition to the embodiments described and provided in this disclosure, the following non-limiting embodiments are particularly contemplated.

1—A pharmaceutical formulation including a GLP-1 or a GLP-1 analogue, a buffering agent, a tonicity agent and optionally an excipient and/or surfactant.

2—A pharmaceutical formulation including a GLP-1 or a GLP-1 analogue, a buffering agent, a tonicity agent, an excipient and/or a non-ionic surfactant.

3—A pharmaceutical formulation as individually or collectively listed in Table 1A and including a GLP-1 or a GLP-1 analogue.

4—A pharmaceutical formulation as individually or collectively listed in Table 1B and including a GLP-1 or a GLP-1 analogue.

5—A pharmaceutical formulation as individually or collectively listed in Table 1C and including a GLP-1 or a GLP-1 analogue.

6—A pharmaceutical formulation as individually or collectively listed in Table 1D and including a GLP-1 or a GLP-1 analogue.

7—A pharmaceutical formulation as individually or collectively listed in Table 1E and including a GLP-1 or a GLP-1 analogue.

8—A pharmaceutical formulation as individually or collectively listed in Table 4 and including a GLP-1 or a GLP-1 analogue.

9—The pharmaceutical formulation of any one of the preceding embodiments, wherein the GLP-1 or analogue thereof is GLP-1 (7-37) and comprises the amino acid sequence set forth in SEQ ID NO:2.

10—The pharmaceutical formulation of any one of the preceding embodiments, wherein the GLP-1 or analogue thereof is ROSE-010 and comprises the amino acid sequence set forth in SEQ ID NO:3.

11—The pharmaceutical formulation of any one of the preceding embodiments, wherein the GLP-1 analogue comprises an amino acid sequence at least 90% identical to SEQ ID NO:3 wherein the amino acid at position 2 is valine.

12—The pharmaceutical formulation of any one of the preceding embodiments, wherein the GLP-1 or analogue thereof is formulated to provide a dose of about 50 μg to the user.

13—The pharmaceutical formulation of any one of the preceding embodiments, wherein the GLP-1 or analogue thereof is formulated to provide a dose of about 100 μg to the user.

14—The pharmaceutical formulation of any one of the preceding embodiments, wherein the GLP-1 or analogue thereof is formulated to provide a dose of about 150 μg to the user.

15—The pharmaceutical formulation of any one of the preceding embodiments, wherein the GLP-1 or analogue thereof is formulated to provide a dose of about 200 μg to the user.

16—The pharmaceutical formulation of any one of the preceding embodiments, wherein the GLP-1 or analogue thereof is formulated to provide a dose of about 300 μg to the user.

17—The pharmaceutical formulation of any one of the preceding embodiments, wherein the GLP-1 or analogue thereof is formulated to provide a dose of about 400 μg to the user.

18—The pharmaceutical formulation of any one of the preceding embodiments, wherein the GLP-1 or analogue thereof is formulated to provide a dose of about 500 μg to the user.

19—The pharmaceutical formulation of any one of the preceding embodiments, wherein the GLP-1 or analogue thereof is at a concentration of between 10 μg/ml to 2 mg/ml.

20—The pharmaceutical formulation of any one of the preceding embodiments, wherein the GLP-1 or analogue thereof is at a concentration of between 50 μg/ml to 2 mg/ml.

21—The pharmaceutical formulation of any one of the preceding embodiments, wherein the GLP-1 or analogue thereof is at a concentration of between 100 μg/ml to 1 mg/ml.

22—The pharmaceutical formulation of any one of the preceding embodiments, wherein the GLP-1 or analogue thereof is at a concentration of between 10 μg/ml to 1 mg/ml.

23—The pharmaceutical formulation of any one of the preceding embodiments, wherein the GLP-1 or analogue thereof is at a concentration of between 50 µg/ml to 750 µg/ml.
24—The pharmaceutical formulation of any one of the preceding embodiments, wherein the GLP-1 or analogue thereof is at a concentration of between 100 µg/ml to 500 µg/ml.
25—The pharmaceutical formulation of any one of the preceding embodiments, wherein the GLP-1 or analogue thereof is at a concentration of between 200 µg/ml to 500 µg/ml.
26—The pharmaceutical formulation of any one of the preceding embodiments, wherein the GLP-1 or analogue thereof is at a concentration of 300 µg/ml±20%.
27—The pharmaceutical formulation of any one of the preceding embodiments, wherein the GLP-1 or analogue thereof is at a concentration of 300 µg/ml±10%.
28—The pharmaceutical formulation of any one of the preceding embodiments comprising a surfactant.
29—The pharmaceutical formulation of any one of the preceding embodiments comprising a non-ionic surfactant.
30—The pharmaceutical formulation of any one of the preceding embodiments comprising polysorbate 20.
31—The pharmaceutical formulation of any one of the preceding embodiments comprising polysorbate 40.
32—The pharmaceutical formulation of any one of the preceding comprising polysorbate 60.
33—The pharmaceutical formulation of any one of the preceding embodiments comprising polysorbate 65.
34—The pharmaceutical formulation of any one of the preceding embodiments comprising polysorbate 80.
35—The pharmaceutical formulation of any one of the preceding embodiments comprising Triton X-100.
36—The pharmaceutical formulation of any one of the preceding embodiments comprising poloxamer.
37—The pharmaceutical formulation of any one of the preceding embodiments comprising pluronic F-68.
38—The pharmaceutical formulation of any one of the preceding embodiments, wherein the buffering agent is acetate, citrate, histidine, phosphate, succinate, maleate or tromethamine.
39—The pharmaceutical formulation of any one of the preceding embodiments comprising citrate as buffering agent.
40—The pharmaceutical formulation of any one of the preceding embodiments comprising histidine-HCl as buffering agent.
41—The pharmaceutical formulation of any one of the preceding embodiments comprising sodium phosphate as buffering agent.
42—The pharmaceutical formulation of any one of the preceding embodiments comprising potassium phosphate as buffering agent.
43—The pharmaceutical formulation of any one of the preceding embodiments comprising maleate as buffering agent.
44—The pharmaceutical formulation of any one of the preceding embodiments comprising tromethamine as buffering agent.
45—The pharmaceutical formulation of any one of the preceding embodiments, wherein the tonicity agent is selected from the group consisting of dextrose, glucose, glycerin, glycerol, mannitol, sodium chloride, sodium sulfate, sorbitol, sucrose, trehalose and potassium chloride.
46—The pharmaceutical formulation of any one of the preceding embodiments comprising glycerol as tonicity agent.
47—The pharmaceutical formulation of any one of the preceding embodiments comprising mannitol as tonicity agent.
48—The pharmaceutical formulation of any one of the preceding embodiments comprising sucrose as tonicity agent.
49—pharmaceutical formulation of any one of the preceding embodiments comprising trehalose as tonicity agent.
50—The pharmaceutical formulation of any one of the preceding embodiments comprising amino acids excipients.
51—The pharmaceutical formulation of any one of the preceding embodiments comprising alanine as excipient.
52—The pharmaceutical formulation of any one of the preceding embodiments comprising arginine as excipient.
53—The pharmaceutical formulation of any one of the preceding embodiments comprising glycine as excipient.
54—The pharmaceutical formulation of any one of the preceding embodiments comprising leucine as excipient.
55—The pharmaceutical formulation of any one of the preceding embodiments comprising methionine as excipient.
56—The pharmaceutical formulation of any one of the preceding embodiments comprising proline as excipient.
57—The pharmaceutical formulation of any one of the preceding embodiments, wherein the pharmaceutical formulation is at a pH of between 6.5±0.5 to 7.5±0.5.
58—The pharmaceutical formulation of any one of the preceding embodiments, wherein the pharmaceutical formulation is at a pH of between 6.0±0.15 to 7.5±0.15.
59—The pharmaceutical formulation of any one of the preceding embodiments, wherein the pharmaceutical formulation is at a pH of between 6.5±0.5 to 7.0±0.5.
60—The pharmaceutical formulation of any one of the preceding embodiments, wherein the pharmaceutical formulation is at a pH of between 6.5±0.15 to 7.0±0.15.
61—The pharmaceutical formulation of any one of the preceding embodiments, wherein the formulation is at pH 6.5±0.5.
62—The pharmaceutical formulation of any one of the preceding embodiments, wherein the formulation is at pH 6.5±0.15.
63—The pharmaceutical formulation of any one of the preceding embodiments, wherein the formulation is at pH 7.0±0.5.
64—The pharmaceutical formulation of any one of the preceding embodiments, wherein the formulation is at pH 7.0±0.15.
65—The pharmaceutical formulation of any one of the preceding embodiments, wherein the formulation is at pH 7.5±0.5.
66—The pharmaceutical formulation of any one of the preceding embodiments, wherein the buffer is at concentration of from about 1 mM to about 50 mM.
67—The pharmaceutical formulation of any one of the preceding embodiments, wherein the tonicity agent is at concentration of from about 10 mM to about 500 mM.

68—The pharmaceutical formulation of any one of the preceding embodiments, wherein the tonicity agent is at concentration of from about 1% to about 20% (w/v).

69—The pharmaceutical formulation of any one of the preceding embodiments, wherein the surfactant is at a concentration of from about 0.001 to about 0.1% (w/v), 70—The pharmaceutical formulation of any one of the preceding embodiments, wherein the amino acid excipient at a concentration of from about 0.5 mM to about 300 mM.

71—A pharmaceutical formulation at a pH of about 6.5±0.5 to 7.5±0.5 or 6.0±0.15 to 7.5±0.15 and including a) a GLP-1 analogue comprising or consisting of the amino acid sequence set forth in SEQ ID NO:3 at a concentration of from about 10 μg/ml to about 1 mg/ml, b) a citrate buffer at a concentration of from about 1 mM to about 50 mM, c) glycerol at a concentration of from about 10 mM to about 500 mM, mannitol at a concentration of from about 10 mM to about 500 mM, sucrose at a concentration of from about 1% to about 20%, trehalose at a concentration of from about 1% to about 20% or NaCl at a concentration of from about 50 mM to about 150 mM, d) optionally polysorbate at a concentration of from about 0.001 to about 0.1% (w/v), and e) optionally an amino acid excipient at a concentration of about 0.5 mM to about 300 mM.

72—A pharmaceutical formulation at a pH of about 6.5±0.5 to 7.5±0.5 or 6.0±0.15 to 7.5±0.15 and including a) a GLP-1 analogue comprising or consisting of the amino acid sequence set forth in SEQ ID NO:3 at a concentration of from about 10 μg/ml to about 1 mg/ml, b) a histidine buffer at a concentration of from about 1 mM to about 50 mM, c) glycerol at a concentration of from about 10 mM to about 500 mM, mannitol at a concentration of from about 10 mM to about 500 mM, sucrose at a concentration of from about 1% to about 20%, trehalose at a concentration of from about 1% to about 20% or NaCl at a concentration of from about 50 mM to about 150 mM d) optionally polysorbate at a concentration of from about 0.001 to about 0.1% (w/v), and e) optionally an amino acid excipient at a concentration of about 0.5 mM to about 300 mM.

73—A pharmaceutical formulation at a pH of about 6.5±0.5 to 7.5±0.5 or 6.0±0.15 to 7.5±0.15 and including a) a GLP-1 analogue comprising or consisting of the amino acid sequence set forth in SEQ ID NO:3 at a concentration of from about 10 μg/ml to about 1 mg/ml, b) a maleate buffer at a concentration of from about 1 mM to about 50 mM, c) glycerol at a concentration of from about 10 mM to about 500 mM, mannitol at a concentration of from about 10 mM to about 500 mM, sucrose at a concentration of from about 1% to about 20%, trehalose at a concentration of from about 1% to about 20% or NaCl at a concentration of from about 50 mM to about 150 mM, d) optionally polysorbate at a concentration of from about 0.001 to about 0.1% (w/v), and e) optionally an amino acid excipient at a concentration of about 0.5 mM to about 300 mM.

74—A pharmaceutical formulation at a pH of about 6.5±0.5 to 7.5±0.5 or 6.0±0.15 to 7.5±0.15 and including a) a GLP-1 analogue comprising or consisting of the amino acid sequence set forth in SEQ ID NO:3 at a concentration of from about 10 μg/ml to about 1 mg/ml, b) a phosphate buffer at a concentration of from about 1 mM to about 50 mM, c) glycerol at a concentration of from about 10 mM to about 500 mM, mannitol at a concentration of from about 10 mM to about 500 mM, sucrose at a concentration of from about 1% to about 20%, trehalose at a concentration of from about 1% to about 20% or NaCl at a concentration of from about 50 mM to about 150 mM d) optionally polysorbate at a concentration of from about 0.001 to about 0.1% (w/v), and e) optionally an amino acid excipient at a concentration of about 0.5 mM to about 300 mM.

75—A pharmaceutical formulation at a pH of about 6.5±0.5 to 7.5±0.5 or 6.0±0.15 to 7.5±0.15 and including a GLP-1 or a GLP-1 analogue comprising or consisting of the amino acid sequence set forth in SEQ ID NO:3 at a concentration of from about 100 μg/ml to about 500 μg/ml, citrate at a concentration of from about 7.5 mM to about 12.5 mM±10% and glycerol at a concentration of from about 150 mM to about 300 mM±10%, mannitol at a concentration of from about 150 mM to about 300 mM±10%, sucrose at a concentration of from about 5% to about 15%±10% or trehalose at a concentration of from about 5% to about 15%±10%.

76—A pharmaceutical formulation at a pH of about 6.5±0.5 to 7.5±0.5 or 6.0±0.15 to 7.5±0.15 and including a GLP-1 or a GLP-1 analogue comprising or consisting of the amino acid sequence set forth in SEQ ID NO:3 at a concentration of from about 100 μg/ml to about 500 μg/ml, histidine-HCl at a concentration of from about 7.5 mM to about 12.5 mM±10% and glycerol at a concentration of from about 150 mM to about 300 mM±10%, mannitol at a concentration of from about 150 mM to about 300 mM±10%, sucrose at a concentration of from about 5% to about 15%±10% or trehalose at a concentration of from about 5% to about 15%±10%.

77—A pharmaceutical formulation at a pH of about 6.5±0.5 to 7.5±0.5 or 6.0±0.15 to 7.5±0.15 and including a GLP-1 or a GLP-1 analogue comprising or consisting of the amino acid sequence set forth in SEQ ID NO:3 at a concentration of from about 100 μg/ml to about 500 μg/ml, sodium phosphate at a concentration of from about 7.5 mM to about 12.5 mM±10% and glycerol at a concentration of from about 150 mM to about 300 mM±10%, mannitol at a concentration of from about 150 mM to about 300 mM±10% sucrose at a concentration of from about 5% to about 15%±10%, or trehalose at a concentration of from about 5% to about 15%±10%.

78—A pharmaceutical formulation at a pH of about 6.5±0.5 to 7.5±0.5 or 6.0±0.15 to 7.5±0.15 and including a GLP-1 or a GLP-1 analogue comprising or consisting of the amino acid sequence set forth in SEQ ID NO:3 at a concentration of from about 100 μg/ml to about 500 μg/ml, potassium phosphate at a concentration of from about 7.5 mM to about 12.5 mM±10% and glycerol at a concentration of from about 150 mM to about 300 mM±10%, mannitol at a concentration of from about 150 mM to about 300 mM±10%, sucrose at a concentration of from about 5% to about 15%±10% or trehalose at a concentration of from about 5% to about 15%±10%.

79—A pharmaceutical formulation at a pH of about 6.5±0.5 to 7.5±0.5 or 6.0±0.15 to 7.5±0.15 and including a GLP-1 or a GLP-1 analogue comprising or consisting of the amino acid sequence set forth in SEQ ID NO:3 at a concentration of from about 100 µg/ml to about 500 µg/ml, maleate at a concentration of from about 7.5 mM to about 12.5 mM±10% and glycerol at a concentration of from about 150 mM to about 300 mM±10%, mannitol at a concentration of from about 150 mM to about 300 mM±10%, sucrose at a concentration of from about 5% to about 15%±10% or trehalose at a concentration of from about 5% to about 15%±10%.

80—A pharmaceutical formulation at a pH of 6.5±0.5 to 7.5±0.5 (e.g., 6.5±0.15 to 7.0±0.15 etc.) and including a GLP-1 analogue comprising or consisting of the amino acid sequence set forth in SEQ ID NO:3 at a concentration of from about 100 µg/ml to about 500 µg/ml, sodium citrate at a concentration of about 10 mM±10%, a tonicity agent such as glycerol at a concentration of from about 165 mM to about 275 mM±10%, sucrose at a concentration of from about 5% to about 15%, trehalose at a concentration of from about 5% to about 15% or NaCl at a concentration of from about 50 mM to about 150 mM, a surfactant such as polysorbate at a concentration of about 0.005 to 0.05% (w/v)±10% and an amino acid excipient such as methionine at a concentration of about 5 mM to about 25 mM±10%, proline at a concentration of from about 25 mM to about 75 mM±10% or arginine at a concentration of from about 50 mM to about 150 mM±10%.

81—A pharmaceutical formulation at a pH of 6.5±0.5 to 7.5±0.5 (e.g., 6.5±0.15 to 7.0±0.15 etc.) and including a GLP-1 analogue comprising or consisting of the amino acid sequence set forth in SEQ ID NO:3 at a concentration of from about 100 µg/ml to about 500 µg/ml, histidine HCl at a concentration of about 10 mM±10%, a tonicity agent such as glycerol at a concentration of from about 165 mM to about 275 mM±10%, sucrose at a concentration of from about 5% to about 15%, trehalose at a concentration of from about 5% to about 15% or NaCl at a concentration of from about 50 mM to about 150 mM, a surfactant such as polysorbate at a concentration of about 0.005 to 0.05% (w/v)±10% and an amino acid excipient such as methionine at a concentration of about 5 mM to about 25 mM±10%, proline at a concentration of from about 25 mM to about 75 mM±10% or arginine at a concentration of from about 50 mM to about 150 mM±10%.

82—A pharmaceutical formulation at a pH of 6.5±0.5 to 7.5±0.5 (e.g., 6.5±0.15 to 7.0±0.15, etc.) and including a GLP-1 analogue comprising or consisting of the amino acid sequence set forth in SEQ ID NO:3 at a concentration of from about 100 µg/ml to about 500 µg/ml, maelate at a concentration of about 10 mM±10%, a tonicity agent such as glycerol at a concentration of from about 165 mM to about 275 mM±10%, sucrose at a concentration of from about 5% to about 15%, trehalose at a concentration of from about 5% to about 15% or NaCl at a concentration of from about 50 mM to about 150 mM, a surfactant such as polysorbate at a concentration of about 0.005 to 0.05% (wv)±10% and an amino acid excipient such as methionine at a concentration of about 5 mM to about 25 mM±10%, proline at a concentration of from about 25 mM to about 75 mM±10% or arginine at a concentration of from about 50 mM to about 150 mM±10%.

83—A pharmaceutical formulation at a pH of 6.5±0.5 to 7.5±0.5 (e.g., 6.5±0.15 to 7.0±0.15 etc.) and including a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, a tonicity agent such as glycerol at a concentration of from about 165 mM to about 275 mM±10%, sucrose at a concentration of from about 5% to about 15%, trehalose at a concentration of from about 5% to about 15% or NaCl at a concentration of from about 50 mM to about 150 mM, a surfactant such as polysorbate at a concentration of about 0.005 to 0.05% (w/v)±10% and an amino acid excipient such as methionine at a concentration of about 5 mM to about 25 mM±10%, proline at a concentration of from about 25 mM to about 75 mM±10% or arginine at a concentration of from about 50 mM to about 150 mM±10%.

84—A pharmaceutical formulation at a pH of 6.5±0.5 to 7.5±0.5 (e.g., 6.5±0.15 to 7.0±0.15, etc.) and including a GLP-1 analogue comprising or consisting of the amino acid sequence set forth in SEQ ID NO:3 at a concentration of from about 100 µg/ml to about 500 µg/ml, potassium phosphate at a concentration of about 10 mM±10%, a tonicity agent such as glycerol at a concentration of from about 165 mM to about 275 mM±10%, sucrose at a concentration of from about 5% to about 15%, trehalose at a concentration of from about 5% to about 15% or NaCl at a concentration of from about 50 mM to about 150 mM, a surfactant such as polysorbate at a concentration of about 0.005 to 0.05% (w/v)±10% and an amino acid excipient such as methionine at a concentration of about 5 mM to about 25 mM±10%, proline at a concentration of from about 25 mM to about 75 mM±10% or arginine at a concentration of from about 50 mM to about 150 mM±10%.

85—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, and mannitol at a concentration of about 165 mM to about 275 mM±10%, sucrose at a concentration of about 5% to about 15%±10% or trehalose at a concentration of about 5% to about 15%±10%.

86—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, mannitol at a concentration of about 165 mM to about 275 mM±10%, and polysorbate-20 at a concentration of about 0.01 to 0.03% (w/v)±10%.

87—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, mannitol at a concentration of about 165 mM±10%, and polysorbate-20 at a concentration of about 0.01 to 0.03% (w/v)±10%.

88—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, mannitol at a concentration of about 275 mM±10%, and polysorbate-20 at a concentration of about 0.01 to 0.03% (w/v)±10%.

89—A pharmaceutical formulation at a pH of about 6.5±0.5 to 7.5±0.5 (e.g., (e.g., 7.0±0.5, 7.0±0.15 etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, mannitol at a concentration of about 275 mM±10%, polysorbate-20 at a concentration of about 0.01 to 0.03% (w/v)±10% and methionine at a concentration of about 5 mM to about 25 mM±10%.

90—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, mannitol at a concentration of about 165 mM±10%, polysorbate-20 at a concentration of about 0.01 to 0.03% (w/v)±10% and methionine at a concentration of about 5 mM to about 25 mM±10%.

91—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, mannitol at a concentration of about 275 mM±10%, polysorbate-20 at a concentration of about 0.01 to 0.03% (w/v)±10% and proline at a concentration of about 25 mM to about 75 mM±10%.

92—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, mannitol at a concentration of about 165 mM±10%, polysorbate-20 at a concentration of about 0.01 to 0.03% (w/v)±10% and proline at a concentration of about 25 mM to about 75 mM±10%.

93—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, sucrose at a concentration of about 5% to about 15%±10%, and polysorbate-20 at a concentration of about 0.01 to 0.03% (w/v)±10%.

94—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, sucrose at a concentration of about 8%±10%, and polysorbate-20 at a concentration of about 0.01 to 0.03% (w/v)±10%.

95—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, sucrose at a concentration of about 10%±10%, and polysorbate-20 at a concentration of about 0.01 to 0.03% (w/v)±10%.

96—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, sucrose at a concentration of about 8%±10%, polysorbate-20 at a concentration of about 0.01 to 0.03% (w/v)±10% and methionine at a concentration of about 5 mM to about 25 mM±10%.

97—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, sucrose at a concentration of about 10%±10%, polysorbate-20 at a concentration of about 0.01 to 0.03% (w/v)±10% and methionine at a concentration of about 5 mM to about 25 mM±10%.

98—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, sucrose at a concentration of about 8%±10%, polysorbate-20 at a concentration of about 0.01 to 0.03% (w/v)±10% and proline at a concentration of about 25 mM to about 75 mM±10%.

99—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, sucrose at a concentration of about 10%±10%, polysorbate-20 at a concentration of about 0.01 to 0.03% (w/v)±10% and proline at a concentration of about 25 mM to about 75 mM±10%.

100—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, trehalose at a concentration of about 5% to about 15%±10%, and polysorbate-20 at a concentration of about 0.01 to 0.03% (w/v)±10%.

101—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, trehalose at a concentration of about 8%±10%, and polysorbate-20 at a concentration of about 0.01 to 0.03% (w/v)±10%.

102—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 µg/ml to about 500 µg/ml, histidine-HCl at a concentration of about 10 mM±10%, trehalose at a concentration of about 10%±10%, and polysorbate-20 at a concentration of about 0.01 to 0.03% (w/v)±10%.
103—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, trehalose at a concentration of about 8%±10%, polysorbate-20 at a concentration of about 0.01 to 0.03% (w/v)±10% and methionine at a concentration of about 5 mM to about 25 mM±10%.
104—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, trehalose at a concentration of about 10%±10%, polysorbate-20 at a concentration of about 0.01 to 0.03% (w/v)±10% and methionine at a concentration of about 5 mM to about 25 mM±10%.
105—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, trehalose at a concentration of about 8%±10%, polysorbate-20 at a concentration of about 0.01 to 0.03% (w/v)±10% and proline at a concentration of about 25 mM to about 75 mM±10%.
106—A pharmaceutical formulation at a pH of about 6.5±0.5 to 7.5±0.5 (e.g., 7.0±0.5, 7.0±0.15, etc.) and including a GLP-1 analogue comprising or consisting of the amino acid sequence set forth in SEQ ID NO:3 at a concentration of from about 100 μg/ml to about 500 μg/ml, histidine-HCl at a concentration of about 10 mM±10%, trehalose at a concentration of about 10%±10%, polysorbate-20 at a concentration of about 0.01 to 0.03% (w/v)±10% and proline at a concentration of about 25 mM to about 75 mM±10%.
107—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, and mannitol at a concentration of about 165 mM to about 275 mM±10% sucrose at a concentration of about 5% to about 15%±10% or trehalose at a concentration of about 5% to about 15%±10%.
108—A pharmaceutical formulation at a pH of about 6.5±0.5 to 7.5±0.5 (e.g., 7.0±0.5, 6.5±0.15, etc.(=) and including a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, mannitol at a concentration of about 165 mM to about 275 mM±10%, and polysorbate-20 at a concentration of about 0.01 to 0.03% (w/v)±10%.
109—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, mannitol at a concentration of about 165 mM±10%, and polysorbate-20 at a concentration of about 0.01 to 0.03% (w/v)±10%.
110—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, mannitol at a concentration of about about 275 mM±10%, and polysorbate-20 at a concentration of about 0.01 to 0.03% (w/v)±10%.
111—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, mannitol at a concentration of about 275 mM±10%, polysorbate-20 at a concentration of about 0.01 to 0.03% (w/v)±10% and methionine at a concentration of about 5 mM to about 25 mM±10%.
112—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, mannitol at a concentration of about 165 mM±10%, polysorbate-20 at a concentration of about 0.01 to 0.03% (w/v)±10% and methionine at a concentration of about 5 mM to about 25 mM±10%.
113—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, mannitol at a concentration of about 275 mM±10%, polysorbate-20 at a concentration of about 0.01 to 0.03% (w/v)±10% and proline at a concentration of about 25 mM to about 75 mM±10%.
114—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, mannitol at a concentration of about 165 mM±10%, polysorbate-20 at a concentration of about 0.01 to 0.03% (w/v)±10% and proline at a concentration of about 25 mM to about 75 mM±10%.
115—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, sucrose at a concentration of about 5% to about 15%±10%, and polysorbate-20 at a concentration of about 0.01 to 0.03% (w/v)±10%.
116—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 μg/ml to about 500 μg/ml, sodium phosphate at a concentration of about 10 mM±10%, sucrose at a concentration of about 8%±10%, and polysorbate-20 at a concentration of about 0.01 to 0.03% (w/v)±10%.
117—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, sucrose at a concentration of about 10%±10%, and polysorbate-20 at a concentration of about 0.01 to 0.03% (w/v)±10%.
118—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, sucrose at a concentration of about 8%±10%, polysorbate-20 at a concentration of about 0.01 to 0.03% (w/v)±10% and methionine at a concentration of about 5 mM to about 25 mM±10%.
119—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, sucrose at a concentration of about 10%±10%, polysorbate-20 at a concentration of about 0.01 to 0.03% (w/v)±10% and methionine at a concentration of about 5 mM to about 25 mM±10%.
120—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, sucrose at a concentration of about 8%±10%, polysorbate-20 at a concentration of about 0.01 to 0.03% (w/v)±10% and proline at a concentration of about 25 mM to about 75 mM±10%.
121—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, sucrose at a concentration of about 10%±10%, polysorbate-20 at a concentration of about 0.01 to 0.03% (w/v)±10% and proline at a concentration of about 25 mM to about 75 mM±10%.
122—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, trehalose at a concentration of about 5% to about 15%±10%, and polysorbate-20 at a concentration of about 0.01 to 0.03% (w/v)±10%.
123—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, trehalose at a concentration of about 8%±10%, and polysorbate-20 at a concentration of about 0.01 to 0.03% (w/v)±10%.
124—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, trehalose at a concentration of about 10%±10%, and polysorbate-20 at a concentration of about 0.01 to 0.03% (w/v)±10%.
125—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, trehalose at a concentration of about 8%±10%, polysorbate-20 at a concentration of about 0.01 to 0.03% (w/v)±10% and methionine at a concentration of about 5 mM to about 25 mM±10%.
126—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, trehalose at a concentration of about 10%±10%, polysorbate-20 at a concentration of about 0.01 to 0.03% (w/v)±10% and methionine at a concentration of about 5 mM to about 25 mM±10%.
127—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, trehalose at a concentration of about 8%±10%, polysorbate-20 at a concentration of about 0.01 to 0.03% (w/v)±10% and proline at a concentration of about 25 mM to about 75 mM±10%.
128—A pharmaceutical formulation at a pH of about 6.5±0.5 to 7.5±0.5 (e.g., 7.0±0.5, 6.5±0.15, etc.) and including a GLP-1 analogue comprising or consisting of the amino acid sequence set forth in SEQ ID NO:3 at a concentration of from about 100 µg/ml to about 500 µg/ml, sodium phosphate at a concentration of about 10 mM±10%, trehalose at a concentration of about 10%±10%, polysorbate-20 at a concentration of about 0.01 to 0.03% (w/v)±10% and proline at a concentration of about 25 mM to about 75 mM±10%.
129—The pharmaceutical formulation of any one of the preceding embodiments wherein the formulation is isotonic with blood and/or serum.
130—The pharmaceutical formulation of any one of the preceding embodiments wherein the peptide concentration is ±20% the initial concentration (at preparation) after one or more stress conditions.
131—The pharmaceutical formulation of any one of the preceding embodiments wherein the formulation has a low concentration of subvisible particles.
132—The pharmaceutical formulation of any one of the preceding embodiments wherein the concentration of subvisible particles (cumulative particle counts) as measured by micro-flow imaging is 1000 or below for particles ≥2 µm, 275 or below for particles ≥5 µm, 100 or below for particles ≥10 μm and/or 30 or below for particles ≥25 μm at T−1m_25° C. and/or T−1m_40° C.

133—The pharmaceutical formulation of any one of the preceding embodiments wherein the concentration of subvisible particles (cumulative particle counts) as measured by micro-flow imaging is 500 or below for particles ≥2 μm, 200 or below for particles ≥5 μm, 50 or below for particles ≥10 μm and/or 10 or below for particles ≥25 μm at T−3m_5° C. and/or T−3m_25° C.

134—The pharmaceutical formulation of any one of the preceding embodiments wherein the monomer content as measured by HP-SEC is 95% or higher at T−1m_5° C., 95% or higher at T−1m_25° C., 92% or higher at T−1m_40° C., 95% or higher at T−3m_5° C., 95% or higher at T−3m_25° C., and/or 92% or higher at T−3m_40° C.

135—The pharmaceutical formulation of any one of the preceding embodiments wherein the monomer content as measured by HP-SEC is at least 92%, at least 93%, at least 94% or at least 95% or higher under one or more stress conditions.

136—The pharmaceutical formulation of any one of the preceding embodiments wherein the aggregate content as measured by HP-SEC is 5% or less, 4% or less, 3% or less. 2% or less, 1% or less at T−1m_5° C., T−1m_25° C., T−3m_5° C. and/or T−3m_25° C.

137—The pharmaceutical formulation of any one of the preceding embodiments wherein the aggregate content as measured by HP-SEC is 5% or less, 4% or less, 3% or less. 2% or less, 1% or less under one or more stress conditions.

138—The pharmaceutical formulation of any one of the preceding embodiments provided in a single-dose or multi-dose container.

139—The pharmaceutical formulation of any one of the preceding embodiments, in a unit-dose vial, multi-dose vial, cartridge or pre-filled syringe.

140—The pharmaceutical formulation of any one of the preceding embodiments in a unit-dose vial, multi-dose vial, cartridge or pre-filled syringe that includes, for example, from about 20 μg to about 1 mg of the GLP-1 or GLP-1 analogue or ROSE-010.

141—The pharmaceutical formulation of any one of the preceding embodiments, in a unit-dose vial, multi-dose vial, cartridge or pre-filled syringe that includes for example, a dose of at least 150 μg of the GLP-1 or GLP-1 analogue or ROSE-010.

142—The pharmaceutical formulation of any one of the preceding embodiments wherein sodium acetate is used at a concentration of 10 mM.

143—The pharmaceutical formulation of any one of the preceding embodiments wherein sodium citrate is used at a concentration of 10 mM.

144—The pharmaceutical formulation of any one of the preceding embodiments wherein Histidine-HCl is used at a concentration of 10 mM.

145—The pharmaceutical formulation of any one of the preceding embodiments wherein sodium maleate is used at a concentration of 10 mM.

146—The pharmaceutical formulation of any one of the preceding embodiments wherein sodium phosphate is used at a concentration of 10 mM.

147—The pharmaceutical formulation of any one of the preceding embodiments wherein glycerol is used at a concentration of 165 mM.

148—The pharmaceutical formulation of any one of the preceding embodiments wherein glycerol is used at a concentration of 275 mM.

149—The pharmaceutical formulation of any one of the preceding embodiments wherein mannitol is used at a concentration of 3%.

150—The pharmaceutical formulation of any one of the preceding embodiments wherein mannitol is used at a concentration of 5%.

151—The pharmaceutical formulation of any one of the preceding embodiments wherein NaCl is used at a concentration of 50 mM.

152—The pharmaceutical formulation of any one of the preceding embodiments wherein NaCl is used at a concentration of 130 mM.

153—The pharmaceutical formulation of any one of the preceding embodiments wherein NaCl is used at a concentration of 150 mM.

154—The pharmaceutical formulation of any one of the preceding embodiments wherein sucrose is used at a concentration of 5%.

155—The pharmaceutical formulation of any one of the preceding embodiments wherein sucrose is used at a concentration of 8%.

156—The pharmaceutical formulation of any one of the preceding embodiments wherein sucrose is used at a concentration of 10%.

157—The pharmaceutical formulation of any one of the preceding embodiments wherein trehalose is used at a concentration of 5%.

158—The pharmaceutical formulation of any one of the preceding embodiments wherein trehalose is used at a concentration of 8%.

159—The pharmaceutical formulation of any one of the preceding embodiments wherein trehalose is used at a concentration of 10%.

160—The pharmaceutical formulation of any one of the preceding embodiments wherein arginine-HCl is used at a concentration of 50 mM.

161—The pharmaceutical formulation of any one of the preceding embodiments wherein arginine-HCl is used at a concentration of 100 mM.

162—The pharmaceutical formulation of any one of the preceding embodiments wherein methionine is used at a concentration of 5 mM.

163—The pharmaceutical formulation of any one of the preceding embodiments wherein methionine is used at a concentration of 10 mM.

164—The pharmaceutical formulation of any one of the preceding embodiments wherein methionine is used at a concentration of 15 mM.

165—The pharmaceutical formulation of any one of the preceding embodiments wherein proline is used at a concentration of 25 mM.

166—The pharmaceutical formulation of any one of the preceding embodiments wherein proline is used at a concentration of 50 mM.

167—The pharmaceutical formulation of any one of the preceding embodiments wherein proline is used at a concentration of 75 mM.

168—The pharmaceutical formulation of any one of the preceding embodiments wherein the polysorbate is polysorbate-20 at a concentration of 0.005% (w/v).

169—The pharmaceutical formulation of any one of the preceding embodiments wherein the polysorbate is polysorbate-20 at a concentration of 0.02% (w/v).

170—The pharmaceutical formulation of any one of the preceding embodiments wherein the polysorbate is polysorbate-20 at a concentration of 0.05% (w/v).

171—The pharmaceutical formulation of any one of the preceding embodiments wherein the polysorbate is polysorbate-60 at a concentration of 0.005% (w/v).

172—The pharmaceutical formulation of any one of the preceding embodiments wherein the polysorbate is polysorbate-60 at a concentration of 0.02% (w/v).

173—The pharmaceutical formulation of any one of the preceding embodiments wherein the polysorbate is polysorbate-60 at a concentration of 0.05% (w/v).

174—The pharmaceutical formulation of any one of the preceding embodiments wherein the polysorbate is polysorbate-80 at a concentration of 0.005% (w/v).

175—The pharmaceutical formulation of any one of the preceding embodiments wherein the polysorbate is polysorbate-80 at a concentration of 0.02% (w/v).

176—The pharmaceutical formulation of any one of the preceding embodiments wherein the polysorbate is polysorbate-80 at a concentration of 0.05% (w/v).

177—The pharmaceutical formulation of any one of the preceding embodiments wherein the formulation is at pH 6.5.

178—The pharmaceutical formulation of any one of the preceding embodiments wherein the formulation is at pH 6.6.

179—The pharmaceutical formulation of any one of the preceding embodiments wherein the formulation is at pH 6.7.

180—The pharmaceutical formulation of any one of the preceding embodiments wherein the formulation is at pH 6.8.

181—The pharmaceutical formulation of any one of the preceding embodiments wherein the formulation is at pH 6.9.

182—The pharmaceutical formulation of any one of the preceding embodiments wherein the formulation is at pH 7.0.

183—The pharmaceutical formulation of any one of the preceding embodiments, wherein the GLP-1 or analogue thereof comprises or consists of the amino acid sequence set forth in SEQ ID NO:3 at a concentration of 300 µg/ml±20%.

184—The pharmaceutical formulation of any one of the preceding embodiments, wherein the GLP-1 or analogue thereof comprises or consists of the amino acid sequence set forth in SEQ ID NO:3 at a concentration of 300 µg/ml±10%.

185—The pharmaceutical formulation of any one of the preceding embodiments, wherein the pharmaceutical formulation is liquid.

186—The pharmaceutical formulation of any one of the preceding embodiments, wherein the pharmaceutical formulation is stable.

187—A pre-filled syringe comprising the pharmaceutical formulation of any one of the preceding embodiments.

188—A pre-filled syringe comprising the pharmaceutical formulation of any one of the preceding embodiments that comprises from about 20 µg to about 1 mg of the GLP-1 or GLP-1 analogue or ROSE-010.

189—A pre-filled syringe comprising the pharmaceutical formulation of any one of the preceding embodiments that comprises a dose of at least 150 µg of the GLP-1 or GLP-1 analogue or ROSE-010.

190—A pre-filled syringe comprising the pharmaceutical formulation of any one of the preceding embodiments, wherein the GLP-1 or GLP-1 analogue or ROSE-010 thereof is at a concentration of 300 µg/ml±10%.

191—A method of treating a disorder or condition in which administration of a GLP-1 or GLP-1 analogue or ROSE-010 is indicated, that comprises administering the pharmaceutical formulation of any one of the preceding embodiments to an individual in need.

192—A method of treating irritable bowel syndrome (IBS) that comprises administering the pharmaceutical formulation of any one of the preceding embodiments to an individual in need.

193—A method of treating constipation predominant IBS (IBS-C) that comprises administering the pharmaceutical formulation of any one of the preceding embodiments to an individual in need.

194—A method of treating diarrhea predominant IBS (IBS-D) that comprises administering the pharmaceutical formulation of any one of the preceding embodiments to an individual in need.

195—A method of treating mixed or alternating type IBS (IBS-M) that comprises administering the pharmaceutical formulation of any one of the preceding embodiments to an individual in need.

196—A method of treating diabetes, ischemia, reperfused tissue injury, dyslipidemia, diabetic cardiomyopathy, myocardial infarction, acute coronary syndrome, obesity, catabolic changes after surgery, hyperglycemia, irritable bowel syndrome, stroke, neurodegenerative disorders, memory and learning disorders, islet cell transplant functional dyspepsia and/or regenerative therapy that comprises administering the pharmaceutical formulation of any one of the preceding embodiments to an individual in need.

197—The method of any one of the preceding embodiments, wherein the pharmaceutical formulation is administered subcutaneously.

198—The method of any one of the preceding embodiments, wherein the GLP-1 or GLP-1 analogue or ROSE-010 is administered at a dose of about 20 µg to about 1 mg.

199—The method of any one of the preceding embodiments, wherein the GLP-1 or GLP-1 analogue or ROSE-010 is administered at a dose of about 30 µg to about 300 µg daily.

200—The method of any one of the preceding embodiments, wherein the GLP-1 or GLP-1 analogue or ROSE-010 is administered at a dose of about 50 µg.

201—The method of any one of the preceding embodiments, wherein the GLP-1 or GLP-1 analogue or ROSE-010 is administered at a dose of about 100 µg.

202—The method of any one of the preceding embodiments, wherein the GLP-1 or GLP-1 analogue or ROSE-010 is administered at a dose of about 150 µg.

203—The method of any one of the preceding embodiments, wherein the GLP-1 or GLP-1 analogue or ROSE-010 is administered at a dose of about 200 µg.

204—The method of any one of the preceding embodiments, wherein the GLP-1 or GLP-1 analogue or ROSE-010 is administered at a dose of about 300 µg.

205—The method of any one of the preceding embodiments, wherein the GLP-1 or GLP-1 analogue or ROSE-010 is administered at a dose of about 400 µg.

206—The method of any one of the preceding embodiments, wherein the GLP-1 or GLP-1 analogue or ROSE-010 is administered at a dose of about 500 µg.

207—The method of any one of the preceding embodiments, wherein the pharmaceutical formulation is administered during acute pain associated with IBS.

208—The method of any one of the preceding embodiments, wherein the pharmaceutical formulation is administered during acute pain associated with IBS-C, IBS-D or IBS-M.

209—The pharmaceutical formulation of any one of the preceding embodiments for use in a method of treatment of any one of the preceding embodiments.

The following examples are provided to further illustrate aspects and embodiments of the disclosure. These examples are non-limiting and should not be construed as limiting any aspects and embodiments of the disclosure.

EXAMPLES

Example 1: Peptide Material, Formulations and Methods

The solid ROSE-010 acetate salt (net peptide content of 88.12%; purity (HPLC) of 96.1%) is aliquoted into 200 mg aliquots and stored at −20° C. Aliquots used in experimentations re thawed at room temperature.

Stock solutions of each component (buffer, tonicity agent, excipient and/or surfactant etc.) are prepared, filtered and are either used immediately or stored at room temperature or between 2-8° C.

Stock formulations at 1 mg/ml are prepared by using concentrated peptide solution spiked in water or into stock solutions of buffer, excipients and/or tonicity agent and filled up with water. If needed, solubility of the ROSE-010 (acetate salt) may be increased by the addition of an acid such as HCl. If needed, the pH of the samples is adjusted.

The peptide concentration is confirmed by UV spectroscopy ($\lambda$=280 nm). The final peptide concentration in the formulations tested is set at 300 µg/ml (Table 4). Corresponding placebo formulations (without peptide) are made by using the same buffer, excipients and/or tonicity agents.

The samples are filtered under laminar air-flow (LAF), by using a 0.22-µm syringe PVDF filter unit. Subsequently, 1.5 ml of the filtered formulations are filled into washed and sterilized 2R glass vials.

The following reagents (USP or Ph. Eur. grade) are used:

| Name |
| --- |
| L-Histidine Hydrochloride Monohydrate |
| L-Histidine |
| D-Mannitol |
| L-Methionine |
| Tween ® 20 (Polysorbate) NF, Multi-compendial |
| Sodium acetate, Trihydrate |
| Tri-Sodium citrate, Dihydrate |
| Sodium dihydrogen phosphate, Dihydrate |
| Di-sodium hydrogen phosphate, Dihydrate |
| NaCl, |
| D-Sucrose |
| D-Trehalose, Dihydrate |
| L-Arginine |
| L-Proline |
| Glycerol |

Several formulations are tested to determine the effect of pH, buffering agents, tonicity agents, excipients and surfactant on the stability of ROSE-010 peptide. Representative formulations are illustrated in Tables 1A-1E and Table 4. It is to be understood herein that in Tables 1A-1D and Table 4, the pH is provided for illustrative purposes only and may vary without affecting the stability of the formulation. For example, formulations containing histidine-HCl or sodium phosphate may have a pH ranging from 6.5±0.5 to 7.5±0.5, including for example, a pH ranging from 6.5±0.5 to 7.0±0.5, a pH of 6.5±0.5, a pH of 7.0±0.5, a pH of 7.5±0.5 etc. Table 1A—List of histidine buffer-based formulations

| pH | Buffer | Tonicity agent | Excipient | Surfactant |
| --- | --- | --- | --- | --- |
| 6.5 ± 0.15 | 10 mM histidine - HCl | 5% sucrose | — | 0.02% (w/v) PS20 |
| 6.5 ± 0.15 | 10 mM histidine - HCl | 5% sucrose | 10 mM methionine | 0.02% (w/v) PS20 |
| 6.5 ± 0.15 | 10 mM histidine - HCl | 5% sucrose | 50 mM proline | 0.02% (w/v) PS20 |
| 6.5 ± 0.15 | 10 mM histidine - HCl | 8% sucrose | — | 0.02% (w/v) PS20 |
| 6.5 ± 0.15 | 10 mM histidine - HCl | 8% sucrose | 10 mM methionine | 0.02% (w/v) PS20 |
| 6.5 ± 0.15 | 10 mM histidine - HCl | 8% sucrose | 50 mM proline | 0.02% (w/v) PS20 |
| 6.5 ± 0.15 | 10 mM histidine - HCl | 10% sucrose | — | 0.02% (w/v) PS20 |
| 6.5 ± 0.15 | 10 mM histidine - HCl | 10% sucrose | 10 mM methionine | 0.02% (w/v) PS20 |
| 6.5 ± 0.15 | 10 mM histidine - HCl | 10% sucrose | 50 mM proline | 0.02% (w/v) PS20 |
| 6.5 ± 0.15 | 10 mM histidine - HCl | 165 mM mannitol | — | 0.02% (w/v) PS20 |
| 6.5 ± 0.15 | 10 mM histidine - HCl | 165 mM mannitol | 10 mM methionine | 0.02% (w/v) PS20 |
| 6.5 ± 0.15 | 10 mM histidine - HCl | 165 mM mannitol | 50 mM proline | 0.02% (w/v) PS20 |
| 6.5 ± 0.15 | 10 mM histidine - HCl | 275 mM mannitol | — | 0.02% (w/v) PS20 |
| 6.5 ± 0.15 | 10 mM histidine - HCl | 275 mM mannitol | 10 mM methionine | 0.02% (w/v) PS20 |
| 6.5 ± 0.15 | 10 mM histidine - HCl | 275 mM mannitol | 50 mM proline | 0.02% (w/v) PS20 |
| 7.0 ± 0.15 | 10 mM histidine - HCl | 5% sucrose | — | 0.02% (w/v) PS20 |
| 7.0 ± 0.15 | 10 mM histidine - HCl | 5% sucrose | 10 mM methionine | 0.02% (w/v) PS20 |
| 7.0 ± 0.15 | 10 mM histidine - HCl | 5% sucrose | 50 mM proline | 0.02% (w/v) PS20 |
| 7.0 ± 0.15 | 10 mM histidine - HCl | 8% sucrose | — | 0.02% (w/v) PS20 |
| 7.0 ± 0.15 | 10 mM histidine - HCl | 8% sucrose | 5 mM methionine | 0.005% (w/v) PS20 |
| 7.0 ± 0.15 | 10 mM histidine - HCl | 8% sucrose | 10 mM methionine | 0.005% (w/v) PS20 |
| 7.0 ± 0.15 | 10 mM histidine - HCl | 8% sucrose | 15 mM methionine | 0.005% (w/v) PS20 |

-continued

| pH | Buffer | Tonicity agent | Excipient | Surfactant |
|---|---|---|---|---|
| 7.0 ± 0.15 | 10 mM histidine - HCl | 8% sucrose | 5 mM methionine | 0.02% (w/v) PS20 |
| 7.0 ± 0.15 | 10 mM histidine - HCl | 8% sucrose | 10 mM methionine | 0.02% (w/v) PS20 |
| 7.0 ± 0.15 | 10 mM histidine - HCl | 8% sucrose | 15 mM methionine | 0.02% (w/v) PS20 |
| 7.0 ± 0.15 | 10 mM histidine - HCl | 8% sucrose | 5 mM methionine | 0.05% (w/v) PS20 |
| 7.0 ± 0.15 | 10 mM histidine - HCl | 8% sucrose | 10 mM methionine | 0.05% (w/v) PS20 |
| 7.0 ± 0.15 | 10 mM histidine - HCl | 8% sucrose | 15 mM methionine | 0.05% (w/v) PS20 |
| 7.0 ± 0.15 | 10 mM histidine - HCl | 8% sucrose | 15 mM methionine | 0.02% (w/v) PS20 |
| 7.0 ± 0.15 | 10 mM histidine - HCl | 8% sucrose | 25 mM proline | 0.005% (w/v) PS20 |
| 7.0 ± 0.15 | 10 mM histidine - HCl | 8% sucrose | 50 mM proline | 0.005% (w/v) PS20 |
| 7.0 ± 0.15 | 10 mM histidine - HCl | 8% sucrose | 75 mM proline | 0.005% (w/v) PS20 |
| 7.0 ± 0.15 | 10 mM histidine - HCl | 8% sucrose | 25 mM proline | 0.02% (w/v) PS20 |
| 7.0 ± 0.15 | 10 mM histidine - HCl | 8% sucrose | 50 mM proline | 0.02% (w/v) PS20 |
| 7.0 ± 0.15 | 10 mM histidine - HCl | 8% sucrose | 75 mM proline | 0.02% (w/v) PS20 |
| 7.0 ± 0.15 | 10 mM histidine - HCl | 8% sucrose | 25 mM proline | 0.05% (w/v) PS20 |
| 7.0 ± 0.15 | 10 mM histidine - HCl | 8% sucrose | 50 mM proline | 0.05% (w/v) PS20 |
| 7.0 ± 0.15 | 10 mM histidine - HCl | 8% sucrose | 75 mM proline | 0.05% (w/v) PS20 |
| 7.0 ± 0.15 | 10 mM histidine - HCl | 10% sucrose | — | 0.02% (w/v) PS20 |
| 7.0 ± 0.15 | 10 mM histidine - HCl | 10% sucrose | 5 mM methionine | 0.005% (w/v) PS20 |
| 7.0 ± 0.15 | 10 mM histidine - HCl | 10% sucrose | 10 mM methionine | 0.005% (w/v) PS20 |
| 7.0 ± 0.15 | 10 mM histidine - HCl | 10% sucrose | 15 mM methionine | 0.005% (w/v) PS20 |
| 7.0 ± 0.15 | 10 mM histidine - HCl | 10% sucrose | 5 mM methionine | 0.02% (w/v) PS20 |
| 7.0 ± 0.15 | 10 mM histidine - HCl | 10% sucrose | 10 mM methionine | 0.02% (w/v) PS20 |
| 7.0 ± 0.15 | 10 mM histidine - HCl | 10% sucrose | 15 mM methionine | 0.02% (w/v) PS20 |
| 7.0 ± 0.15 | 10 mM histidine - HCl | 10% sucrose | 5 mM methionine | 0.05% (w/v) PS20 |
| 7.0 ± 0.15 | 10 mM histidine - HCl | 10% sucrose | 10 mM methionine | 0.05% (w/v) PS20 |
| 7.0 ± 0.15 | 10 mM histidine - HCl | 10% sucrose | 15 mM methionine | 0.05% (w/v) PS20 |
| 7.0 ± 0.15 | 10 mM histidine - HCl | 10% sucrose | 25 mM proline | 0.005% (w/v) PS20 |
| 7.0 ± 0.15 | 10 mM histidine - HCl | 10% sucrose | 50 mM proline | 0.005% (w/v) PS20 |
| 7.0 ± 0.15 | 10 mM histidine - HCl | 10% sucrose | 75 mM proline | 0.005% (w/v) PS20 |
| 7.0 ± 0.15 | 10 mM histidine - HCl | 10% sucrose | 25 mM proline | 0.02% (w/v) PS20 |
| 7.0 ± 0.15 | 10 mM histidine - HCl | 10% sucrose | 50 mM proline | 0.02% (w/v) PS20 |
| 7.0 ± 0.15 | 10 mM histidine - HCl | 10% sucrose | 75 mM proline | 0.02% (w/v) PS20 |
| 7.0 ± 0.15 | 10 mM histidine - HCl | 10% sucrose | 25 mM proline | 0.05% (w/v) PS20 |
| 7.0 ± 0.15 | 10 mM histidine - HCl | 10% sucrose | 50 mM proline | 0.05% (w/v) PS20 |
| 7.0 ± 0.15 | 10 mM histidine - HCl | 10% sucrose | 75 mM proline | 0.05% (w/v) PS20 |
| 7.0 ± 0.15 | 10 mM histidine - HCl | 165 mM mannitol | — | 0.005% (w/v) PS20 |
| 7.0 ± 0.15 | 10 mM histidine - HCl | 165 mM mannitol (3% (w/v)) | — | 0.02% (w/v) PS20 |
| 7.0 ± 0.15 | 10 mM histidine - HCl | 165 mM mannitol (3% (w/v)) | — | 0.05% (w/v) PS20 |
| 7.0 ± 0.15 | 10 mM histidine - HCl | 165 mM mannitol (3% (w/v)) | 5 mM methionine | 0.005% (w/v) PS20 |
| 7.0 ± 0.15 | 10 mM histidine - HCl | 165 mM mannitol (3% (w/v)) | 10 mM methionine | 0.005% (w/v) PS20 |
| 7.0 ± 0.15 | 10 mM histidine - HCl | 165 mM mannitol (3% (w/v)) | 15 mM methionine | 0.005% (w/v) PS20 |
| 7.0 ± 0.15 | 10 mM histidine - HCl | 165 mM mannitol (3% (w/v)) | 5 mM methionine | 0.02% (w/v) PS20 |
| 7.0 ± 0.15 | 10 mM histidine - HCl | 165 mM mannitol (3% (w/v)) | 10 mM methionine | 0.02% (w/v) PS20 |
| 7.0 ± 0.15 | 10 mM histidine - HCl | 165 mM mannitol (3% (w/v)) | 15 mM methionine | 0.02% (w/v) PS20 |
| 7.0 ± 0.15 | 10 mM histidine - HCl | 165 mM mannitol (3% (w/v)) | 5 mM methionine | 0.05% (w/v) PS20 |
| 7.0 ± 0.15 | 10 mM histidine - HCl | 165 mM mannitol (3% (w/v)) | 10 mM methionine | 0.05% (w/v) PS20 |
| 7.0 ± 0.15 | 10 mM histidine - HCl | 165 mM mannitol (3% (w/v)) | 15 mM methionine | 0.05% (w/v) PS20 |
| 7.0 ± 0.15 | 10 mM histidine - HCl | 165 mM mannitol (3% (w/v)) | 25 mM proline | 0.005% (w/v) PS20 |

-continued

| pH | Buffer | Tonicity agent | Excipient | Surfactant |
|---|---|---|---|---|
| 7.0 ± 0.15 | 10 mM histidine - HCl | 165 mM mannitol (3% (w/v)) | 50 mM proline | 0.005% (w/v) PS20 |
| 7.0 ± 0.15 | 10 mM histidine - HCl | 165 mM mannitol (3% (w/v)) | 75 mM proline | 0.005% (w/v) PS20 |
| 7.0 ± 0.15 | 10 mM histidine - HCl | 165 mM mannitol (3% (w/v)) | 25 mM proline | 0.02% (w/v) PS20 |
| 7.0 ± 0.15 | 10 mM histidine - HCl | 165 mM mannitol (3% (w/v)) | 50 mM proline | 0.02% (w/v) PS20 |
| 7.0 ± 0.15 | 10 mM histidine - HCl | 165 mM mannitol (3% (w/v)) | 75 mM proline | 0.02% (w/v) PS20 |
| 7.0 ± 0.15 | 10 mM histidine - HCl | 165 mM mannitol (3% (w/v)) | 25 mM proline | 0.05% (w/v) PS20 |
| 7.0 ± 0.15 | 10 mM histidine - HCl | 165 mM mannitol (3% (w/v)) | 50 mM proline | 0.05% (w/v) PS20 |
| 7.0 ± 0.15 | 10 mM histidine - HCl | 165 mM mannitol (3% (w/v)) | 75 mM proline | 0.05% (w/v) PS20 |
| 7.0 ± 0.15 | 10 mM histidine - HCl | 275 mM mannitol (5% (w/v)) | — | — |
| 7.0 ± 0.15 | 10 mM histidine - HCl | 275 mM mannitol (5% (w/v)) | — | 0.005% (w/v) PS20 |
| 7.0 ± 0.15 | 10 mM histidine - HCl | 275 mM mannitol (5% (w/v)) | — | 0.02% (w/v) PS20 |
| 7.0 ± 0.15 | 10 mM histidine - HCl | 275 mM mannitol (5% (w/v)) | — | 0.05% (w/v) PS20 |
| 7.0 ± 0.15 | 10 mM histidine - HCl | 275 mM mannitol (5% (w/v)) | 5 mM methionine | 0.005% (w/v) PS20 |
| 7.0 ± 0.15 | 10 mM histidine - HCl | 275 mM mannitol (5% (w/v)) | 10 mM methionine | 0.005% (w/v) PS20 |
| 7.0 ± 0.15 | 10 mM histidine - HCl | 275 mM mannitol (5% (w/v)) | 15 mM methionine | 0.005% (w/v) PS20 |
| 7.0 ± 0.15 | 10 mM histidine - HCl | 275 mM mannitol (5% (w/v)) | 5 mM methionine | 0.02% (w/v) PS20 |
| 7.0 ± 0.15 | 10 mM histidine - HCl | 275 mM mannitol (5% (w/v)) | 10 mM methionine | 0.02% (w/v) PS20 |
| 7.0 ± 0.15 | 10 mM histidine - HCl | 275 mM mannitol (5% (w/v)) | 15 mM methionine | 0.02% (w/v) PS20 |
| 7.0 ± 0.15 | 10 mM histidine - HCl | 275 mM mannitol (5% (w/v)) | 5 mM methionine | 0.05% (w/v) PS20 |
| 7.0 ± 0.15 | 10 mM histidine - HCl | 275 mM mannitol (5% (w/v)) | 10 mM methionine | 0.05% (w/v) PS20 |
| 7.0 ± 0.15 | 10 mM histidine - HCl | 275 mM mannitol (5% (w/v)) | 15 mM methionine | 0.05% (w/v) PS20 |
| 7.0 ± 0.15 | 10 mM histidine - HCl | 275 mM mannitol (5% (w/v)) | 25 mM proline | 0.005% (w/v) PS20 |
| 7.0 ± 0.15 | 10 mM histidine - HCl | 275 mM mannitol (5% (w/v)) | 50 mM proline | 0.005% (w/v) PS20 |
| 7.0 ± 0.15 | 10 mM histidine - HCl | 275 mM mannitol (5% (w/v)) | 75 mM proline | 0.005% (w/v) PS20 |
| 7.0 ± 0.15 | 10 mM histidine - HCl | 275 mM mannitol (5% (w/v)) | 25 mM proline | 0.02% (w/v) PS20 |
| 7.0 ± 0.15 | 10 mM histidine - HCl | 275 mM mannitol (5% (w/v)) | 50 mM proline | 0.02% (w/v) PS20 |
| 7.0 ± 0.15 | 10 mM histidine - HCl | 275 mM mannitol (5% (w/v)) | 75 mM proline | 0.02% (w/v) PS20 |
| 7.0 ± 0.15 | 10 mM histidine - HCl | 275 mM mannitol (5% (w/v)) | 25 mM proline | 0.05% (w/v) PS20 |
| 7.0 ± 0.15 | 10 mM histidine - HCl | 275 mM mannitol (5% (w/v)) | 50 mM proline | 0.05% (w/v) PS20 |
| 7.0 ± 0.15 | 10 mM histidine - HCl | 275 mM mannitol (5% (w/v)) | 75 mM proline | 0.05% (w/v) PS20 |

TABLE 1B

List of histidine buffer-based formulations

| pH | Buffer | Tonicity agent | Excipient | Surfactant |
|---|---|---|---|---|
| 6.5 ± 0.15 | 10 mM histidine-HCl | 5% trehalose | — | 0.02% (w/v) PS20 |
| 6.5 ± 0.15 | 10 mM histidine-HCl | 5% trehalose | 10 mM methionine | 0.02% (w/v) PS20 |
| 6.5 ± 0.15 | 10 mM histidine-HCl | 5% trehalose | 50 mM proline | 0.02% (w/v) PS20 |
| 6.5 ± 0.15 | 10 mM histidine-HCl | 5% trehalose | 50 mM arginine-HCl | 0.02% (w/v) PS20 |

TABLE 1B-continued

List of histidine buffer-based formulations

| pH | Buffer | Tonicity agent | Excipient | Surfactant |
|---|---|---|---|---|
| 6.5 ± 0.15 | 10 mM histidine-HCl | 8% trehalose | — | 0.02% (w/v) PS20 |
| 6.5 ± 0.15 | 10 mM histidine-HCl | 8% trehalose | 10 mM methionine | 0.02% (w/v) PS20 |
| 6.5 ± 0.15 | 10 mM histidine-HCl | 8% trehalose | 50 mM proline | 0.02% (w/v) PS20 |
| 6.5 ± 0.15 | 10 mM histidine-HCl | 8% trehalose | 50 mM arginine-HCl | 0.02% (w/v) PS20 |
| 6.5 ± 0.15 | 10 mM histidine-HCl | 10% trehalose | — | — |
| 6.5 ± 0.15 | 10 mM histidine-HCl | 10% trehalose | — | 0.02% (w/v) PS20 |
| 6.5 ± 0.15 | 10 mM histidine-HCl | 10% trehalose | 10 mM methionine | 0.02% (w/v) PS20 |
| 6.5 ± 0.15 | 10 mM histidine-HCl | 10% trehalose | 50 mM proline | 0.02% (w/v) PS20 |
| 6.5 ± 0.15 | 10 mM histidine-HCl | 10% trehalose | 50 mM arginine-HCl | 0.02% (w/v) PS20 |
| 6.5 ± 0.15 | 10 mM histidine-HCl | 165 mM glycerol | — | 0.02% (w/v) PS20 |
| 6.5 ± 0.15 | 10 mM histidine-HCl | 165 mM glycerol | 10 mM methionine | 0.02% (w/v) PS20 |
| 6.5 ± 0.15 | 10 mM histidine-HCl | 165 mM glycerol | 50 mM proline | 0.02% (w/v) PS20 |
| 6.5 ± 0.15 | 10 mM histidine-HCl | 165 mM glycerol | 50 mM arginine-HCl | 0.02% (w/v) PS20 |
| 6.5 ± 0.15 | 10 mM histidine-HCl | 275 mM glycerol | — | 0.02% (w/v) PS20 |
| 6.5 ± 0.15 | 10 mM histidine-HCl | 275 mM glycerol | 10 mM methionine | 0.02% (w/v) PS20 |
| 6.5 ± 0.15 | 10 mM histidine-HCl | 275 mM glycerol | 50 mM proline | 0.02% (w/v) PS20 |
| 6.5 ± 0.15 | 10 mM histidine-HCl | 275 mM glycerol | 50 mM arginine-HCl | 0.02% (w/v) PS20 |
| 7.0 ± 0.15 | 10 mM histidine-HCl | 5% trehalose | — | 0.02% (w/v) PS20 |
| 7.0 ± 0.15 | 10 mM histidine-HCl | 5% trehalose | 10 mM methionine | 0.02% (w/v) PS20 |
| 7.0 ± 0.15 | 10 mM histidine-HCl | 5% trehalose | 50 mM proline | 0.02% (w/v) PS20 |
| 7.0 ± 0.15 | 10 mM histidine-HCl | 5% trehalose | 50 mM arginine-HCl | 0.02% (w/v) PS20 |
| 7.0 ± 0.15 | 10 mM histidine-HCl | 8% trehalose | — | 0.02% (w/v) PS20 |
| 7.0 ± 0.15 | 10 mM histidine-HCl | 8% trehalose | 5 mM methionine | 0.005% (w/v) PS20 |
| 7.0 ± 0.15 | 10 mM histidine-HCl | 8% trehalose | 10 mM methionine | 0.005% (w/v) PS20 |
| 7.0 ± 0.15 | 10 mM histidine-HCl | 8% trehalose | 15 mM methionine | 0.005% (w/v) PS20 |
| 7.0 ± 0.15 | 10 mM histidine-HCl | 8% trehalose | 5 mM methionine | 0.02% (w/v) PS20 |
| 7.0 ± 0.15 | 10 mM histidine-HCl | 8% trehalose | 10 mM methionine | 0.02% (w/v) PS20 |
| 7.0 ± 0.15 | 10 mM histidine-HCl | 8% trehalose | 15 mM methionine | 0.02% (w/v) PS20 |
| 7.0 ± 0.15 | 10 mM histidine-HCl | 8% trehalose | 5 mM methionine | 0.05% (w/v) PS20 |
| 7.0 ± 0.15 | 10 mM histidine-HCl | 8% trehalose | 10 mM methionine | 0.05% (w/v) PS20 |
| 7.0 ± 0.15 | 10 mM histidine-HCl | 8% trehalose | 15 mM methionine | 0.05% (w/v) PS20 |
| 7.0 ± 0.15 | 10 mM histidine-HCl | 8% trehalose | 15 mM methionine | 0.02% (w/v) PS20 |
| 7.0 ± 0.15 | 10 mM histidine-HCl | 8% trehalose | 25 mM proline | 0.005% (w/v) PS20 |
| 7.0 ± 0.15 | 10 mM histidine-HCl | 8% trehalose | 50 mM proline | 0.005% (w/v) PS20 |
| 7.0 ± 0.15 | 10 mM histidine-HCl | 8% trehalose | 75 mM proline | 0.005% (w/v) PS20 |
| 7.0 ± 0.15 | 10 mM histidine-HCl | 8% trehalose | 25 mM proline | 0.02% (w/v) PS20 |
| 7.0 ± 0.15 | 10 mM histidine-HCl | 8% trehalose | 50 mM proline | 0.02% (w/v) PS20 |
| 7.0 ± 0.15 | 10 mM histidine-HCl | 8% trehalose | 75 mM proline | 0.02% (w/v) PS20 |
| 7.0 ± 0.15 | 10 mM histidine-HCl | 8% trehalose | 25 mM proline | 0.05% (w/v) PS20 |
| 7.0 ± 0.15 | 10 mM histidine-HCl | 8% trehalose | 50 mM proline | 0.05% (w/v) PS20 |
| 7.0 ± 0.15 | 10 mM histidine-HCl | 8% trehalose | 75 mM proline | 0.05% (w/v) PS20 |
| 7.0 ± 0.15 | 10 mM histidine-HCl | 8% trehalose | 50 mM arginine-HCl | 0.02% (w/v) PS20 |
| 7.0 ± 0.15 | 10 mM histidine-HCl | — | 150 mM arginine-HCl | 0.02% (w/v) PS20 |
| 7.0 ± 0.15 | 10 mM histidine-HCl | 10% trehalose | — | — |
| 7.0 ± 0.15 | 10 mM histidine-HCl | 10% trehalose | — | 0.02% (w/v) PS20 |
| 7.0 ± 0.15 | 10 mM histidine-HCl | 10% trehalose | 5 mM methionine | 0.005% (w/v) PS20 |
| 7.0 ± 0.15 | 10 mM histidine-HCl | 10% trehalose | 10 mM methionine | 0.005% (w/v) PS20 |
| 7.0 ± 0.15 | 10 mM histidine-HCl | 10% trehalose | 15 mM methionine | 0.005% (w/v) PS20 |
| 7.0 ± 0.15 | 10 mM histidine-HCl | 10% trehalose | 5 mM methionine | 0.02% (w/v) PS20 |

TABLE 1B-continued

List of histidine buffer-based formulations

| pH | Buffer | Tonicity agent | Excipient | Surfactant |
|---|---|---|---|---|
| 7.0 ± 0.15 | 10 mM histidine-HCl | 10% trehalose | 10 mM methionine | 0.02% (w/v) PS20 |
| 7.0 ± 0.15 | 10 mM histidine-HCl | 10% trehalose | 15 mM methionine | 0.02% (w/v) PS20 |
| 7.0 ± 0.15 | 10 mM histidine-HCl | 10% trehalose | 5 mM methionine | 0.05% (w/v) PS20 |
| 7.0 ± 0.15 | 10 mM histidine-HCl | 10% trehalose | 10 mM methionine | 0.05% (w/v) PS20 |
| 7.0 ± 0.15 | 10 mM histidine-HCl | 10% trehalose | 15 mM methionine | 0.05% (w/v) PS20 |
| 7.0 ± 0.15 | 10 mM histidine-HCl | 10% trehalose | 25 mM proline | 0.005% (w/v) PS20 |
| 7.0 ± 0.15 | 10 mM histidine-HCl | 10% trehalose | 50 mM proline | 0.005% (w/v) PS20 |
| 7.0 ± 0.15 | 10 mM histidine-HCl | 10% trehalose | 75 mM proline | 0.005% (w/v) PS20 |
| 7.0 ± 0.15 | 10 mM histidine-HCl | 10% trehalose | 25 mM proline | 0.02% (w/v) PS20 |
| 7.0 ± 0.15 | 10 mM histidine-HCl | 10% trehalose | 50 mM proline | 0.02% (w/v) PS20 |
| 7.0 ± 0.15 | 10 mM histidine-HCl | 10% trehalose | 75 mM proline | 0.02% (w/v) PS20 |
| 7.0 ± 0.15 | 10 mM histidine-HCl | 10% trehalose | 25 mM proline | 0.05% (w/v) PS20 |
| 7.0 ± 0.15 | 10 mM histidine-HCl | 10% trehalose | 50 mM proline | 0.05% (w/v) PS20 |
| 7.0 ± 0.15 | 10 mM histidine-HCl | 10% trehalose | 75 mM proline | 0.05% (w/v) PS20 |
| 7.0 ± 0.15 | 10 mM histidine-HCl | 10% trehalose | 50 mM arginine-HCl | 0.02% (w/v) PS20 |
| 7.0 ± 0.15 | 10 mM histidine-HCl | 165 mM glycerol | — | 0.005% (w/v) PS20 |
| 7.0 ± 0.15 | 10 mM histidine-HCl | 165 mM glycerol | — | 0.02% (w/v) PS20 |
| 7.0 ± 0.15 | 10 mM histidine-HCl | 165 mM glycerol | — | 0.05% (w/v) PS20 |
| 7.0 ± 0.15 | 10 mM histidine-HCl | 165 mM glycerol | 5 mM methionine | 0.005% (w/v) PS20 |
| 7.0 ± 0.15 | 10 mM histidine-HCl | 165 mM glycerol | 10 mM methionine | 0.005% (w/v) PS20 |
| 7.0 ± 0.15 | 10 mM histidine-HCl | 165 mM glycerol | 15 mM methionine | 0.005% (w/v) PS20 |
| 7.0 ± 0.15 | 10 mM histidine-HCl | 165 mM glycerol | 5 mM methionine | 0.02% (w/v) PS20 |
| 7.0 ± 0.15 | 10 mM histidine-HCl | 165 mM glycerol | 10 mM methionine | 0.02% (w/v) PS20 |
| 7.0 ± 0.15 | 10 mM histidine-HCl | 165 mM glycerol | 15 mM methionine | 0.02% (w/v) PS20 |
| 7.0 ± 0.15 | 10 mM histidine-HCl | 165 mM glycerol | 5 mM methionine | 0.05% (w/v) PS20 |
| 7.0 ± 0.15 | 10 mM histidine-HCl | 165 mM glycerol | 10 mM methionine | 0.05% (w/v) PS20 |
| 7.0 ± 0.15 | 10 mM histidine-HCl | 165 mM glycerol | 15 mM methionine | 0.05% (w/v) PS20 |
| 7.0 ± 0.15 | 10 mM histidine-HCl | 165 mM glycerol (3%) | 25 mM proline | 0.005% (w/v) PS20 |
| 7.0 ± 0.15 | 10 mM histidine-HCl | 165 mM glycerol (3%) | 50 mM proline | 0.005% (w/v) PS20 |
| 7.0 ± 0.15 | 10 mM histidine-HCl | 165 mM glycerol (3%) | 75 mM proline | 0.005% (w/v) PS20 |
| 7.0 ± 0.15 | 10 mM histidine-HCl | 165 mM glycerol (3%) | 25 mM proline | 0.02% (w/v) PS20 |
| 7.0 ± 0.15 | 10 mM histidine-HCl | 165 mM glycerol (3%) | 50 mM proline | 0.02% (w/v) PS20 |
| 7.0 ± 0.15 | 10 mM histidine-HCl | 165 mM glycerol (3%) | 75 mM proline | 0.02% (w/v) PS20 |
| 7.0 ± 0.15 | 10 mM histidine-HCl | 165 mM glycerol (3%) | 25 mM proline | 0.05% (w/v) PS20 |
| 7.0 ± 0.15 | 10 mM histidine-HCl | 165 mM glycerol (3%) | 50 mM proline | 0.05% (w/v) PS20 |
| 7.0 ± 0.15 | 10 mM histidine-HCl | 165 mM glycerol (3%) | 75 mM proline | 0.05% (w/v) PS20 |
| 7.0 ± 0.15 | 10 mM histidine-HCl | 165 mM glycerol (3%) | 50 mM arginine-HCl | 0.02% (w/v) PS20 |
| 7.0 ± 0.15 | 10 mM histidine-HCl | 275 mM glycerol (5%) | — | — |
| 7.0 ± 0.15 | 10 mM histidine-HCl | 275 mM glycerol (5%) | — | 0.005% (w/v) PS20 |
| 7.0 ± 0.15 | 10 mM histidine-HCl | 275 mM glycerol (5%) | — | 0.02% (w/v) PS20 |
| 7.0 ± 0.15 | 10 mM histidine-HCl | 275 mM glycerol (5%) | — | 0.05% (w/v) PS20 |
| 7.0 ± 0.15 | 10 mM histidine-HCl | 275 mM glycerol (5%) | 5 mM methionine | 0.005% (w/v) PS20 |
| 7.0 ± 0.15 | 10 mM histidine-HCl | 275 mM glycerol (5%) | 10 mM methionine | 0.005% (w/v) PS20 |
| 7.0 ± 0.15 | 10 mM histidine-HCl | 275 mM glycerol (5%) | 15 mM methionine | 0.005% (w/v) PS20 |
| 7.0 ± 0.15 | 10 mM histidine-HCl | 275 mM glycerol (5%) | 5 mM methionine | 0.02% (w/v) PS20 |
| 7.0 ± 0.15 | 10 mM histidine-HCl | 275 mM glycerol (5%) | 10 mM methionine | 0.02% (w/v) PS20 |
| 7.0 ± 0.15 | 10 mM histidine-HCl | 275 mM glycerol (5%) | 15 mM methionine | 0.02% (w/v) PS20 |
| 7.0 ± 0.15 | 10 mM histidine-HCl | 275 mM glycerol (5%) | 5 mM methionine | 0.05% (w/v) PS20 |
| 7.0 ± 0.15 | 10 mM histidine-HCl | 275 mM glycerol (5%) | 10 mM methionine | 0.05% (w/v) PS20 |
| 7.0 ± 0.15 | 10 mM histidine-HCl | 275 mM glycerol (5%) | 15 mM methionine | 0.05% (w/v) PS20 |

TABLE 1B-continued

List of histidine buffer-based formulations

| pH | Buffer | Tonicity agent | Excipient | Surfactant |
|---|---|---|---|---|
| 7.0 ± 0.15 | 10 mM histidine-HCl | 275 mM glycerol | 25 mM proline | 0.005% (w/v) PS20 |
| 7.0 ± 0.15 | 10 mM histidine-HCl | 275 mM glycerol | 50 mM proline | 0.005% (w/v) PS20 |
| 7.0 ± 0.15 | 10 mM histidine-HCl | 275 mM glycerol | 75 mM proline | 0.005% (w/v) PS20 |
| 7.0 ± 0.15 | 10 mM histidine-HCl | 275 mM glycerol | 25 mM proline | 0.02% (w/v) PS20 |
| 7.0 ± 0.15 | 10 mM histidine-HCl | 275 mM glycerol | 50 mM proline | 0.02% (w/v) PS20 |
| 7.0 ± 0.15 | 10 mM histidine-HCl | 275 mM glycerol | 75 mM proline | 0.02% (w/v) PS20 |
| 7.0 ± 0.15 | 10 mM histidine-HCl | 275 mM glycerol | 25 mM proline | 0.05% (w/v) PS20 |
| 7.0 ± 0.15 | 10 mM histidine-HCl | 275 mM glycerol | 50 mM proline | 0.05% (w/v) PS20 |
| 7.0 ± 0.15 | 10 mM histidine-HCl | 275 mM glycerol | 75 mM proline | 0.05% (w/v) PS20 |
| 7.0 ± 0.15 | 10 mM histidine-HCl | 275 mM glycerol | 50 mM arginine-HCl | 0.02% (w/v) PS20 |
| 6.5 ± 0.15 | 10 mM histidine-HCl | 5% sucrose | 50 mM arginine-HCl | 0.02% (w/v) PS20 |
| 6.5 ± 0.15 | 10 mM histidine-HCl | 8% sucrose | 50 mM arginine-HCl | 0.02% (w/v) PS20 |
| 6.5 ± 0.15 | 10 mM histidine-HCl | 10% sucrose | 50 mM arginine-HCl | 0.02% (w/v) PS20 |
| 6.5 ± 0.15 | 10 mM histidine-HCl | 165 mM mannitol | 50 mM arginine-HCl | 0.02% (w/v) PS20 |
| 6.5 ± 0.15 | 10 mM histidine-HCl | 275 mM mannitol | 50 mM arginine-HCl | 0.02% (w/v) PS20 |
| 7.0 ± 0.15 | 10 mM histidine-HCl | 5% sucrose | 50 mM arginine-HCl | 0.02% (w/v) PS20 |
| 7.0 ± 0.15 | 10 mM histidine-HCl | 8% sucrose | 50 mM arginine-HCl | 0.02% (w/v) PS20 |
| 7.0 ± 0.15 | 10 mM histidine-HCl | — | 150 mM arginine-HCl | 0.02% (w/v) PS20 |
| 7.0 ± 0.15 | 10 mM histidine-HCl | 10% sucrose | 50 mM arginine-HCl | 0.02% (w/v) PS20 |
| 7.0 ± 0.15 | 10 mM histidine-HCl | 165 mM mannitol (3%) | 50 mM arginine-HCl | 0.02% (w/v) PS20 |
| 7.0 ± 0.15 | 10 mM histidine-HCl | 275 mM mannitol (5%) | 50 mM arginine-HCl | 0.02% (w/v) PS20 |

TABLE 1C

List of sodium phosphate buffer-based formulations

| pH | Buffer | Tonicity agent | Excipient | Surfactant |
|---|---|---|---|---|
| 6.5 ± 0.15 | 10 mM sodium phosphate | 5% sucrose | — | 0.02% (w/v) PS20 |
| 6.5 ± 0.15 | 10 mM sodium phosphate | 5% sucrose | 5 mM methionine | 0.005% (w/v) PS20 |
| 6.5 ± 0.15 | 10 mM sodium phosphate | 5% sucrose | 10 mM methionine | 0.005% (w/v) PS20 |
| 6.5 ± 0.15 | 10 mM sodium phosphate | 5% sucrose | 15 mM methionine | 0.005% (w/v) PS20 |
| 6.5 ± 0.15 | 10 mM sodium phosphate | 5% sucrose | 5 mM methionine | 0.02% (w/v) PS20 |
| 6.5 ± 0.15 | 10 mM sodium phosphate | 5% sucrose | 10 mM methionine | 0.02% (w/v) PS20 |
| 6.5 ± 0.15 | 10 mM sodium phosphate | 5% sucrose | 15 mM methionine | 0.02% (w/v) PS20 |
| 6.5 ± 0.15 | 10 mM sodium phosphate | 5% sucrose | 5 mM methionine | 0.05% (w/v) PS20 |
| 6.5 ± 0.15 | 10 mM sodium phosphate | 5% sucrose | 10 mM methionine | 0.05% (w/v) PS20 |
| 6.5 ± 0.15 | 10 mM sodium phosphate | 5% sucrose | 15 mM methionine | 0.05% (w/v) PS20 |
| 6.5 ± 0.15 | 10 mM sodium phosphate | 5% sucrose | 25 mM proline | 0.005% (w/v) PS20 |
| 6.5 ± 0.15 | 10 mM sodium phosphate | 5% sucrose | 50 mM proline | 0.005% (w/v) PS20 |
| 6.5 ± 0.15 | 10 mM sodium phosphate | 5% sucrose | 75 mM proline | 0.005% (w/v) PS20 |
| 6.5 ± 0.15 | 10 mM sodium phosphate | 5% sucrose | 25 mM proline | 0.02% (w/v) PS20 |
| 6.5 ± 0.15 | 10 mM sodium phosphate | 5% sucrose | 50 mM proline | 0.02% (w/v) PS20 |
| 6.5 ± 0.15 | 10 mM sodium phosphate | 5% sucrose | 75 mM proline | 0.02% (w/v) PS20 |

TABLE 1C-continued

List of sodium phosphate buffer-based formulations

| pH | Buffer | Tonicity agent | Excipient | Surfactant |
|---|---|---|---|---|
| 6.5 ± 0.15 | 10 mM sodium phosphate | 5% sucrose | 25 mM proline | 0.05% (w/v) PS20 |
| 6.5 ± 0.15 | 10 mM sodium phosphate | 5% sucrose | 50 mM proline | 0.05% (w/v) PS20 |
| 6.5 ± 0.15 | 10 mM sodium phosphate | 5% sucrose | 75 mM proline | 0.05% (w/v) PS20 |
| 6.5 ± 0.15 | 10 mM sodium phosphate | 5% sucrose | 50 mM arginine-HCl | 0.02% (w/v) PS20 |
| 6.5 ± 0.15 | 10 mM sodium phosphate | 8% sucrose | — | 0.005% (w/v) PS20 |
| 6.5 ± 0.15 | 10 mM sodium phosphate | 8% sucrose | — | 0.02% (w/v) PS20 |
| 6.5 ± 0.15 | 10 mM sodium phosphate | 8% sucrose | — | 0.05% (w/v) PS20 |
| 6.5 ± 0.15 | 10 mM sodium phosphate | 8% sucrose | 5 mM methionine | 0.005% (w/v) PS20 |
| 6.5 ± 0.15 | 10 mM sodium phosphate | 8% sucrose | 10 mM methionine | 0.005% (w/v) PS20 |
| 6.5 ± 0.15 | 10 mM sodium phosphate | 8% sucrose | 15 mM methionine | 0.005% (w/v) PS20 |
| 6.5 ± 0.15 | 10 mM sodium phosphate | 8% sucrose | 5 mM methionine | 0.02% (w/v) PS20 |
| 6.5 ± 0.15 | 10 mM sodium phosphate | 8% sucrose | 10 mM methionine | 0.02% (w/v) PS20 |
| 6.5 ± 0.15 | 10 mM sodium phosphate | 8% sucrose | 15 mM methionine | 0.02% (w/v) PS20 |
| 6.5 ± 0.15 | 10 mM sodium phosphate | 8% sucrose | 5 mM methionine | 0.05% (w/v) PS20 |
| 6.5 ± 0.15 | 10 mM sodium phosphate | 8% sucrose | 10 mM methionine | 0.05% (w/v) PS20 |
| 6.5 ± 0.15 | 10 mM sodium phosphate | 8% sucrose | 15 mM methionine | 0.05% (w/v) PS20 |
| 6.5 ± 0.15 | 10 mM sodium phosphate | 8% sucrose | 25 mM proline | 0.005% (w/v) PS20 |
| 6.5 ± 0.15 | 10 mM sodium phosphate | 8% sucrose | 50 mM proline | 0.005% (w/v) PS20 |
| 6.5 ± 0.15 | 10 mM sodium phosphate | 8% sucrose | 75 mM proline | 0.005% (w/v) PS20 |
| 6.5 ± 0.15 | 10 mM sodium phosphate | 8% sucrose | 25 mM proline | 0.02% (w/v) PS20 |
| 6.5 ± 0.15 | 10 mM sodium phosphate | 8% sucrose | 50 mM proline | 0.02% (w/v) PS20 |
| 6.5 ± 0.15 | 10 mM sodium phosphate | 8% sucrose | 75 mM proline | 0.02% (w/v) PS20 |
| 6.5 ± 0.15 | 10 mM sodium phosphate | 8% sucrose | 25 mM proline | 0.05% (w/v) PS20 |
| 6.5 ± 0.15 | 10 mM sodium phosphate | 8% sucrose | 50 mM proline | 0.05% (w/v) PS20 |
| 6.5 ± 0.15 | 10 mM sodium phosphate | 8% sucrose | 75 mM proline | 0.05% (w/v) PS20 |
| 6.5 ± 0.15 | 10 mM sodium phosphate | 8% sucrose | 50 mM arginine-HCl | 0.02% (w/v) PS20 |
| 6.5 ± 0.15 | 10 mM sodium phosphate | 10% sucrose | — | — |
| 6.5 ± 0.15 | 10 mM sodium phosphate | 10% sucrose | — | 0.005% (w/v) PS20 |
| 6.5 ± 0.15 | 10 mM sodium phosphate | 10% sucrose | — | 0.02% (w/v) PS20 |
| 6.5 ± 0.15 | 10 mM sodium phosphate | 10% sucrose | — | 0.05% (w/v) PS20 |
| 6.5 ± 0.15 | 10 mM sodium phosphate | 10% sucrose | 5 mM methionine | 0.005% (w/v) PS20 |
| 6.5 ± 0.15 | 10 mM sodium phosphate | 10% sucrose | 10 mM methionine | 0.005% (w/v) PS20 |
| 6.5 ± 0.15 | 10 mM sodium phosphate | 10% sucrose | 15 mM methionine | 0.005% (w/v) PS20 |
| 6.5 ± 0.15 | 10 mM sodium phosphate | 10% sucrose | 5 mM methionine | 0.02% (w/v) PS20 |
| 6.5 ± 0.15 | 10 mM sodium phosphate | 10% sucrose | 10 mM methionine | 0.02% (w/v) PS20 |
| 6.5 ± 0.15 | 10 mM sodium phosphate | 10% sucrose | 15 mM methionine | 0.02% (w/v) PS20 |
| 6.5 ± 0.15 | 10 mM sodium phosphate | 10% sucrose | 5 mM methionine | 0.05% (w/v) PS20 |
| 6.5 ± 0.15 | 10 mM sodium phosphate | 10% sucrose | 10 mM methionine | 0.05% (w/v) PS20 |

TABLE 1C-continued

List of sodium phosphate buffer-based formulations

| pH | Buffer | Tonicity agent | Excipient | Surfactant |
|---|---|---|---|---|
| 6.5 ± 0.15 | 10 mM sodium phosphate | 10% sucrose | 15 mM methionine | 0.05% (w/v) PS20 |
| 6.5 ± 0.15 | 10 mM sodium phosphate | 10% sucrose | 25 mM proline | 0.005% (w/v) PS20 |
| 6.5 ± 0.15 | 10 mM sodium phosphate | 10% sucrose | 50 mM proline | 0.005% (w/v) PS20 |
| 6.5 ± 0.15 | 10 mM sodium phosphate | 10% sucrose | 75 mM proline | 0.005% (w/v) PS20 |
| 6.5 ± 0.15 | 10 mM sodium phosphate | 10% sucrose | 25 mM proline | 0.02% (w/v) PS20 |
| 6.5 ± 0.15 | 10 mM sodium phosphate | 10% sucrose | 50 mM proline | 0.02% (w/v) PS20 |
| 6.5 ± 0.15 | 10 mM sodium phosphate | 10% sucrose | 75 mM proline | 0.02% (w/v) PS20 |
| 6.5 ± 0.15 | 10 mM sodium phosphate | 10% sucrose | 25 mM proline | 0.05% (w/v) PS20 |
| 6.5 ± 0.15 | 10 mM sodium phosphate | 10% sucrose | 50 mM proline | 0.05% (w/v) PS20 |
| 6.5 ± 0.15 | 10 mM sodium phosphate | 10% sucrose | 75 mM proline | 0.05% (w/v) PS20 |
| 6.5 ± 0.15 | 10 mM sodium phosphate | 10% sucrose | 50 mM arginine-HCl | 0.02% (w/v) PS20 |
| 6.5 ± 0.15 | 10 mM sodium phosphate | 165 mM mannitol | — | 0.02% (w/v) PS20 |
| 6.5 ± 0.15 | 10 mM sodium phosphate | 165 mM mannitol | 5 mM methionine | 0.005% (w/v) PS20 |
| 6.5 ± 0.15 | 10 mM sodium phosphate | 165 mM mannitol | 10 mM methionine | 0.005% (w/v) PS20 |
| 6.5 ± 0.15 | 10 mM sodium phosphate | 165 mM mannitol | 15 mM methionine | 0.005% (w/v) PS20 |
| 6.5 ± 0.15 | 10 mM sodium phosphate | 165 mM mannitol | 5 mM methionine | 0.02% (w/v) PS20 |
| 6.5 ± 0.15 | 10 mM sodium phosphate | 165 mM mannitol | 10 mM methionine | 0.02% (w/v) PS20 |
| 6.5 ± 0.15 | 10 mM sodium phosphate | 165 mM mannitol | 15 mM methionine | 0.02% (w/v) PS20 |
| 6.5 ± 0.15 | 10 mM sodium phosphate | 165 mM mannitol | 5 mM methionine | 0.05% (w/v) PS20 |
| 6.5 ± 0.15 | 10 mM sodium phosphate | 165 mM mannitol | 10 mM methionine | 0.05% (w/v) PS20 |
| 6.5 ± 0.15 | 10 mM sodium phosphate | 165 mM mannitol | 15 mM methionine | 0.05% (w/v) PS20 |
| 6.5 ± 0.15 | 10 mM sodium phosphate | 165 mM mannitol | 25 mM proline | 0.005% (w/v) PS20 |
| 6.5 ± 0.15 | 10 mM sodium phosphate | 165 mM mannitol | 50 mM proline | 0.005% (w/v) PS20 |
| 6.5 ± 0.15 | 10 mM sodium phosphate | 165 mM mannitol | 75 mM proline | 0.005% (w/v) PS20 |
| 6.5 ± 0.15 | 10 mM sodium phosphate | 165 mM mannitol | 25 mM proline | 0.02% (w/v) PS20 |
| 6.5 ± 0.15 | 10 mM sodium phosphate | 165 mM mannitol | 50 mM proline | 0.02% (w/v) PS20 |
| 6.5 ± 0.15 | 10 mM sodium phosphate | 165 mM mannitol | 75 mM proline | 0.02% (w/v) PS20 |
| 6.5 ± 0.15 | 10 mM sodium phosphate | 165 mM mannitol | 25 mM proline | 0.05% (w/v) PS20 |
| 6.5 ± 0.15 | 10 mM sodium phosphate | 165 mM mannitol | 50 mM proline | 0.05% (w/v) PS20 |
| 6.5 ± 0.15 | 10 mM sodium phosphate | 165 mM mannitol | 75 mM proline | 0.05% (w/v) PS20 |
| 6.5 ± 0.15 | 10 mM sodium phosphate | 165 mM mannitol | 50 mM arginine-HCl | 0.02% (w/v) PS20 |
| 6.5 ± 0.15 | 10 mM sodium phosphate | 275 mM mannitol | — | 0.02% (w/v) PS20 |
| 6.5 ± 0.15 | 10 mM sodium phosphate | 275 mM mannitol | 5 mM methionine | 0.005% (w/v) PS20 |
| 6.5 ± 0.15 | 10 mM sodium phosphate | 275 mM mannitol | 10 mM methionine | 0.005% (w/v) PS20 |
| 6.5 ± 0.15 | 10 mM sodium phosphate | 275 mM mannitol | 15 mM methionine | 0.005% (w/v) PS20 |
| 6.5 ± 0.15 | 10 mM sodium phosphate | 275 mM mannitol | 5 mM methionine | 0.02% (w/v) PS20 |
| 6.5 ± 0.15 | 10 mM sodium phosphate | 275 mM mannitol | 10 mM methionine | 0.02% (w/v) PS20 |
| 6.5 ± 0.15 | 10 mM sodium phosphate | 275 mM mannitol | 15 mM methionine | 0.02% (w/v) PS20 |

TABLE 1C-continued

List of sodium phosphate buffer-based formulations

| pH | Buffer | Tonicity agent | Excipient | Surfactant |
|---|---|---|---|---|
| 6.5 ± 0.15 | 10 mM sodium phosphate | 275 mM mannitol | 5 mM methionine | 0.05% (w/v) PS20 |
| 6.5 ± 0.15 | 10 mM sodium phosphate | 275 mM mannitol | 10 mM methionine | 0.05% (w/v) PS20 |
| 6.5 ± 0.15 | 10 mM sodium phosphate | 275 mM mannitol | 15 mM methionine | 0.05% (w/v) PS20 |
| 6.5 ± 0.15 | 10 mM sodium phosphate | 275 mM mannitol | 25 mM proline | 0.005% (w/v) PS20 |
| 6.5 ± 0.15 | 10 mM sodium phosphate | 275 mM mannitol | 50 mM proline | 0.005% (w/v) PS20 |
| 6.5 ± 0.15 | 10 mM sodium phosphate | 275 mM mannitol | 75 mM proline | 0.005% (w/v) PS20 |
| 6.5 ± 0.15 | 10 mM sodium phosphate | 275 mM mannitol | 25 mM proline | 0.005% (w/v) PS20 |
| 6.5 ± 0.15 | 10 mM sodium phosphate | 275 mM mannitol | 50 mM proline | 0.02% (w/v) PS20 |
| 6.5 ± 0.15 | 10 mM sodium phosphate | 275 mM mannitol | 75 mM proline | 0.02% (w/v) PS20 |
| 6.5 ± 0.15 | 10 mM sodium phosphate | 275 mM mannitol | 25 mM proline | 0.05% (w/v) PS20 |
| 6.5 ± 0.15 | 10 mM sodium phosphate | 275 mM mannitol | 50 mM proline | 0.05% (w/v) PS20 |
| 6.5 ± 0.15 | 10 mM sodium phosphate | 275 mM mannitol | 75 mM proline | 0.05% (w/v) PS20 |
| 6.5 ± 0.15 | 10 mM sodium phosphate | 275 mM mannitol | 50 mM arginine-HCl | 0.02% (w/v) PS20 |
| 7.0 ± 0.15 | 10 mM sodium phosphate | 8% sucrose | — | 0.02% (w/v) PS20 |
| 7.0 ± 0.15 | 10 mM sodium phosphate | 5% sucrose | — | 0.02% (w/v) PS20 |
| 7.0 ± 0.15 | 10 mM sodium phosphate | 5% sucrose | 10 mM methionine | 0.02% (w/v) PS20 |
| 7.0 ± 0.15 | 10 mM sodium phosphate | 5% sucrose | 50 mM proline | 0.02% (w/v) PS20 |
| 7.0 ± 0.15 | 10 mM sodium phosphate | 5% sucrose | 50 mM arginine-HCl | 0.02% (w/v) PS20 |
| 7.0 ± 0.15 | 10 mM sodium phosphate | 8% sucrose | 10 mM methionine | 0.02% (w/v) PS20 |
| 7.0 ± 0.15 | 10 mM sodium phosphate | 8% sucrose | 50 mM proline | 0.02% (w/v) PS20 |
| 7.0 ± 0.15 | 10 mM sodium phosphate | 8% sucrose | 50 mM arginine-HCl | 0.02% (w/v) PS20 |
| 7.0 ± 0.15 | 10 mM sodium phosphate | 10% sucrose | — | — |
| 7.0 ± 0.15 | 10 mM sodium phosphate | 10% sucrose | — | 0.02% (w/v) PS20 |
| 7.0 ± 0.15 | 10 mM sodium phosphate | 10% sucrose | — | — |
| 7.0 ± 0.15 | 10 mM sodium phosphate | 10% sucrose | — | 0.02% (w/v) PS20 |
| 7.0 ± 0.15 | 10 mM sodium phosphate | 10% sucrose | 10 mM methionine | 0.02% (w/v) PS20 |
| 7.0 ± 0.15 | 10 mM sodium phosphate | 10% sucrose | 50 mM proline | 0.02% (w/v) PS20 |
| 7.0 ± 0.15 | 10 mM sodium phosphate | 10% sucrose | 50 mM arginine-HCl | 0.02% (w/v) PS20 |
| 7.0 ± 0.15 | 10 mM sodium phosphate | 165 mM mannitol | — | 0.02% (w/v) PS20 |
| 7.0 ± 0.15 | 10 mM sodium phosphate | 165 mM mannitol | 10 mM methionine | 0.02% (w/v) PS20 |
| 7.0 ± 0.15 | 10 mM sodium phosphate | 165 mM mannitol | 50 mM proline | 0.02% (w/v) PS20 |
| 7.0 ± 0.15 | 10 mM sodium phosphate | 165 mM mannitol | 50 mM arginine-HCl | 0.02% (w/v) PS20 |
| 7.0 ± 0.15 | 10 mM sodium phosphate | 275 mM mannitol | — | 0.02% (w/v) PS20 |
| 7.0 ± 0.15 | 10 mM sodium phosphate | 275 mM mannitol | 10 mM methionine | 0.02% (w/v) PS20 |
| 7.0 ± 0.15 | 10 mM sodium phosphate | 275 mM mannitol | 50 mM proline | 0.02% (w/v) PS20 |
| 7.0 ± 0.15 | 10 mM sodium phosphate | 275 mM mannitol | 50 mM arginine-HCl | 0.02% (w/v) PS20 |

TABLE 1D

List of sodium phosphate buffer-based formulations

| pH | Buffer | Tonicity agent | Excipient | Surfactant |
|---|---|---|---|---|
| 6.5 ± 0.15 | 10 mM sodium phosphate | 5% trehalose | — | 0.02% (w/v) PS20 |
| 6.5 ± 0.15 | 10 mM sodium phosphate | 5% trehalose | 5 mM methionine | 0.005% (w/v) PS20 |
| 6.5 ± 0.15 | 10 mM sodium phosphate | 5% trehalose | 10 mM methionine | 0.005% (w/v) PS20 |
| 6.5 ± 0.15 | 10 mM sodium phosphate | 5% trehalose | 15 mM methionine | 0.005% (w/v) PS20 |
| 6.5 ± 0.15 | 10 mM sodium phosphate | 5% trehalose | 5 mM methionine | 0.02% (w/v) PS20 |
| 6.5 ± 0.15 | 10 mM sodium phosphate | 5% trehalose | 10 mM methionine | 0.02% (w/v) PS20 |
| 6.5 ± 0.15 | 10 mM sodium phosphate | 5% trehalose | 15 mM methionine | 0.02% (w/v) PS20 |
| 6.5 ± 0.15 | 10 mM sodium phosphate | 5% trehalose | 5 mM methionine | 0.05% (w/v) PS20 |
| 6.5 ± 0.15 | 10 mM sodium phosphate | 5% trehalose | 10 mM methionine | 0.05% (w/v) PS20 |
| 6.5 ± 0.15 | 10 mM sodium phosphate | 5% trehalose | 15 mM methionine | 0.05% (w/v) PS20 |
| 6.5 ± 0.15 | 10 mM sodium phosphate | 5% trehalose | 25 mM proline | 0.005% (w/v) PS20 |
| 6.5 ± 0.15 | 10 mM sodium phosphate | 5% trehalose | 50 mM proline | 0.005% (w/v) PS20 |
| 6.5 ± 0.15 | 10 mM sodium phosphate | 5% trehalose | 75 mM proline | 0.005% (w/v) PS20 |
| 6.5 ± 0.15 | 10 mM sodium phosphate | 5% trehalose | 25 mM proline | 0.02% (w/v) PS20 |
| 6.5 ± 0.15 | 10 mM sodium phosphate | 5% trehalose | 50 mM proline | 0.02% (w/v) PS20 |
| 6.5 ± 0.15 | 10 mM sodium phosphate | 5% trehalose | 75 mM proline | 0.02% (w/v) PS20 |
| 6.5 ± 0.15 | 10 mM sodium phosphate | 5% trehalose | 25 mM proline | 0.05% (w/v) PS20 |
| 6.5 ± 0.15 | 10 mM sodium phosphate | 5% trehalose | 50 mM proline | 0.05% (w/v) PS20 |
| 6.5 ± 0.15 | 10 mM sodium phosphate | 5% trehalose | 75 mM proline | 0.05% (w/v) PS20 |
| 6.5 ± 0.15 | 10 mM sodium phosphate | 5% trehalose | 50 mM arginine-HCl | 0.02% (w/v) PS20 |
| 6.5 ± 0.15 | 10 mM sodium phosphate | 8% trehalose | — | 0.005% (w/v) PS20 |
| 6.5 ± 0.15 | 10 mM sodium phosphate | 8% trehalose | — | 0.02% (w/v) PS20 |
| 6.5 ± 0.15 | 10 mM sodium phosphate | 8% trehalose | — | 0.05% (w/v) PS20 |
| 6.5 ± 0.15 | 10 mM sodium phosphate | 8% trehalose | 5 mM methionine | 0.005% (w/v) PS20 |
| 6.5 ± 0.15 | 10 mM sodium phosphate | 8% trehalose | 10 mM methionine | 0.005% (w/v) PS20 |
| 6.5 ± 0.15 | 10 mM sodium phosphate | 8% trehalose | 15 mM methionine | 0.005% (w/v) PS20 |
| 6.5 ± 0.15 | 10 mM sodium phosphate | 8% trehalose | 5 mM methionine | 0.02% (w/v) PS20 |
| 6.5 ± 0.15 | 10 mM sodium phosphate | 8% trehalose | 10 mM methionine | 0.02% (w/v) PS20 |
| 6.5 ± 0.15 | 10 mM sodium phosphate | 8% trehalose | 15 mM methionine | 0.02% (w/v) PS20 |
| 6.5 ± 0.15 | 10 mM sodium phosphate | 8% trehalose | 5 mM methionine | 0.05% (w/v) PS20 |
| 6.5 ± 0.15 | 10 mM sodium phosphate | 8% trehalose | 10 mM methionine | 0.05% (w/v) PS20 |
| 6.5 ± 0.15 | 10 mM sodium phosphate | 8% trehalose | 15 mM methionine | 0.05% (w/v) PS20 |
| 6.5 ± 0.15 | 10 mM sodium phosphate | 8% trehalose | 25 mM proline | 0.005% (w/v) PS20 |
| 6.5 ± 0.15 | 10 mM sodium phosphate | 8% trehalose | 50 mM proline | 0.005% (w/v) PS20 |
| 6.5 ± 0.15 | 10 mM sodium phosphate | 8% trehalose | 75 mM proline | 0.005% (w/v) PS20 |
| 6.5 ± 0.15 | 10 mM sodium phosphate | 8% trehalose | 25 mM proline | 0.02% (w/v) PS20 |
| 6.5 ± 0.15 | 10 mM sodium phosphate | 8% trehalose | 50 mM proline | 0.02% (w/v) PS20 |
| 6.5 ± 0.15 | 10 mM sodium phosphate | 8% trehalose | 75 mM proline | 0.02% (w/v) PS20 |

TABLE 1D-continued

List of sodium phosphate buffer-based formulations

| pH | Buffer | Tonicity agent | Excipient | Surfactant |
|---|---|---|---|---|
| 6.5 ± 0.15 | 10 mM sodium phosphate | 8% trehalose | 25 mM proline | 0.05% (w/v) PS20 |
| 6.5 ± 0.15 | 10 mM sodium phosphate | 8% trehalose | 50 mM proline | 0.05% (w/v) PS20 |
| 6.5 ± 0.15 | 10 mM sodium phosphate | 8% trehalose | 75 mM proline | 0.05% (w/v) PS20 |
| 6.5 ± 0.15 | 10 mM sodium phosphate | 8% trehalose | 50 mM arginine-HCl | 0.02% (w/v) PS20 |
| 6.5 ± 0.15 | 10 mM sodium phosphate | 10% trehalose | — | — |
| 6.5 ± 0.15 | 10 mM sodium phosphate | 10% trehalose | — | 0.005% (w/v) PS20 |
| 6.5 ± 0.15 | 10 mM sodium phosphate | 10% trehalose | — | 0.02% (w/v) PS20 |
| 6.5 ± 0.15 | 10 mM sodium phosphate | 10% trehalose | — | 0.05% (w/v) PS20 |
| 6.5 ± 0.15 | 10 mM sodium phosphate | 10% trehalose | 5 mM methionine | 0.005% (w/v) PS20 |
| 6.5 ± 0.15 | 10 mM sodium phosphate | 10% trehalose | 10 mM methionine | 0.005% (w/v) PS20 |
| 6.5 ± 0.15 | 10 mM sodium phosphate | 10% trehalose | 15 mM methionine | 0.005% (w/v) PS20 |
| 6.5 ± 0.15 | 10 mM sodium phosphate | 10% trehalose | 5 mM methionine | 0.02% (w/v) PS20 |
| 6.5 ± 0.15 | 10 mM sodium phosphate | 10% trehalose | 10 mM methionine | 0.02% (w/v) PS20 |
| 6.5 ± 0.15 | 10 mM sodium phosphate | 10% trehalose | 15 mM methionine | 0.02% (w/v) PS20 |
| 6.5 ± 0.15 | 10 mM sodium phosphate | 10% trehalose | 5 mM methionine | 0.05% (w/v) PS20 |
| 6.5 ± 0.15 | 10 mM sodium phosphate | 10% trehalose | 10 mM methionine | 0.05% (w/v) PS20 |
| 6.5 ± 0.15 | 10 mM sodium phosphate | 10% trehalose | 15 mM methionine | 0.05% (w/v) PS20 |
| 6.5 ± 0.15 | 10 mM sodium phosphate | 10% trehalose | 25 mM proline | 0.005% (w/v) PS20 |
| 6.5 ± 0.15 | 10 mM sodium phosphate | 10% trehalose | 50 mM proline | 0.005% (w/v) PS20 |
| 6.5 ± 0.15 | 10 mM sodium phosphate | 10% trehalose | 75 mM proline | 0.005% (w/v) PS20 |
| 6.5 ± 0.15 | 10 mM sodium phosphate | 10% trehalose | 25 mM proline | 0.02% (w/v) PS20 |
| 6.5 ± 0.15 | 10 mM sodium phosphate | 10% trehalose | 50 mM proline | 0.02% (w/v) PS20 |
| 6.5 ± 0.15 | 10 mM sodium phosphate | 10% trehalose | 75 mM proline | 0.02% (w/v) PS20 |
| 6.5 ± 0.15 | 10 mM sodium phosphate | 10% trehalose | 25 mM proline | 0.05% (w/v) PS20 |
| 6.5 ± 0.15 | 10 mM sodium phosphate | 10% trehalose | 50 mM proline | 0.05% (w/v) PS20 |
| 6.5 ± 0.15 | 10 mM sodium phosphate | 10% trehalose | 75 mM proline | 0.05% (w/v) PS20 |
| 6.5 ± 0.15 | 10 mM sodium phosphate | 10% trehalose | 50 mM arginine-HCl | 0.02% (w/v) PS20 |
| 6.5 ± 0.15 | 10 mM sodium phosphate | 165 mM glycerol | — | 0.02% (w/v) PS20 |
| 6.5 ± 0.15 | 10 mM sodium phosphate | 165 mM glycerol | 5 mM methionine | 0.005% (w/v) PS20 |
| 6.5 ± 0.15 | 10 mM sodium phosphate | 165 mM glycerol | 10 mM methionine | 0.005% (w/v) PS20 |
| 6.5 ± 0.15 | 10 mM sodium phosphate | 165 mM glycerol | 15 mM methionine | 0.005% (w/v) PS20 |
| 6.5 ± 0.15 | 10 mM sodium phosphate | 165 mM glycerol | 5 mM methionine | 0.02% (w/v) PS20 |
| 6.5 ± 0.15 | 10 mM sodium phosphate | 165 mM glycerol | 10 mM methionine | 0.02% (w/v) PS20 |
| 6.5 ± 0.15 | 10 mM sodium phosphate | 165 mM glycerol | 15 mM methionine | 0.02% (w/v) PS20 |
| 6.5 ± 0.15 | 10 mM sodium phosphate | 165 mM glycerol | 5 mM methionine | 0.05% (w/v) PS20 |
| 6.5 ± 0.15 | 10 mM sodium phosphate | 165 mM glycerol | 10 mM methionine | 0.05% (w/v) PS20 |
| 6.5 ± 0.15 | 10 mM sodium phosphate | 165 mM glycerol | 15 mM methionine | 0.05% (w/v) PS20 |
| 6.5 ± 0.15 | 10 mM sodium phosphate | 165 mM glycerol | 25 mM proline | 0.005% (w/v) PS20 |

TABLE 1D-continued

List of sodium phosphate buffer-based formulations

| pH | Buffer | Tonicity agent | Excipient | Surfactant |
|---|---|---|---|---|
| 6.5 ± 0.15 | 10 mM sodium phosphate | 165 mM glycerol | 50 mM proline | 0.005% (w/v) PS20 |
| 6.5 ± 0.15 | 10 mM sodium phosphate | 165 mM glycerol | 75 mM proline | 0.005% (w/v) PS20 |
| 6.5 ± 0.15 | 10 mM sodium phosphate | 165 mM glycerol | 25 mM proline | 0.02% (w/v) PS20 |
| 6.5 ± 0.15 | 10 mM sodium phosphate | 165 mM glycerol | 50 mM proline | 0.02% (w/v) PS20 |
| 6.5 ± 0.15 | 10 mM sodium phosphate | 165 mM glycerol | 75 mM proline | 0.02% (w/v) PS20 |
| 6.5 ± 0.15 | 10 mM sodium phosphate | 165 mM glycerol | 25 mM proline | 0.05% (w/v) PS20 |
| 6.5 ± 0.15 | 10 mM sodium phosphate | 165 mM glycerol | 50 mM proline | 0.05% (w/v) PS20 |
| 6.5 ± 0.15 | 10 mM sodium phosphate | 165 mM glycerol | 75 mM proline | 0.05% (w/v) PS20 |
| 6.5 ± 0.15 | 10 mM sodium phosphate | 165 mM glycerol | 50 mM arginine-HCl | 0.02% (w/v) PS20 |
| 6.5 ± 0.15 | 10 mM sodium phosphate | 275 mM glycerol | — | 0.02% (w/v) PS20 |
| 6.5 ± 0.15 | 10 mM sodium phosphate | 275 mM glycerol | 5 mM methionine | 0.005% (w/v) PS20 |
| 6.5 ± 0.15 | 10 mM sodium phosphate | 275 mM glycerol | 10 mM methionine | 0.005% (w/v) PS20 |
| 6.5 ± 0.15 | 10 mM sodium phosphate | 275 mM glycerol | 15 mM methionine | 0.005% (w/v) PS20 |
| 6.5 ± 0.15 | 10 mM sodium phosphate | 275 mM glycerol | 5 mM methionine | 0.02% (w/v) PS20 |
| 6.5 ± 0.15 | 10 mM sodium phosphate | 275 mM glycerol | 10 mM methionine | 0.02% (w/v) PS20 |
| 6.5 ± 0.15 | 10 mM sodium phosphate | 275 mM glycerol | 15 mM methionine | 0.02% (w/v) PS20 |
| 6.5 ± 0.15 | 10 mM sodium phosphate | 275 mM glycerol | 5 mM methionine | 0.05% (w/v) PS20 |
| 6.5 ± 0.15 | 10 mM sodium phosphate | 275 mM glycerol | 10 mM methionine | 0.05% (w/v) PS20 |
| 6.5 ± 0.15 | 10 mM sodium phosphate | 275 mM glycerol | 15 mM methionine | 0.05% (w/v) PS20 |
| 6.5 ± 0.15 | 10 mM sodium phosphate | 275 mM glycerol | 25 mM proline | 0.005% (w/v) PS20 |
| 6.5 ± 0.15 | 10 mM sodium phosphate | 275 mM glycerol | 50 mM proline | 0.005% (w/v) PS20 |
| 6.5 ± 0.15 | 10 mM sodium phosphate | 275 mM glycerol | 75 mM proline | 0.005% (w/v) PS20 |
| 6.5 ± 0.15 | 10 mM sodium phosphate | 275 mM glycerol | 25 mM proline | 0.005% (w/v) PS20 |
| 6.5 ± 0.15 | 10 mM sodium phosphate | 275 mM glycerol | 50 mM proline | 0.02% (w/v) PS20 |
| 6.5 ± 0.15 | 10 mM sodium phosphate | 275 mM glycerol | 75 mM proline | 0.02% (w/v) PS20 |
| 6.5 ± 0.15 | 10 mM sodium phosphate | 275 mM glycerol | 25 mM proline | 0.05% (w/v) PS20 |
| 6.5 ± 0.15 | 10 mM sodium phosphate | 275 mM glycerol | 50 mM proline | 0.05% (w/v) PS20 |
| 6.5 ± 0.15 | 10 mM sodium phosphate | 275 mM glycerol | 75 mM proline | 0.05% (w/v) PS20 |
| 6.5 ± 0.15 | 10 mM sodium phosphate | 275 mM glycerol | 50 mM arginine-HCl | 0.02% (w/v) PS20 |
| 7.0 ± 0.15 | 10 mM sodium phosphate | 8% trehalose | — | 0.02% (w/v) PS20 |
| 7.0 ± 0.15 | 10 mM sodium phosphate | 5% trehalose | — | 0.02% (w/v) PS20 |
| 7.0 ± 0.15 | 10 mM sodium phosphate | 5% trehalose | 10 mM methionine | 0.02% (w/v) PS20 |
| 7.0 ± 0.15 | 10 mM sodium phosphate | 5% trehalose | 50 mM proline | 0.02% (w/v) PS20 |
| 7.0 ± 0.15 | 10 mM sodium phosphate | 5% trehalose | 50 mM arginine-HCl | 0.02% (w/v) PS20 |
| 7.0 ± 0.15 | 10 mM sodium phosphate | 8% trehalose | 10 mM methionine | 0.02% (w/v) PS20 |
| 7.0 ± 0.15 | 10 mM sodium phosphate | 8% trehalose | 50 mM proline | 0.02% (w/v) PS20 |
| 7.0 ± 0.15 | 10 mM sodium phosphate | 8% trehalose | 50 mM arginine-HCl | 0.02% (w/v) PS20 |
| 7.0 ± 0.15 | 10 mM sodium phosphate | 10% trehalose | — | — |

TABLE 1D-continued

List of sodium phosphate buffer-based formulations

| pH | Buffer | Tonicity agent | Excipient | Surfactant |
|---|---|---|---|---|
| 7.0 ± 0.15 | 10 mM sodium phosphate | 10% trehalose | — | 0.02% (w/v) PS20 |
| 7.0 ± 0.15 | 10 mM sodium phosphate | 10% trehalose | — | — |
| 7.0 ± 0.15 | 10 mM sodium phosphate | 10% trehalose | — | 0.02% (w/v) PS20 |
| 7.0 ± 0.15 | 10 mM sodium phosphate | 10% trehalose | 10 mM methionine | 0.02% (w/v) PS20 |
| 7.0 ± 0.15 | 10 mM sodium phosphate | 10% trehalose | 50 mM proline | 0.02% (w/v) PS20 |
| 7.0 ± 0.15 | 10 mM sodium phosphate | 10% trehalose | 50 mM arginine-HCl | 0.02% (w/v) PS20 |
| 7.0 ± 0.15 | 10 mM sodium phosphate | 165 mM glycerol | — | 0.02% (w/v) PS20 |
| 7.0 ± 0.15 | 10 mM sodium phosphate | 165 mM glycerol | 10 mM methionine | 0.02% (w/v) PS20 |
| 7.0 ± 0.15 | 10 mM sodium phosphate | 165 mM glycerol | 50 mM proline | 0.02% (w/v) PS20 |
| 7.0 ± 0.15 | 10 mM sodium phosphate | 165 mM glycerol | 50 mM arginine-HCl | 0.02% (w/v) PS20 |
| 7.0 ± 0.15 | 10 mM sodium phosphate | 275 mM glycerol | — | 0.02% (w/v) PS20 |
| 7.0 ± 0.15 | 10 mM sodium phosphate | 275 mM glycerol | 10 mM methionine | 0.02% (w/v) PS20 |
| 7.0 ± 0.15 | 10 mM sodium phosphate | 275 mM glycerol | 50 mM proline | 0.02% (w/v) PS20 |
| 7.0 ± 0.15 | 10 mM sodium phosphate | 275 mM glycerol | 50 mM arginine-HCl | 0.02% (w/v) PS20 |

TABLE 1E

List of various formulations

| pH | Buffer | Tonicity agent | Excipient | Surfactant |
|---|---|---|---|---|
| 5.0 ± 0.15 | 10 mM sodium acetate | 2.5% glycerol | None | None |
| 5.0 ± 0.15 | 10 mM sodium citrate | 10% trehalose | None | None |
| 5.5 ± 0.15 | 10 mM sodium citrate | 0.9% NaCl | None | None |
| 6.0 ± 0.15 | 10 mM sodium citrate | 10% trehalose | None | None |
| 6.5 ± 0.15 | 10 mM sodium citrate | 10% sucrose | None | None |
| 5.5 ± 0.15 | 10 mM histidine-HCl | 10% trehalose | None | None |
| 6.0 ± 0.15 | 10 mM histidine-HCl | 10% trehalose | None | None |
| 7.0 ± 0.15 | 10 mM histidine-HCl | 275 mM glycerol (2.5%) | None | None |
| 7.0 ± 0.15 | 10 mM histidine-HCl | 0.9% NaCl | None | None |
| 6.5 ± 0.15 | 10 mM sodium phosphate | 275 mM glycerol (2.5%) | None | 0.02% (w/v) PS20 |
| 6.5 ± 0.15 | 10 mM sodium phosphate | 150 mM NaCl (0.9%) | None | 0.02% (w/v) PS20 |
| 6.5 ± 0.15 | 10 mM sodium phosphate | 50 mM NaCl (0.3%) | 100 mM arginine-HCl | 0.02% (w/v) PS20 |
| 6.5 ± 0.15 | 10 mM sodium phosphate | 150 mM NaCl (0.9%) | None | None |
| 6.5 ± 0.15 | 10 mM sodium phosphate | 130 mM NaCl (0.7%) | 50 mM proline | 0.02% (w/v) PS20 |
| 6.5 ± 0.15 | 10 mM sodium phosphate | 150 mM NaCl (0.9%) | 10 mM methionine | 0.02% (w/v) PS20 |
| 6.5 ± 0.15 | 10 mM histidine-HCl | 10% sucrose | — | — |
| 7.0 ± 0.15 | 10 mM histidine-HCl | 10% sucrose | — | — |

Analytical methods were developed and verified for subsequent testing of the physicochemical characteristics of different formulation candidates under stress conditions. The analytical methods used are outlined in Table 2.

TABLE 2

Analytical methods for protein stability and liquid product characterization.

| Method | Purpose |
| --- | --- |
| Reversed-phase ultra-performance liquid chromatography (RP-UPLC) | Purity: chemical changes, content |
| High performance size-exclusion chromatography (HP-SEC) | Purity: monomer, higher molecular weight species |
| UV spectroscopy | Peptide content, turbidity |
| Micro-Flow Imaging (MFI) | Quantification and visualization of subvisible particles (~1-100 μm) |
| Visual inspection | Visible particles according to Ph. Eur |
| pH | pH |
| Osmolality | Osmolality |

The stress conditions applied to the different formulations are presented in Table 3. Some formulations were subjected to accelerated storage for 4 weeks at 25° C. and 40° C. while others were subjected to accelerated storage for at least 3 months at 5° C., 25° C. and 40° C.

TABLE 3

Stress conditions for formulations.

| Condition | Parameters | Time points |
| --- | --- | --- |
| Unstressed | Formulation | T0 |
| Mechanical stress | Mechanical stress: shaking | T-mech |
| Freeze-thawing stress | Five freeze-thaw cycles | T-FT |
| Storage at 5° C. | Storage at 2-8° C. | T-1m_5° C. T-3m_5° C. |
| Storage at 25° C. | Storage at 25° C. and 60% r.h. | T-1m_25° C. T-3m_25° C. |
| Storage at 40° C. | Storage at 40° C. and 75% r.h. | T-1m_40° C. T-3m_40° C. |

Each of the conditions outlined at different time points in Table 3 may be considered as a stress condition (except when unstressed).

Example 2: Stability Testing

Formulations of Table 4 were prepared and tested in one or more of the following sets of experiments.
Visual Inspection The vials are inspected for the presence or absence of visible particles under gentle, manual, radial agitation for 5 seconds in front of a white background and for 5 seconds in front of a black background according to the European Pharmacopoeia (8th edition; monograph 2.9.20).

Based on the above, it was determined that at T0, substantial visible particle formation (precipitation) was detected in one formulation at pH 5.0±0.15, containing 10 mM sodium citrate and 10% trehalose and in another formulation at pH 5.5±0.15, containing 10 mM histidine-HCl and 10% trehalose. At T0, the remaining twenty-six formulations tested showed no or very low amounts of visible particles.

No substantial impact on the visible particle content was observed upon storage for 1 month at 5° C. in formulations tested under these conditions.

After storage for 1 month at 25° C. and/or 1 month at 40° C., high amount of visible particles was detected in formulations containing sodium acetate, sodium citrate or histidine-HCl at low pH (5.5±0.15) and in some formulations at pH of between 6.0±0.15-7.0±0.15 containing histidine-HCl and 10% trehalose or sucrose (without excipient or surfactant).

Despite the absence of surfactants, other formulations containing histidine or phosphate buffer and sugar performed well with respect to the determined visible particle contents after storage for 1 month at 25° C. and at 40° C.

Very few visible particles were detected in tested formulations at pH 7.0±0.15 containing histidine-HCl, a tonicity agent, a surfactant with or without amino acid excipients or at pH 6.5±0.15 containing sodium phosphate, a tonicity agent with or without a surfactant when stored for three months at 5° C., 25° C. and/or 40° C.

Freeze-thaw stress led to substantial formation of visible particles only in two histidine-based formulations containing arginine (formulations at pH 7.0±0.15 each containing either 10 mM histidine-HCl, 50 mM arginine-HCl, 3% mannitol and 0.02% (w/v) PS20 or 10 mM histidine-HCl, 150 mM arginine-HCl and 0.02% (w/v) PS20). Additionally, phase separation was observed in most of the tested formulations, which disappeared after gentle homogenization of the samples.

Mechanical stress led to a strong increase in visible particle content for some of the polysorbate-free formulations tested.
pH pH is measured with a calibrated pH meter.

The pH of various formulations is measured at room temperature (e.g., generally between 20 and 25° C. and more particularly between 22-24° C.). The pH values of the tested formulations remained relatively constant throughout the stability study. Generally, the histidine-based formulations showed more fluctuations than the phosphate-based formulations.
Osmolality At T0, the osmolality values for formulations that contain the peptide of interest, a buffering agent and a tonicity agent were in range between 299-369 mOsmol/kg. The values for formulations that also contain an excipient and/or a surfactant were between 276-313. A lower osmolality value of 235 mOsmol/kg was measured for one of the formulations containing proline. If desired, the osmolality of such formulations could be raised by increasing the sugar content.
UV Spectroscopy UV measurements are performed in 96-well plates. Absorbance (A) is measured at 280 nm (A280 nm) and 320 nm (A320 nm).

The peptide concentrations at T0 and/or after storage for 1 month at 25° C. were within the target range (0.3±0.05 mg/ml) for all formulations except for formulations that showed visible precipitation, in some of the citrate-based formulations and/or those at pH of 5.5±0.01 or lower. Storage for 1 month at 40° C. had no effect on the peptide content; the peptide concentration did not vary or remained well within target range, except for one of the precipitated formulations.

Some of the polysorbate-free formulations tested were negatively impacted after mechanical stress.

Freeze-thaw stress as well as storage at 5° C., for 1 month had no influence on the peptide content in the tested formulations. The peptide content also remained stable for the formulations stored for three months at 5° C. and 25° C.

After storage at 40° C. for 3 months, a slight decrease in peptide concentration was observed in the tested formulations. However, they all remained well within target range.

Turbidity

The optical density (OD) values determined at 350 nm (OD350 nm) and either 550 nm (OD550 nm) or 580 nm (OD580 nm) are used to assess the turbidity of the samples.

At T0, turbidity (OD350 nm and OD550 nm) was very low for all formulations except for one of the formulations that had shown precipitation during preparation.

Turbidity values was very low after freeze-thaw stress and mechanical stress in tested formulations, and after storage for 1 month (all temperatures). However, the polysorbate-free formulations tested after mechanical stress showed very high turbidity (OD350 nm>0.10). Upon storage at 25° C. for 1 month, the turbidity values remained low. Only upon storage at 40° C. for 1 month, the turbidity (OD350 nm) increased slightly for some of the formulations including those that showed precipitation at T0. The OD550 nm values did not change substantially upon storage at 25° C. and 40° C.

After storage for 3 months, a slight increase in turbidity was also observed for some of the formulations stored at 40° C. However, with OD350 nm values of 0.03 and 0.02 the turbidity of these samples is still generally low.

Micro-Flow Imaging™ (MFI)

Flow imaging microscopy allows enumerating and visualization of subvisible particles present in a sample.

In this technique bright-field images are captured in successive frames as a continuous sample stream passes through a flow cell positioned in the field of view of a microscopic system. The digital images of the particles present in the sample are processed by image morphology analysis software that allows their quantification in size and count (Zölls, S et al., The AAPS Journal. Vol 15(4), p. 1200, 2013).

Micro-Flow Imaging measurements are conducted on a 5200 particle-analyzer system.

MFI View System Software (MVSS) version 2-R2-6.1.20.1915 is used to perform the measurements and MFI View Analysis Suite (MVAS) software version 1.3.0.1007 is used to analyze the samples.

At T0, MFI revealed low concentrations of subvisible particles in all formulations except in formulations where precipitation was observed (i.e., high concentration of subvisible particles was measured)

Storage for 1 month at 5° C. had no impact on the subvisible particle concentrations in any of the formulations tested.

Storage at 25° C. or 40° C. for 1 month revealed good stability of most formulations, since only slight increases in subvisible particle counts were observed yet the concentration of subvisible particles remained low.

At T−1m_25° C. and/or T−1m_40° C., a high concentration of subvisible particles was also observed for one of the polysorbate-free formulation.

At T−1m_25° C. and/or T−1m_40° C., a high concentration of subvisible particles was also observed for other formulations such as those that showed precipitation at T0, those at pH of 5.5±0.01 or below and one formulation at pH 6.0±0.01 containing 10 mM histidine-HCl and 10% trehalose showed a substantial change in subvisible particle content.

Low concentration of subvisible particles and very good stability was observed for the formulations tested after storage at 5° C., 25° C. and 40° C. for 3 months.

Freeze-thaw stress had no impact on the particle counts for most of the formulations tested under those conditions. Only the two histidine-based formulations containing arginine showed a clear increase in subvisible particles under these conditions which was consistent with visual inspection.

Most formulations showed a very good stability towards mechanical stress. Only the two polysorbate-free formulations tested showed a significant increase in subvisible particle content which was consistent with visual inspection.

Generally, citrate formulations and/or those having a pH of 5.0-5.5 appeared to have the greatest number of subvisible particles whereas formulations containing histidine or phosphate appear to have lower number of subvisible particles.

High Performance Size-Exclusion Chromatography (HP-SEC)

In unstressed ROSE-010 samples, a clear monomer peak as well as peaks corresponding to high molecular weight species (HMWS) and low molecular weight species (LMWS) were observed at 280 nm. The ability of the HP-SEC method to detect changes in the monomer, HMWS and LMWS content was tested with stressed samples. The method was capable of detecting degradation products, as indicated by a slight increase of the HMWS content after one week storage at 40° C. Multiple freeze-thaw cycles had no influence on the SEC profile. Mechanical stress led to a substantial loss of the overall signal intensity.

Relative Monomer Content

At T0, the monomer content of several of the tested formulations was about 96%.

However, at T0, the citrate formulations showed a lower monomer content of about 80%. The monomer content of formulations containing NaCl as tonicity agent was also low (ranging from 67.6% to 81.9%). The monomer content of the two histidine-based formulations containing arginine was also very low at T0 (64.9%). After storage for 1 month at 25° C., the monomer content decreased even more for these formulations (monomer content ranging from 63.2 to 70.7% for citrate-based formulations and from 44.4 to 59.6% for formulations containing NaCl).

The monomer content generally decreased even further when formulations were stored for 1 month at 40° C. (especially those containing NaCl). The monomer content tested for formulations containing NaCl also decreased upon storage for 1 month at 5° C. compared to T0.

After storage for 1 month at 5° C. or for 1 month at 25° C., the monomer content of the remaining formulations tested was relatively unchanged, with the exception of one the two histidine-based formulations containing arginine (66.5% at 5° C. and 78.3% at 25° C.). The monomer content of these formulations decreased slightly under storage for 1 month at 40° C.

Monomer content of 96% and higher at T−1m_5° C., of 95.8% or higher at T−1m_25° C. and of 94.3% or higher at T−1 m_40° C. were measured in the most stable formulations.

Storage for 3 months at 5° C. had no effect on the monomer content for the formulations tested under these conditions (monomer content of 95.9% or higher). Storage at 25° C. for 3 months led to a slight decrease in the monomer content for two of these formulations (decrease of 0.7% and 1.6% respectively compared to T0, i.e., monomer content of 95.1 or 95.3% or higher). Storage at 40° C. for 3 months led to a slight decrease in monomer content for three of the formulations tested and to a modest decrease for two of these formulations (decrease of 7.2% and 8.2% compared to T0). Three formulations still had a monomer content of 93.0% or higher at T−3m_40° C.

In comparison with T0 unstressed sample, mechanical stress led to a substantial decrease in monomer content in two of the polysorbate-free formulations tested (with approximately 54-60% decrease). All other formulations remained relatively stable upon mechanical stress.

Freeze-thaw stress had no substantial impact on the monomer content in any of the formulations tested under these conditions.

Relative Content of HMWS

At T0, the relative aggregate content was about 1% for most histidine-based formulations. The citrate-based formulation showed a higher aggregate content of about 15 to 17.7% (at 280 nm). For citrate-based formulation, the aggregate content further increased with both heat stress conditions (ranging from about 27 to 33.7% at T−1m_25° C. and from about 21.7 to 38.6% at T−1m_40° C., 280 nm).

The relative aggregate content for most of the histidine-based formulations stayed very low (ranging from 0.8% to 1.6%) at T−1m_5° C. and/or T−1m_25° C. and increased slightly at T−1m_40° C. (ranging from 1.2% to 3.0%). The two histidine-based formulations containing arginine showed a relative aggregate content of between 10.2 to 19.7% at 5° C., 10.3 to 20.0% at 25° C. and 13.1 to 20.3% at 40° C. One formulation at pH 7.0±0.15 containing histidine-HCl and NaCl showed a substantial increase in aggregate content after storage for 1 month at 40° C. (about 30% at T−1m_40° C., 280 nm). A minor increase was observed for other formulations (ranging from about 1.2 to 3.0% at T−1m_40° C., 280 nm).

After mechanical stress, a clear increase in the relative HMWS content was observed for one of the polysorbate-fee formulations (reaching 11.1%).

Freeze-thaw stress had no substantial effect on the relative HMWS content in of the formulations tested under these conditions.

For some of the formulations, especially those containing sodium phosphate as buffering agent, a different peak shape, which was interpreted as high-molecular-weight species, was already present at T0. However, for two of such formulations (one containing glycerol and polysorbate and the other containing sucrose and polysorbate) a very low aggregate content at T0, T−1m_5° C. and T−1m_25° C. (1.6% or lower) was measured and increased slightly at T−1m_40° C. (reaching 4.9% and 2.6% respectively).

Storage for 3 months at 5° C. had no influence on the relative HMWS content in any of the formulations tested. Storage for 3 months at 25° C. led to a slight increase in the HMWS content in three of these formulations (reaching 1.7%, 1.9% and 2.2%). Storage for 3 months at 40° C. led to a substantial increase in HMWS content (from 2.2 to 8.2%) for all formulations tested, which was strongest for two of these formulations (5.7% and 8.2%). Still the HMWS content was below 10% for all formulations.

Relative Content of LMWS

At T0, the relative amount of LMWS was about 2-3.3% at 280 nm for all formulations tested.

Mechanical stress led to a substantial increase in the relative LMWS content, especially for the two polysorbate-free formulations (49.5-50.1%), but also for one of the two histidine-based formulation containing arginine (15.0%) and in several formulations containing NaCl as tonicity agent (ranging from 16.5 to 22.8%). These formulations also showed a high LMWS content upon storage for 1 month at 5° C., 25° C. and 40° C. For example, the two histidine-based formulations containing arginine had a LMWS content after storage at 5° C. for 1 month ranging from 13.7% to 34.8%.

Freeze-thaw stress led to a clear increase in the relative LMWS content for formulations containing NaCl as tonicity agent (from 8.9 to 18.1%); the LMWS content for all other formulations tested remained unchanged.

Storage for 1 month at 5° C., 25° C. and 40° C. had no substantial impact on the relative LMWS content of the remaining formulations (reaching 1.6 to 5.5%).

Storage for 3 months at 5° C. or 25° C. had no impact on the relative LMWS content for any of the formulations tested. Storage for 3 months at 40° C. led to a small increase in the relative LMWS content for all tested formulations, which reached 4.6 to 5.1% for two of these formulations.

The total peak remained stable amongst all time points and samples. The only exceptions were the polysorbate-free formulations after mechanical stress, which showed almost a complete loss of signal.

Reversed Phase Ultra-Performance Liquid Chromatography (RP-UPLC)

The stability-indicating potential of the RP-UPLC method was tested with stressed samples. The RP-UPLC method is able to detect degradation products, as indicated by new peaks arising after one-week storage at 40° C. Precipitation observed in samples after mechanical stress led to a decrease of the total peak area in RP-UPLC chromatogram.

The RP-UPLC is sensitive for the detection of impurities and can be used for the analysis of the formulations.

Main Peak Content

At T0, the relative main peak area of the tested formulations ranged between 94.7% and 97.1%.

Storage at 5° C. for 1 month had no impact on the relative main peak area in any of formulations tested.

After storage at 25° C. for 1 month, the relative main peak area was slightly lower for the formulations that showed precipitation at preparation (91.6% and 93.1%) but generally remained in the same ranges for the other formulations (from 93.1 to 96.3%).

For some formulations, storage at 40° C. for 1 month further decreased the main peak content (from 83.3% to 89.2%). For example, a formulation at pH 5.0 that contains sodium citrate and trehalose showed a main peak content of 83.3%, one formulation at pH 6.0 containing sodium citrate and trehalose showed a main peak content of 89.2%, one formulation at pH 7.0 containing histidine-HCl and sucrose and one formulation at pH 7.5 containing sodium phosphate and sucrose, both without excipients and surfactants showed a main peak content of 89.0% and 87.6% respectively. Generally, the main peak content remained in the range of between 90.0% to 94.5% for the other formulations tested.

Storage at 5° C. for 3 months had no effect on the relative main peak area in any of the formulations tested. Storage at 25° C. for 3 months led to a small decrease in the relative main peak area (varying from 94.2 to 94.9%), while storage at 40° C. for 3 months led to a substantial decrease, with the lowest relative main peak area observed of 82.0-83.0%).

Freeze-thaw stress had no impact on the relative main peak area in any of formulations tested under these conditions.

Mechanical stress had no substantial impact on most of formulations tested under these conditions, except for the polysorbate-free formulations (relative main peak area of 72.0% and 89.8%).

Total Impurity Content

The inverse trend was observed for the total impurity content. The total impurity content of most formulations at T0 varied from 2.9 to 3.9%. The highest level of impurity at T0 was measured for one of the formulations that showed precipitation during preparation (5.3%).

An increase in total impurities was observed for the polysorbate-free formulations (10.3% and 28.0% total impurities) after mechanical stress. There was no significant impact on total impurity content for formulations submitted to freeze-thaw.

The level of impurities was slightly higher after storage at 25° C. for 1 month generally ranging from 4.2% to 5.5% with the exception of the formulations that showed precipitation during preparation (6.9% and 8.4%).

Storage at 40° C. for 1 month further increased the level of impurities in all formulations. The four formulations that showed a decrease in the main peak (from 83.3% to 89.2%) also showed an increase in the level of impurities (from 10.8 to 16.7%). However, for most of the histidine-based or sodium phosphate-based formulations tested, the level of impurities remained below 10%.

No impact of storage at 5° C. was detected even after 3 or 6 months in the formulations tested. A gradual increase for formulations stored at 25 and 40° C. for 3 months was observed. The total impurity content at T3m–5° C. was between 3.5% to 4.0%, the total impurity content at T3m-25° C. was between 5.1% to 5.8% and the total impurity content at T3m-40° C. was between 11.7% to 18.0%.

The total peak area remained constant for most time points in the formulations tested. For the T-mech samples and the T–1m_40° C. samples, slightly higher peak areas were observed. For the polysorbate-free formulations after mechanical stress, an almost complete loss of signal was observed (data not shown).

Pharmaceutical formulations appear more stable at a higher pH (e.g., pH 6.0±0.15 to 7.5±0.15) and as such formulations containing low pH buffers appear less stable. A pH of between 6.5±0.15 to 7.0±0.15 appears beneficial for peptide stability. Surfactants and amino acid stabilizers may help in preserving the stability of the formulations especially against stress conditions.

Formulations comprising GLP-1 or other GLP-1 analogues are also expected to be stable under the same conditions described herein and more specifically in the experimental section.

TABLE 4

| Composition |
| --- |
| F1: 10 mM sodium acetate pH 5.0; 2.5% glycerol |
| F2: 10 mM sodium citrate pH 5.0; 10% trehalose |
| F3: 10 mM sodium citrate pH 5.5; 0.9% NaCl |
| F4: 10 mM sodium citrate pH 6.0; 10% trehalose |
| F5: 10 mM sodium citrate pH 6.5; 10% sucrose |
| F6: 10 mM histidine-HCl pH 5.5; 10% trehalose |
| F7: 10 mM histidine-HCl pH 6.0; 10% trehalose |
| F8: 10 mM histidine-HCl pH 6.5; 10% sucrose |
| F9: 10 mM histidine-HCl pH 7.0; 10% sucrose |
| F10: 10 mM histidine-HCl pH 7.0; 5% mannitol |
| F11: 10 mM histidine-HCl pH 7.0; 0.9% NaCl |

TABLE 4-continued

| Composition |
| --- |
| F12: 10 mM sodium phosphate pH 6.5; 10% sucrose |
| F13: 10 mM sodium phosphate pH 7.0; 10% sucrose |
| F14: 10 mM sodium phosphate pH 7.5; 10% sucrose |
| F15: 10 mM histidine-HCl pH 7.0; 165 mM mannitol; 50 mM arginine-HCl, 0.02% (w/v) PS20 |
| F16: 10 mM histidine-HCl pH 7.0; 165 mM mannitol; 50 mM proline; 0.02% (w/v) PS20 |
| F17: 10 mM histidine-HCl pH 7.0; 275 mM mannitol; 10 mM methionine; 0.02% (w/v) PS20 |
| F18: 10 mM histidine-HCl pH 7.0; 275 mM mannitol; 0.02% (w/v) PS20 |
| F19: 10 mM histidine-HCl pH 7.0; 150 mM arginine-HCl; 0.02% (w/v) PS20 |
| F20: 10 mM histidine-HCl pH 7.0; 275 mM glycerol |
| F21: 10 mM phosphate-Na pH 6.5; 275 mM glycerol; 0.02% (w/v) PS20 |
| F22: 10 mM phosphate-Na pH 6.5; 150 mM NaCl; 0.02% (w/v) PS20 |
| F23: 10 mM phosphate-Na pH 6.5; 50 mM NaCl; 100 mM arginine-HCl; 0.02% (w/v) PS20 |
| F24: 10 mM phosphate-Na pH 6.5; 150 mM NaCl |
| F25: 10 mM phosphate-Na pH 6.5; 130 mM NaCl; 50 mM proline; 0.02% (w/v) PS20 |
| F26: 10 mM phosphate-Na pH 6.5; 150 mM NaCl; 10 mM methionine; 0.02% (w/v) PS20 |
| F27: 10 mM phosphate-Na pH 6.5; 8% sucrose; 0.02% (w/v) PS20 |
| F28: 10 mM histidine-HCl pH 7.0; 8% sucrose; 10 mM methionine; 0.02% (w/v) PS20 |

The aspects, embodiments and examples described herein are illustrative and are not meant to be limitative. Variations of the foregoing embodiments, including alternatives, modifications and equivalents, are intended by the inventors to be encompassed by the present disclosure. Citations listed in the present application are incorporated herein by reference.

SEQUENCE LISTING

SEQ ID NO: 1

$X_1X_2$EGTFTSDVSSYL$X_3$GQAAK$X_4$FIAWLVKGR$X_5$

Wherein $X_1$ may be L-histidine, D-histidine, desaminohistidine, 2-amino-histidine, beta-hydroxy-histidine, homohistidine, alpha-fluoromethylhistidine or alpha-methyl-histidine Wherein $X_2$ may be V, A, G, T, I or alpha-methyl-Ala Wherein $X_3$ may be E, Q, A, T, S or G Wherein $X_4$ may be E, Q, A, T, S or G Wherein $X_5$ may be absent, Gly-NH$_2$ or Gly-OH

SEQ ID NO: 2

(GLP-1 (7-37)
H-HAEGTFTSDVSSYLEGQAAKEFIAWLVKGRG-OH

SEQ ID NO:3

(ROSE-010)
H-HVEGTFTSDVSSYLEGQAAKEFIAWLVKGRG-OH

-continued

SEQ ID NO:4
(SEQ ID NO:2 without terminal glycine residue)
H-HAEGTFTSDVSSYLEGQAAKEFIAWLVKGR-NH$_2$ SEQ ID NO:5
(ROSE-010 without terminal glycine residue)
H-HVEGTFTSDVSSYLEGQAAKEFIAWLVKGR-NH$_2$

STATEMENTS OF INVENTION

1. A liquid pharmaceutical formulation comprising glucagon-like peptide 1 (GLP-1) or a GLP-1 analogue thereof as defined in SEQ ID NO:1, a buffering agent, a tonicity agent, and optionally an excipient and/or surfactant.
2. The pharmaceutical formulation of statement 1, wherein the pharmaceutical formulation is at a pH of between 6.5±0.5 to 7.5±0.5.
3. The pharmaceutical formulation of statement 1, wherein the pharmaceutical formulation is at a pH of between 6.0±0.15 to 7.5±0.15.
4. The pharmaceutical formulation of statement 1 or 2, wherein the GLP-1 or analogue thereof is GLP-1 (7-37) and comprises the amino acid sequence set forth in SEQ ID NO:2.
5. The pharmaceutical formulation of any one of statements 1 to 4, wherein the GLP-1 or analogue thereof is ROSE-010 and comprises the amino acid sequence set forth in SEQ ID NO:3.
6. The pharmaceutical formulation of any one of statements 1 to 5, wherein the GLP-1 or analogue thereof is at a concentration of between 10 μg/ml to 2 mg/ml.
7. The pharmaceutical formulation of any one of statements 1 to 5, wherein the GLP-1 or analogue thereof is at a concentration of between 50 μg/ml to 2 mg/ml.
8. The pharmaceutical formulation of any one of statements 1 to 5, wherein the GLP-1 or analogue thereof is at a concentration of between 100 μg/ml to 1 mg/ml.
9. The pharmaceutical formulation of any one of statements 1 to 5, wherein the GLP-1 or analogue thereof is at a concentration of between 10 μg/ml to 1 mg/ml.
10. The pharmaceutical formulation of any one of statements 1 to 5, wherein the GLP-1 or analogue thereof is at a concentration of between 50 μg/ml to 750 μg/ml.
11. The pharmaceutical formulation of any one of statements 1 to 5, wherein the GLP-1 or analogue thereof is at a concentration of between 100 μg/ml to 500 μg/ml.
12. The pharmaceutical formulation of any one of statements 1 to 5, wherein the GLP-1 or analogue thereof is at a concentration of between 200 μg/ml to 500 μg/ml.
13. The pharmaceutical formulation of any one of statements 1 to 12, wherein the pharmaceutical formulation is at a pH of between 6.5±0.15 to 7.0±0.15.
14. The pharmaceutical formulation of any one of statements 1 to 13, wherein the pharmaceutical formulation comprises a surfactant.
15. The pharmaceutical formulation of statement 14, wherein the surfactant is a non-ionic surfactant.
16. The pharmaceutical formulation of statement 14, wherein the surfactant is polysorbate 20, polysorbate 40, polysorbate 60, polysorbate 65, polysorbate 80, Triton X-100, poloxamer, pluronic F-68 or combination thereof.
17. The pharmaceutical formulation of any one of statements 1 to 13, wherein the pharmaceutical formulation comprises polysorbate.
18. The pharmaceutical formulation of any one of statements 1 to 17, wherein the buffering agent is acetate, carbonate, citrate, histidine, maleate, phosphate, succinate, tartrate, tromethamine.
19. The pharmaceutical formulation of any one of statements 1 to 18, wherein the tonicity agent is a sugar.
20. The pharmaceutical formulation of any one of statements 1 to 18, wherein the tonicity agent is selected from the group consisting of dextrose, glucose, glycerin glycerol, mannitol, potassium chloride, sodium chloride, sodium sulfate, sorbitol, sucrose, trehalose or combination thereof.
21. The pharmaceutical formulation of any one of statements 1 to 20, wherein the pharmaceutical formulation comprises an excipient.
22. The pharmaceutical formulation of statement 21, wherein the excipient comprises an amino acid excipient.
23. The pharmaceutical formulation of statement 22, wherein the amino acid excipient is alanine, arginine, isoleucine, glutamate, glycine, leucine, methionine, proline, and the like and combination thereof
24. The pharmaceutical formulation of any one of statements 1 to 23, wherein the pharmaceutical formulation is at a pH of 6.5±0.5.
25. The pharmaceutical formulation of any one of statements 1 to 23, wherein the pharmaceutical formulation is at a pH of 7.0±0.5.
26. The pharmaceutical formulation of any one of statements 1 to 23, wherein the pharmaceutical formulation is at a pH of 7.5±0.5.
27. The pharmaceutical formulation of any one of statements 1 to 23, wherein the formulation is at pH 7.0±0.15.
28. The pharmaceutical formulation of any one of statements 1 to 23, wherein the formulation is at pH 6.5±0.15.
29. The pharmaceutical formulation of statement 1 or 28, wherein the GLP-1 analogue is as set forth in SEQ ID NO:3 and is at a concentration of from about 50 μg/ml to about 2 mg/ml.
30. The pharmaceutical formulation of statement 1 or 28, wherein the GLP-1 analogue is as set forth in SEQ ID NO:3 and is at a concentration of from about 100 μg/ml to about 1 mg/ml.
31. The pharmaceutical formulation of statement 1 or 28, wherein the GLP-1 analogue is as set forth in SEQ ID NO:3 and is at a concentration of from about 100 μg/ml to about 500 μg/ml.
32. The pharmaceutical formulation of statement 1 or 31, wherein the GLP-1 analogue is as set forth in SEQ ID NO:3 and is at a concentration of 300 μg/ml±20%.
33. A pharmaceutical formulation as described in the present disclosure.
34. A pharmaceutical formulation as described in Table 1A, Table 1B, Table 1C, Table 1D, Table 1E or Table 4.
35. The pharmaceutical formulation of any one of statements 1 to 34, in a unit-dose vial, multi-dose vial, cartridge or pre-filled syringe.
36. The pharmaceutical formulation of any one of statements 1 to 34, wherein the formulation is encapsulated.
37. A single-dose or multiple-dose container comprising the pharmaceutical formulation of any one of statements 1 to 34.
38. A pre-filled syringe comprising the pharmaceutical formulation of any one of statements 1 to 34.

39. A method of treating a disorder or condition in which administration of a GLP-1 or a GLP-1 analogue is indicated, the method comprising administering the pharmaceutical formulation of any one of statements 1 to 36 to an individual in need.

40. The method of statement 39, wherein the disorder is irritable bowel syndrome (IBS), constipation predominant IBS (IBS-C), diarrhea predominant IBS (IBS-D) or diarrhea predominant IBS (IBS-D).

41. The method of statement 39 or 40, wherein the pharmaceutical formulation is administered subcutaneously.

42. The method of any one of statements 39 to 41, wherein the pharmaceutical formulation is administered during acute pain associated with IBS, IBS-C, IBS-D or IBS-M.

43. The method of statement 42, wherein the disorder is diabetes, ischemia, reperfused tissue injury, dyslipidemia, diabetic cardiomyopathy, myocardial infarction, acute coronary syndrome, obesity, catabolic changes after surgery, hyperglycemia, stroke, neurodegenerative disorders, memory and learning disorders, islet cell transplant functional dyspepsia and/or a disorder requiring regenerative therapy.

44. The method of any one of statements 39 to 43, wherein the GLP-1 analogue is administered at a dose of from 50 µg to 150 µg.

REFERENCES

All patents, patent applications and publications referred to throughout the application are incorporated herein by reference.

Hellström P M, et al., Clinical trial: the GLP-1 analogue ROSE-101 for management of acute pain in patients with irritable bowel syndrome: a randomised, placebo-controlled, double-blind study. *Aliment Pharmacol Ther* 29: 198-206, 2009

Michael Camilleri, et al., Effect of a glucagon-like peptide 1 analog, ROSE-010, on GI motor functions in female patients with constipation-predominant irritable bowel syndrome. *Am J Physiol Gastrointest Liver Physiol* 303: G120-G128, 2012

Mojsov, S., Int. J. Peptide Protein Research, 40:333-343 (1992)

Doyle, B. D. et al, Biophysical Signatures of Noncovalent Aggregates Formed by a Glucagonlike Peptide-1 Analog: A Prototypical Example of Biopharmaceutical Aggregation, Journal of Pharmaceutical Sciences, vol. 94(12), p. 2749, 2005

U.S. Pat. No. 8,642,548 issued on Feb. 4, 2014, Peter Richardson et al.,

U.S. Pat. No. 6,583,111

WO2007/028394

WO91/11457

Zölls, S et al., The AAPS Journal. Vol 15(4), p. 1200, 2013 (reference to MFI, page 78)

The invention claimed is:

1. A liquid pharmaceutical formulation comprising a GLP-1 analogue consisting of the amino acid sequence set forth in SEQ ID NO:3, wherein the GLP-1 analog is at a concentration of 50 µg/ml to 2 mg/ml, and wherein the liquid pharmaceutical formulation is at a pH of between 6.5±0.5 and 7.5±0.5 and comprises a) histidine HCl at a concentration of about 10 mM±10%, b) a sugar-based tonicity agent at a concentration of from 100 mM to 450 mM c) polysorbate 20 at a concentration of from 0.005 to 0.05% and d) an amino acid excipient at a concentration of from 5 mM to 75 mM.

2. The liquid pharmaceutical formulation of claim 1, wherein the sugar-based tonicity agent is mannitol at a concentration of from 150 mM to 350 mM.

3. The liquid pharmaceutical formulation of claim 1, wherein the sugar-based tonicity agent is sucrose at a concentration of from 145 mM to 440 mM.

4. The liquid pharmaceutical formulation of claim 1, wherein the amino acid excipient is methionine at a concentration of from 5 mM to 25 mM.

5. The liquid pharmaceutical formulation of claim 1, wherein the amino acid excipient is proline at a concentration of from 25 mM to 75 mM.

6. The liquid pharmaceutical formulation of claim 1, wherein the GLP-1 analogue is at a concentration of from 100 µg/ml to 1 mg/ml.

7. The liquid pharmaceutical formulation of claim 1, wherein the GLP-1 analogue is at a concentration of from 100 µg/ml to 500 µg/ml.

8. The liquid pharmaceutical formulation of claim 1, wherein the GLP-1 analogue is at a concentration of 300 µg/ml±20%.

9. The liquid pharmaceutical formulation of claim 1, wherein the liquid pharmaceutical formulation is at pH 7.0±0.5.

10. The liquid pharmaceutical formulation of claim 1, wherein the GLP-1 analogue consists of the amino acid sequence set forth in SEQ ID NO:3 at a concentration of from 50 µg/ml to 2 mg/ml, wherein the liquid pharmaceutical formulation comprises histidine-HCl at a concentration of about 10 mM, mannitol at a concentration of about 275 mM, methionine at a concentration of about 10 mM and polysorbate 20 at a concentration of about 0.02%.

11. The liquid pharmaceutical formulation of claim 1, wherein the GLP-1 analogue consists of the amino acid sequence set forth in SEQ ID NO:3 at a concentration of from 50 µg/ml to 2 mg/ml, wherein the liquid pharmaceutical formulation comprises histidine-HCl at a concentration of about 10 mM, sucrose at a concentration of about 235 mM, methionine at a concentration of about 10 mM and polysorbate 20 at a concentration of about 0.02%.

12. The liquid pharmaceutical formulation of claim 1, wherein the liquid pharmaceutical formulation is selected from the group consisting of:
   a. a liquid pharmaceutical formulation comprising a GLP-1 analogue consisting of an amino acid sequence as set forth in SEQ ID NO:3, wherein the GLP-1 analogue is at a concentration of from 100 µg/ml to 1 mg/ml and wherein the liquid pharmaceutical formulation comprises histidine-HCl at a concentration of 10 mM, mannitol at a concentration of 275 mM, methionine at a concentration of 10 mM and polysorbate 20 at a concentration of 0.02%, and;
   b. a liquid pharmaceutical formulation comprising a GLP-1 analogue consisting of an amino acid sequence as set forth in SEQ ID NO:3, wherein the GLP-1 analogue is at a concentration of from 100 µg/ml to 1 mg/ml and wherein the liquid pharmaceutical formulation comprises histidine-HCl at a concentration of 10 mM, sucrose at a concentration of 233 mM (8%), methionine at a concentration of 10 mM and polysorbate 20 at a concentration of 0.02%.

13. The liquid pharmaceutical formulation of claim 12, wherein the liquid pharmaceutical formulation is at pH 7.0±0.5.

14. A single-dose or multiple-dose container comprising the liquid pharmaceutical formulation of claim 12.

15. A liquid pharmaceutical formulation comprising a GLP-1 analogue consisting of an amino acid sequence as set forth in SEQ ID NO:3, wherein the GLP-1 analogue is at a concentration of from 50 µg/ml to 2 mg/ml and wherein the liquid pharmaceutical formulation is at a pH of between of 6.5±0.5 and 7.5±0.5 and comprises:

a. histidine-HCl at a concentration of about 10 mM±10%, mannitol at a concentration of from 100 mM to 350 mM, and polysorbate 20 at a concentration of from 0.01 to 0.03% (w/v);
   b. histidine-HCl at a concentration of about 10 mM±10%, mannitol at a concentration of 165 mM±10%, and polysorbate 20 at a concentration of from 0.01 to 0.03% (w/v);
   c. histidine-HCl at a concentration of 10 mM±10%, mannitol at a concentration of 275 mM±10%, and polysorbate 20 at a concentration of from 0.01 to 0.03% (w/v);
   d. histidine-HCl at a concentration of 10 mM±10%, mannitol at a concentration of 275 mM±10%, polysorbate 20 at a concentration of from 0.01 to 0.03% (w/v) and methionine at a concentration of from 5 mM to 25 mM;
   e. histidine-HCl at a concentration of 10 mM±10%, mannitol at a concentration of 165 mM±10%, polysorbate 20 at a concentration of from 0.01 to 0.03% (w/v) and methionine at a concentration of from 5 mM to 25 mM;
   f. histidine-HCl at a concentration of 10 mM±10%, mannitol at a concentration of 275 mM±10%, polysorbate 20 at a concentration of from 0.01 to 0.03% (w/v) and proline at a concentration of from 25 mM to 75 mM;
   g. histidine-HCl at a concentration of 10 mM±10%, mannitol at a concentration of 165 mM±10%, polysorbate 20 at a concentration of from 0.01 to 0.03% (w/v) and proline at a concentration of from 25 mM to 75 mM;
   h. histidine-HCl at a concentration of 10 mM±10%, sucrose at a concentration of from 145 mM to 450 mM, and polysorbate 20 at a concentration of from 0.01 to 0.03% (w/v);
   i. histidine-HCl at a concentration of about 10 mM±10%, sucrose at a concentration of about 235 mM±10%, and polysorbate 20 at a concentration of from 0.01 to 0.03% (w/v);
   j. histidine-HCl at a concentration of about 10 mM±10%, sucrose at a concentration of about 290 mM±10%, and polysorbate 20 at a concentration of from 0.01 to 0.03% (w/v);
   k. histidine-HCl at a concentration of about 10 mM±10%, sucrose at a concentration of about 235 mM±10%, polysorbate 20 at a concentration of from 0.01 to 0.03% (w/v) and methionine at a concentration of from 5 mM to 25 mM;
   l. histidine-HCl at a concentration of about 10 mM±10%, sucrose at a concentration of about 290 mM±10%, polysorbate 20 at a concentration of from 0.01 to 0.03% (w/v) and methionine at a concentration of from 5 mM to 25 mM;
   m. histidine-HCl at a concentration of about 10 mM±10%, sucrose at a concentration of about 235 mM±10%, polysorbate 20 at a concentration of from 0.01 to 0.03% (w/v) and proline at a concentration of from 25 mM to 75 mM, or;
   n. histidine-HCl at a concentration of about 10 mM±10%, sucrose at a concentration of about 290 mM±10%, polysorbate 20 at a concentration of from 0.01 to 0.03% (w/v) and proline at a concentration of from 25 mM to 75 mM.

* * * * *